US009116835B1

(12) United States Patent
Smyth

(10) Patent No.: US 9,116,835 B1
(45) Date of Patent: Aug. 25, 2015

(54) METHOD AND APPARATUS FOR ESTIMATING CEREBRAL CORTICAL SOURCE ACTIVATIONS FROM ELECTROENCEPHALOGRAMS

(71) Applicant: U.S. Army Research Laboratory ATTN: RDRL-LOC-I, Adelphi, MD (US)

(72) Inventor: Christopher C. Smyth, Fallston, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/499,625

(22) Filed: Sep. 29, 2014

(51) Int. Cl.
  *A61B 5/04* (2006.01)
  *G06F 19/12* (2011.01)
  *G06N 5/02* (2006.01)
  *G06N 99/00* (2010.01)
  *A61B 5/0476* (2006.01)

(52) U.S. Cl.
  CPC .............. *G06F 19/12* (2013.01); *A61B 5/0476* (2013.01); *G06N 5/027* (2013.01); *G06N 99/005* (2013.01)

(58) Field of Classification Search
  None
  See application file for complete search history.

(56) References Cited

U.S. PATENT DOCUMENTS

| 8,708,884 | B1 | 4/2014 | Smyth | |
| 2005/0020933 | A1* | 1/2005 | Sato | 600/544 |
| 2006/0251303 | A1* | 11/2006 | He et al. | 382/128 |

OTHER PUBLICATIONS

Hairston WD, Letowski TR, and McDowell K, "Low-level auditory processing as a predictive tool for within- and cross-model performance," presented at the 27th Army Science Conference, Orlando, FL (2010).
M. Napflin, M. Wildi, and J. Sarnthein, "Test-retest reliability of resting EEG spectra validates a statistical signature of persons", Clinical Neurophysiology, 118, 2519-2524 (2007).
U.S. Appl. No. 14/499,562, titled "Node Excitation Driving Function Measures for Cerebral Cortex Network Analysis of Electroencephalograms," filed Sep. 29, 2014.
U.S. Appl. No. 13/792,585, titled "Apparatus and Method for Estimating and Using a Predicted Vehicle Speed in an Indirect Vision Driving Task," filed Mar. 11, 2013.
U.S. Appl. No. 13/721,161, titled "Method and Apparatus for Facilitating Attention to a Task," filed Dec. 20, 2012.

* cited by examiner

*Primary Examiner* — Etsub Berhanu
(74) *Attorney, Agent, or Firm* — Eric Brett Compton

(57) ABSTRACT

Methods and apparatuses for estimating activation of cerebral cortical sources from scalp site measurements of electroencephalograms (EEG) from a human subject are provided. In an exemplary embodiment, a method comprises: specifying cortical neural sources within the brain of the subject; simulating activation potentials for the specified cortical neural sources; projecting the simulated cortical neural source voltage activations to scalp site measurements locations for the subject; simulating scalp voltage potentials for one or more extra-cranial sources outside the brain; constructing simulated scalp site voltage potentials from the projected simulated modeled cortical neural source voltage activations and the simulated extra-cranial scalp voltage potentials; comparing the simulated scalp site voltage potentials and the electroencephalograms scalp site measurements for the subject; and adjusting parameters for simulating the cortical neural source voltage activations until the simulated scalp site voltage potentials generally correspond to the electroencephalograms scalp site measurements based on the comparison.

18 Claims, 58 Drawing Sheets

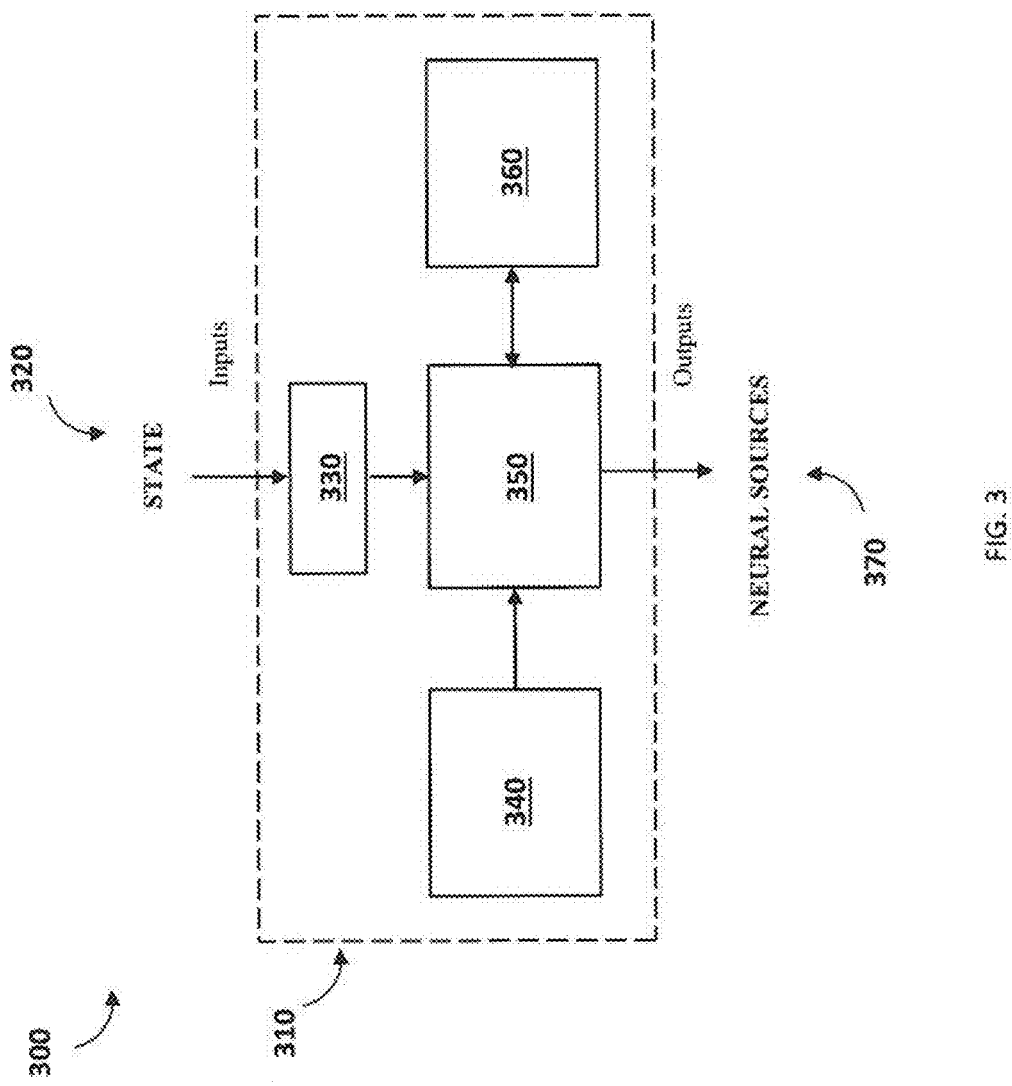

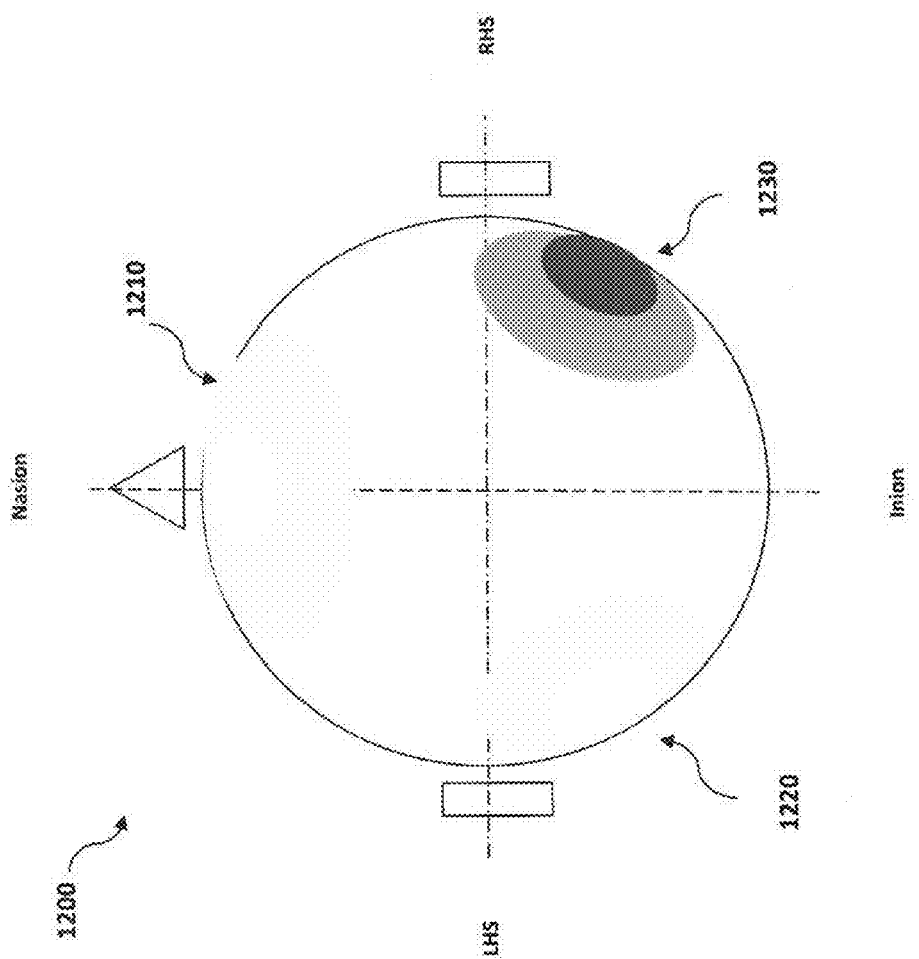

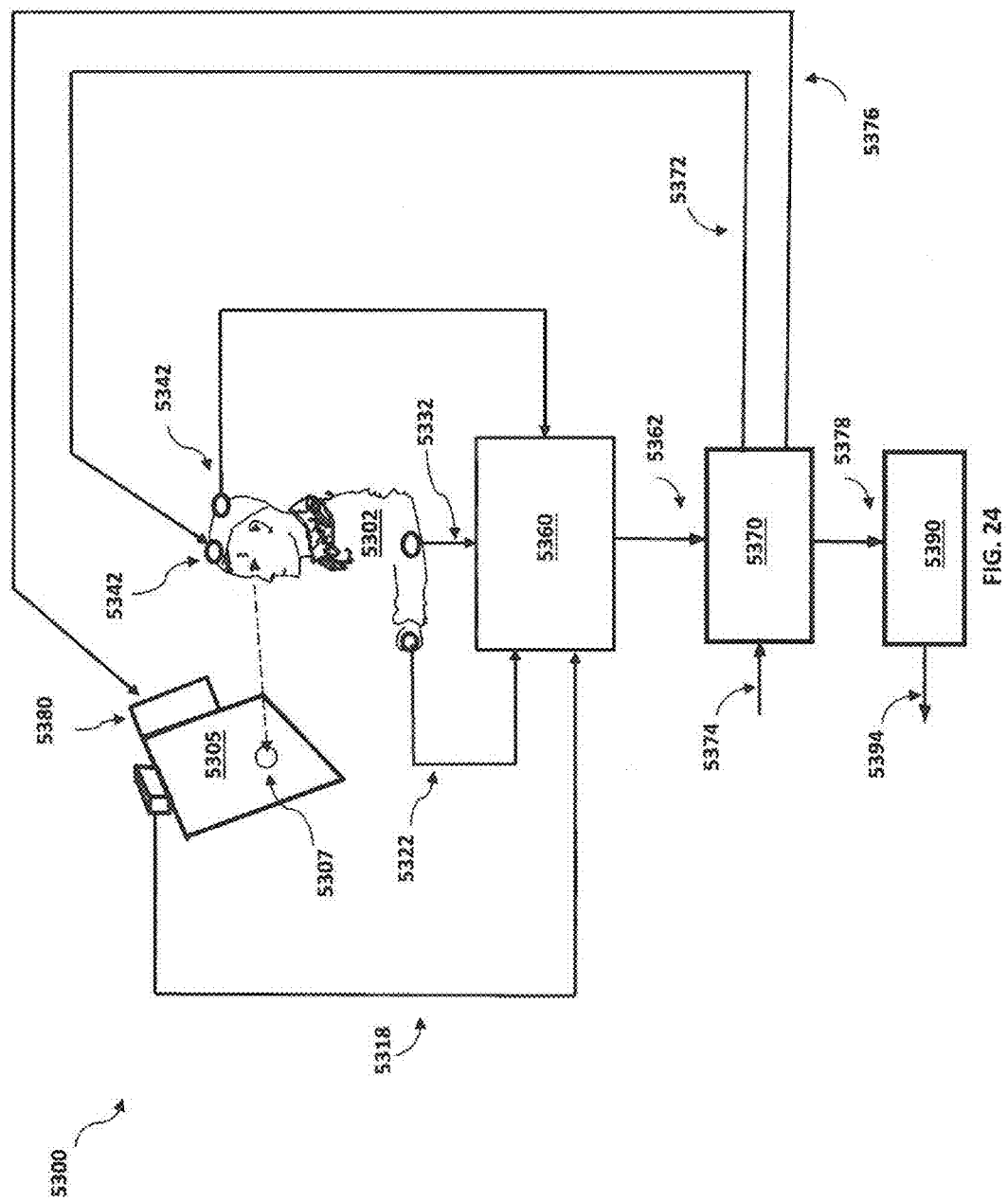

METHOD AND APPARATUS FOR ESTIMATING CEREBRAL CORTICAL SOURCE ACTIVATIONS FROM ELECTROENCEPHALOGRAMS

GOVERNMENT INTEREST

The invention described herein may be manufactured, used and licensed by or for the U.S. Government.

RELATED APPLICATION(S)

This patent application is related to U.S. patent application Ser. No. 14/499,562 filed Sep. 29, 2014, titled "NODE EXCITATION DRIVING FUNCTION MEASURES FOR CEREBRAL CORTEX NETWORK ANALYSIS OF ELECTROENCEPHALOGRAMS.", herein incorporated by reference in its entirety.

FIELD OF INVENTION

Embodiments of the present invention generally relate to determining brain activity from scalp site recorded electroencephalograms (EEGs).

BACKGROUND OF THE INVENTION

Brain cognitive activity is commonly determined from the scalp distribution of signal parameters following artifact rejection and signal analysis of electroencephalograms (EEG) measured with a scalp site electrode EEG data collection system. The signal analysis may be spectral analysis or multivariate autoregressive analysis, resulting in frequency band decompositions of the site signals; the distribution depends on the reference electrode used with the data collection system. Artifacts potentials are predominately generated from ocular sources such as eye-movements or blinks, or from muscular sources such as with facial or limb movements. In the art, artifact rejection techniques are employed to isolate EEG segments with artifacts from the data set based on such characteristics as excessive signal amplitude (>+50 uv or <50 uv), trend (+/−70 uv/epoch size), spectral content (ocular <2 Hz; muscular >40 Hz), and amplitude kurtosis (>3), among others, following baseline removal. Following artifact rejection, blind source separation using independent component analysis commonly based on signal amplitude kurtosis, may be applied to the reduced data set to derive independent signal sources, which are then separated into artifacts and cortical sources by signal characteristics such as waveform, spectral content, and kurtosis, as well as location within a standard shell head as derived from the signal scalp distribution for the source; artifact sources are located outside the cortex about the skull, while cortical sources are distributed within. The result is a reduced set of cortical component sources, the potentials of which are additively projected back to the scalp sites from the source locations for further signal analysis; since the source number is less than the number of scalp sites, the back-projection is ill-conditioned and for that reason commonly approximated using the Moore-Penrose pseudo-inversion matrix with singular value decomposition, where the approximation is improved by increasing the number of scalp electrode sites.

In the art, data analysis is applied to the back-projected scalp site potentials as measures of cortical functioning, where signal analysis may be non-parametric spectral analysis or parametric multivariate autoregressive analysis, resulting in frequency band decompositions of the site signals, commonly in the delta (2-5 Hz), theta (5-7 Hz), alpha (I: 8-10 Hz; II: 10-12 Hz), and the beta (12-20 Hz) frequency band ranges. In some prior art, data analysis is applied directly to the cortical component sources resulting from blind source separation without back projection to the sites. Application of the autoregressive process results in noise covariance and autoregressive coefficients, from which spectrums may be computed for the sites and the interactions among the sites. These methods can be extended using short-term Fourier analysis or wavelet analysis to produce a time-frequency spectral data analysis for the sites. The spectral results may be decomposed into spectrum band power; spectrum coherence computed from the power spectral matrix; and Granger causality for the coherence between the sites as a network. Further refinement in decompositions may be found in the prior art where the spectrum coherence (as a measure of mutual synchronicity among sites), may be decomposed into different measures of the Granger causality for the direction of information flow among sites. These measures include the directed coherence (DC), which is the ratio of the transfer function between two nodes, and the square root of the auto power of one of the nodes; and the directed transfer function (DTF), the ratio of the transfer function between two nodes, and the square root of the dot product of the vector of the transfer functions for the inputs to one of the nodes with its conjugate transpose, as well as the partial directed coherence, a function of the autoregressive model coefficients used in the spectral analysis. In further developments in the prior art, graph theory measures are applied for analysis of the sites as nodes of a network, by using small world network metrics computed from the cross-correlation matrices for the sites, such as node degree (average number of connections nodes), clustering coefficient (ratio of existing connections to all possible), diameter (shortest path between nodes), and efficiency (measure of number of parallel connections among nodes), among others. In experimental studies, statistical analysis may be applied to these measures by treatments for study results.

Commonly in the art, the scalp topological and power spectrum frequency distributions for site signals are reported in the literature as indicators of cognitive processing. Some examples of research results found in the prior art, follow: Alpha band (8-12 Hz) power has been shown to decrease with task performance, at least for arithmetic, recalling, and visual and auditory memory tasks. Theta band (4-7 Hz) power increased during spatial and verbal tasks, with a large increase over the right hemisphere in the spatial task. Frontal theta activity is associated with increased mental processing during challenging tasks; prefrontal excitation and lateralization in the anterior regions are indicative of high mental workload. Theta coherence between prefrontal and posterior cortical regions occurs with cognitive switching between tasks during the task setup and associated memory transfer, followed by upper alpha band suppression with memory processing at completion of task setup. A repetitive task sequence is associated with suppressed lower alpha band involved in attention and expectancy. Similarly, reported in the literature are results for cortical component sources resulting from blind source separation; in particular, results for driving studies in which such cortical sources show tradeoffs in activations between the frontal cortex and the motor cortex depending upon whether activities are a response to course deviation or problem solving during simulated driving.

While these are important results, as will be demonstrated in the specifications our own research using the mechanics of this invention for the evaluation of the effectiveness of these EEG analysis techniques of the prior art has shown limits to the validity at three levels: isolating the true cortical signal from the data for analysis, specifying the location of the sources within the cortex for cortical networks, and the manner of representing source activation for network analysis. Application of the invention mechanics to the prior art techniques of artifact rejection and blind source separation for isolation of the true cortical signal has shown that the resulting sources are not truly separated, since the cortical component sources retain some artifact and not all cortical signal is removed from the artifact sources. The retention depends in part upon the artifact rejection thresholds and the ratio of artifact-noise to the pure cortical signal in the data, since segments highly contaminated will be rejected leaving a reduced data set with mostly signal, while those with moderate artifacts may fail rejection and be included with the pure signal. The signal amplitude for the cortical based signal is on the order of micro-volts, while that of the artifacts is on the order of millivolts, although the order may be much less during micro-saccade eye-movements or fine muscle movements and initiation; further, muscular artifacts can have spectrum components within the 25 Hz range of the pure signal. Another problem is that the data set with artifacts may correspond to the activity period of interest while those without may correspond to periods between activities, and analysis of this data may result in a resting state measure of cortical activity. While, the blind source separation process separates out eye-movements and muscle sources from cortical sources by source localization, the process does not fully separate the spectrum contents since as has been noted, both muscular and ocular artifacts have spectrum components within the pure signal range. Again, the accuracy of the back-projection method, an ill-conditioned process, depends upon the number of scalp sites, and the accuracy deteriorates rapidly for smaller site numbers such as on the order of 19-sites for the standard 10-20 electrode system.

Therefore, if measurement of electroencephalograms (EEG) with a scalp site electrode EEG data collection system is to be useful in real life applications such as in moving vehicles with operator control, there is a need in the art for a method and apparatus for more accurately determining cerebral source excitations from the EEG measurements.

BRIEF SUMMARY OF THE INVENTION

Embodiments of the present invention provide methods and apparatuses for estimating cortical source activations from scalp site measurements of electroencephalograms (EEG) from a human subject. In an exemplary embodiment, a method comprises: specifying cortical neural sources within the brain of the subject; simulating activation potentials for the specified cortical neural sources; projecting the simulated cortical neural source voltage activations to scalp site measurements locations for the subject; simulating scalp voltage potentials for one or more extra-cranial sources outside the brain; constructing simulated scalp site voltage potentials from the projected simulated modeled cortical neural source voltage activations and the simulated extra-cranial scalp voltage potentials; comparing the simulated scalp site voltage potentials and the electroencephalograms scalp site measurements for the subject; and adjusting parameters for simulating the cortical neural source voltage activations until the simulated scalp site voltage potentials generally correspond to the electroencephalograms scalp site measurements based on the comparison.

The cortical neural source voltage activations can be simulated by a noise driven autoregressive process. And, parameters for simulating the cortical neural source voltage activations can be adjusted by autoregressive spectra parameterization. The extra-cranial scalp voltage potentials can be simulated by simulating ocular electrooculogram and/or muscle electromyogram potentials. For example, ocular orientations and eye-blinks can be used as determinates for simulating electrooculogram potentials, and facial expressions and limb postures as used as determinates for simulating electromyogram potential sources.

Cortical source locations may be mapped to cortical structures relatable to brain functions, which at the least spatial resolution are located within Brodmann Areas using a spatial coordinate system of the human brain. In some embodiments, the cortical neural sources are determined from an attention state of the subject, wherein the attention state is processed from the activities of the subject and the cortical neural source determination is made from the corresponding brain functions for the attention state from the cortical structure mapping. And, for some applications, the attention state for the cortical neural source activations is used as a basis for automated electronic task aiding of cognitive tasks (or manual tasks). The use for automated task aiding of cognitive employs transcranial direct current brain stimulation applied to enhance cortical neural source activations for the attention state.

In a further embodiment, an apparatus having a plurality of electronics modules to execute the aforementioned method is provided. Also, the apparatus may be incorporated as a component of an automated task aider used to estimate the task attention of the subject.

These and other embodiments are explained below in further detail.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. These embodiments are intended to be included within the following description and protected by the accompanying claims.

FIG. 3 is schematic of Expert System with knowledge of cortical neural sources;

FIG. 12a is a schematic of sample comparison process results for artifact mismatch.

FIG. 23c shows artifact source site spectrum power.

FIG. 24 shows an application of invention for crew aiding;

DETAILED DESCRIPTION OF THE INVENTION

Figure 1A:
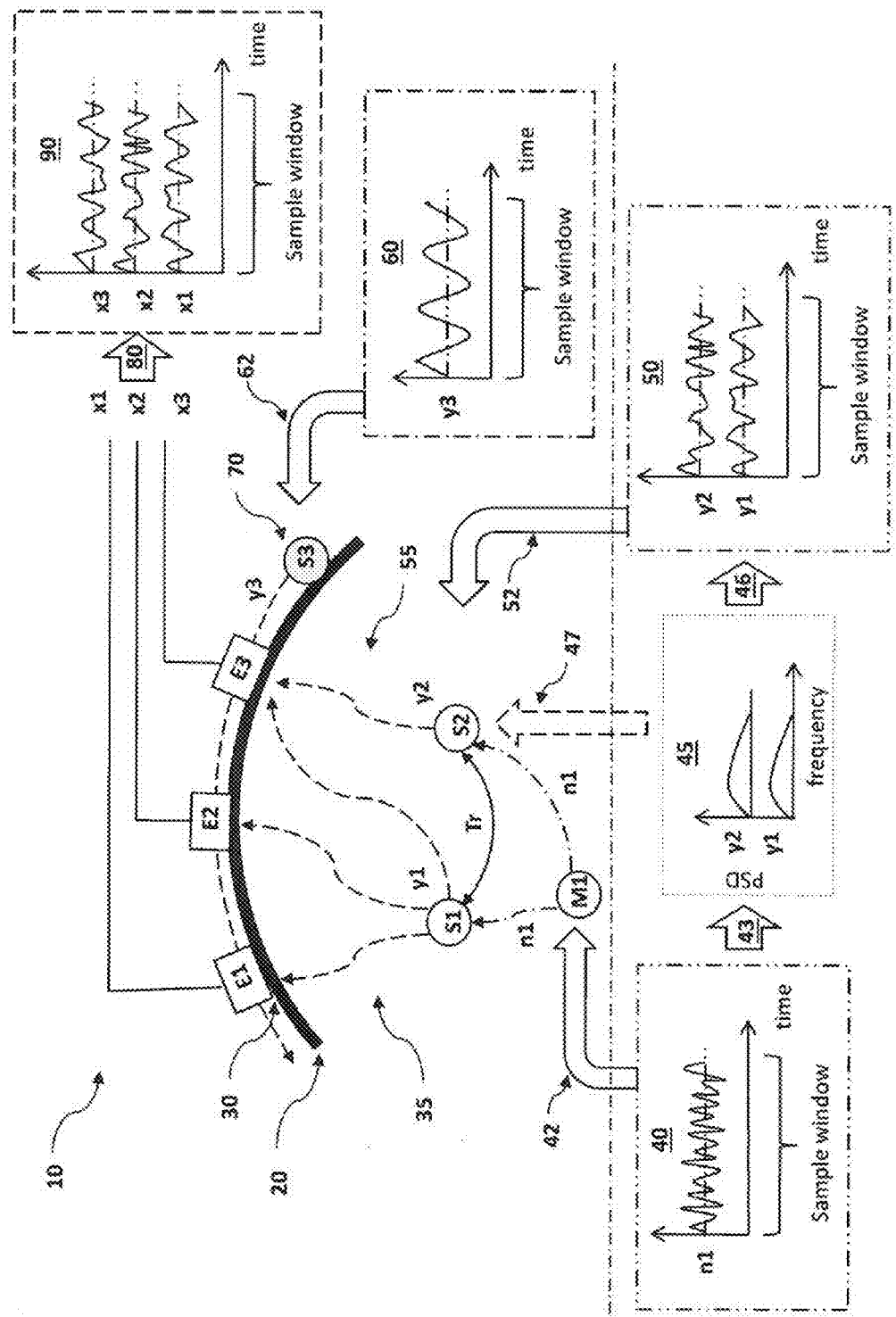
FIG. 1a is a schematic of the core simulation process elements essential as a component of an embodiment of the invention.

An innovative methodology for estimating cortical neural source activations from scalp site electroencephalograms of a human subject from the measurement of electroencephalograms (EEG) with a scalp site electrode EEG data collection system where multiple electrodes are positioned on scalp sites on the head of the subject is disclosed. The methodology uses novel modeling of cortical neural source activations based on a simulation which assumes that the scalp site voltage potentials are the sum of cortical neural source activation potentials within the brain and artifact potentials arising from one or more sources outside the brain. Potentials from extra-cranial sources are typically referred to as "artifacts" in the art of electroencephalogram analysis, and in conventional EEG analysis, this data would ordinarily be intentionally excluded from the EEG measurement data by employing artifact rejection techniques to isolate EEG segments with artifacts from the data set. By contrast, in the novel methodology of the present invention, artifact data is deliberately generated and included in the simulation processing.

More particularly, simulated cortical neural source potentials may be generated by a noise driven autoregressive process. In this process, neural oscillators can be driven as recursive filters by the white noise generator. Parameters for the neural source oscillators are commonly specified in terms of their frequency spectrum parameters of power, bandwidth, and peak frequency, for instance. Simulated artifact potentials may be generated by extra-cranial sources outside the brain, such as muscle and ocular potential sources. The simulated cortical neural source potentials are projected as signal potentials at the scalp site locations where EEG measurements are made. In the one embodiment, a standard three-dimensional spherical head model is used to project the source excitations from their cortical locations to the scalp sites, where the source locations are embedded in a NMI reference Talairach head coordinate space by Brodmann Areas.

The simulated scalp site data is compared to actual recorded EEG data (e.g., in a digitized data file) for the subject without artifact rejection applied to derive a baseline data set which has the simulated cortical neural source potentials alone as a reference. A recursive technique may be used to adjust the source model parameters for an improved or "best fit" of the compared signals. Adjustments may be iteratively applied. In some embodiments, the results of standard signal analysis techniques such as spectral analysis or multivariate autoregressive analysis may be used for comparison without artifact rejection applied. The "best fit" could use a conventional fitting algorithm, such as a 3th or 5th order polynomial, for example, if the polynomial is for a spatial distribution across the electrode sites (matching simulation to data at each site), and the polynomial is for zero predictor (i.e., the difference between the simulated and recorded values at each site is zero). Of course, the fit need not be in terms of raw data, but could be in terms of frequency band peak amplitudes, or frequency band powers.

The main data elements are shown for reference as a schematic 10 in FIG. 1*a* of the process for simulating recordings from skin-surface EEG sites 30 electrodes (here labeled E1, E2, E3 . . . in the figure) on the scalp 20. At the sites 30, electrical time-wise site voltage potentials signals (here x1, x2, x3 . . . , respectively), can be simulated and recorded (e.g., in a computer digital file) over a sampling period. The simulated data may be converted 80 to a file 90 for comparison to that for actual digitized recorded electroencephalogram (not shown), over the same time period.

In the simulation, the scalp-site 30 potentials are computed as the sum of the activation potentials (here labeled y1 and y2) from a plurality of cortical neural sources (here labeled S1 and S2) located within the cortex 35 in the brain, and of the artifact potential y3 from one or more extra-cranial sources S3 located outside 70 the skull, such as those from eye-movements, muscle movements, cardiac, or the environment, among others. These time-wise artifact potentials are generated by a separate process 60 feeding 62 the extra-cranial source S3, and the resulting voltage potentials y3 spread over the scalp 20 to the electrode sites 30.

The cortical neural sources (here labeled S1 and S2) located within the cerebral cortex 35, can be modeled and simulated as autoregressive process filters that are driven by a common white noise generator M1 as control modulator via control signals n1. The source filters, specified by power frequency spectrum densities 45 mapping 47 to the cortical neural sources, are excited 43 by the white noise process 40 for the 42 noise generator, resulting 46 in activation of voltage potentials 50 for the 52 sources. The potentials are spread 55 throughout the cortical volume and add together at the scalp electrode sites along with the artifact potential. This can be constructed by the site recorder electronics acting as a summing amplifier, for example.

The cortical neural sources (here, S1 and S2) represent discrete groups of neurons in the cortex of the subject's brain which have nearly identical receptive fields and function, and that grouped together are assumed to be located in Brodmann Areas in the brain. More particularly, the cortical sources may be brain regions of grouped neuron current dipoles located by the structure of the brain. The electroencephalogram is mostly generated by the neuron bodies (here represented by the cortical sources), in particular by coherent extracellular excitatory and activation currents circulating as current dipoles at the synaptic junctions of the apical dendrites at the somas in layers of tens of thousands pyramidal neurons. These neurons are organized together in columnar structures beneath several square millimeters of the cortical surface performing a common neurological function, and are found in the prefrontal cortex, the hippocampus, the entorhinal cortex, and other areas.

As known, Brodmann Areas are regions of the cerebral cortex having the same cytoarchitectural organization of neurons as originally defined and numbered by German neurologist Dr, Korbinian Brodmann in 1909. There are some 52 Brodmann areas which have been defined in human and non-human primates brains associated with various cognitive functions, although not all are present or used in human brains. So-called "Brodmann atlases" or "Brodmann maps" are available which depict the various Brodmann areas in the brain and indicate their functions.

These functional areas may be mapped to regions of the cerebral cortex having the same cytoarchitectural organization of neurons, and in turn may be located in a 3-dimensional coordinate system of the human brain. Brodmann Areas have been previously mapped to specific locations in the human brain. One way to do this is using Talairach space, a known 3-dimensional coordinate system of the human brain, which is used to map the location of brain structures independent from individual differences in the size and overall shape of the brain, with Brodmann areas as labels for both lateral and median surface brain regions (as derived by Jean Talairach and Gabor Szikla in 1967). Talairach space represents a standardized atlas or grid for mapping the human brain, which defines standard anatomical landmarks that could be identified on different individuals. An individual's brain image obtained through Magnetic Resonance Imaging (MRI), positron emission tomography (PET) and other brain imaging methods can be mapped to this standard Talairach space using conventional software applications. For example, atlases, such as the Talairach Daemon and CARET (Computerized Anatomical Reconstruction Toolkit) applications can approximate between three-dimensional locations in the brain and Brodmann Areas. Another way is through Montreal Neurological Institute (MNI) standard brain coordinate system, which is based on studies of Magnetic Resonance Imaging (MRI) data for a large number of persons. This latter technique is supposedly more representative of the population. There are various known functions for converting MNI standard brain coordinate system to Talairach space.

In the present methodology, not all Brodmann areas need to be used as cortical sources. One may choose to select a subset of one or more Brodmann areas which correspond to one or more cognitive functions of interest. The cortical sources which are assumed to correspond to Brodmann area locations in the subject's brain can be mapped to a standard cortical space coordinate system, like Talairach space or MNI standard brain coordinate system. In further embodiments, the cortical sources may be derived in a functional MRI brain study for the individual subject to identify regions linked to critical cognitive functions, such as speaking, moving, sensing, or planning, among others. In turn, the individual results may be again mapped to a standard cortical space for location as Brodmann Areas.

For reference, the cortical neural sources in FIG. 1*a* (here, S1 and S2) are shown connected by association neuronal fiber tracts (here labeled tr) forming brain function networks between the regions. As known in the art, some examples of interest to visual perception are the superior and inferior frontal-occipital tracts connecting regions of the occipital lobe to those of the orbitofrontal lobe, and the inferior longitudinal tracts connecting occipital and occipital lobe regions. Other tracts involve language (arcuate tracts), attention (cingulum), among others. The connections made with these tracts form cortical networks among the neural sources, where the networks may be cortical attention networks for eye-movements, working memory, spatial distribution, and temporal expectation, within the frontal, temporal and parietal brain regions. A default network corresponds to self-referral.

As further elaboration, the voltage potentials at the head scalp sites can be assumed to include and be the sum of potentials from simulated cortical neural current dipole sources embedded in a NMI reference Talairach head coordinate space. The sources can be simulated as neural oscillators; these oscillators can produce delta, theta, alpha, and beta band task specific spectral parameters of power, bandwidth, and peak amplitude, for example. These parameters are used to compute an equivalent set of autoregressive coefficients and in turn, a noise driven filter representation of the cortical signal potential. In this process, the source locations are transformed to those in a three or four-shell spherical head model; the dipole source potentials are the resultant of tangential and radial dipole components computed from the source location and orientation relative to the head model spherical surface. In a further embodiment, the dipole sources may be specified in the Talairach standard head by Brodmann area locations on the cortex surface for determining different electroencephalogram states, as a function of the distribution of dipole orientation, oscillator frequency, and moment intensity by locations, and of the timing in connectivity among the locations.

Further, the muscle and ocular artifact potentials may be simulated and generated by extra-cranial sources located on a template of the head scalp referenced in a spherical head model (i.e., ocular at eyes; muscles in face, at neck or brows). The artifact potentials at the scalp sites may be further attenuated by the spread of the extra-cranial source potential over the scalp. Considering the scalp as a conducting surface (the skull being insulating), the attenuation is related to the inverse of the scalp distance of the source from the site; while the scalp level brain potential is commonly on the order of microvolts, the artifact sources are commonly in the millivolt range.

For example, the ocular source potentials may be generated as electrooculograms (EOG) for the eyes, where the EOG is the retinal resting potential induced by a dipole potential between the cornea and the retinal; the dipole moment is constant for a steady state of dark adaptation and visual stimulus. As the eye rotates the scalp surface potential induced by the source potential is proportional to the angular rotation in both the vertical and horizontal directions; the scalp potential is computed from the EOG using a model of eye movements, both saccades and tracking pursuit. Further, eye-blinks may generate voltage potential equivalent in strength to that of eye-movements.

The muscle source potential may be generated from the sum of the motor neuron firings for a model of the muscle as a set of motor neuron units with recruitment threshold, firing rate and twitch force of the units related in an orderly fashion. An activation function determines how many units are recruited and their mean firing rate for a particular excitation force. For each motor unit recruited, a spike train with a Gaussian inter-spike interval distribution is generated and each spike causes a muscle twitch, with the total muscle force being the sum of all the twitches in all the recruited motor units. The firing rate is a function of the activation and the recruitment threshold for the unit; the coefficient of variation of the inter-spike interval is fixed for the individual. In this simulation the muscle model is determined by the number of motor units and the range of recruitment thresholds.

Figure 1B:
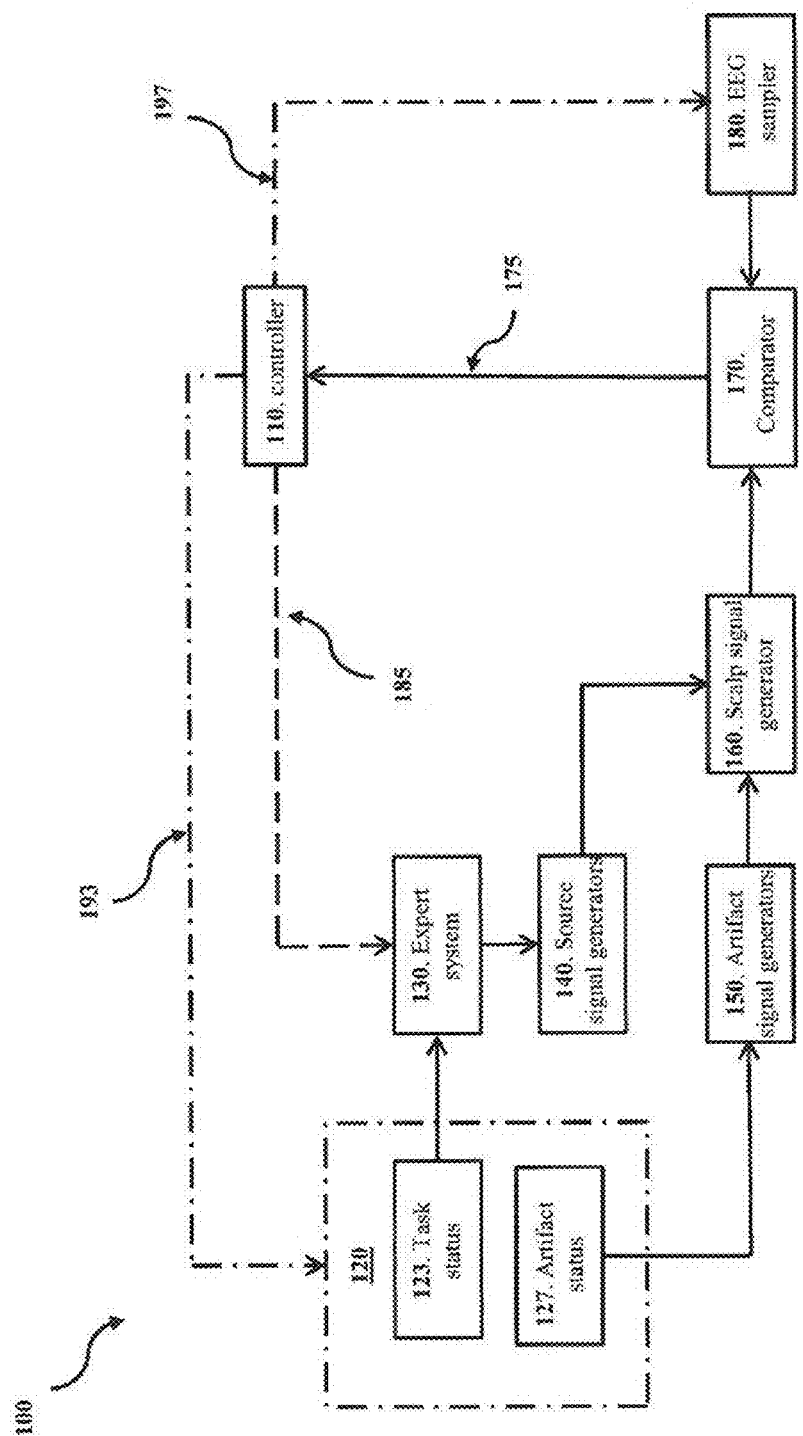
FIG. 1b is a schematic of an embodiment of invention.

FIG. 1b is a schematic of the simulation method described above in an embodiment 100 of the invention, including a controller 110, state status indicator 120, with task status 123 and artifact status 127 recorders, an expert system on neural sources 130, a neural source signal generator 140, artifact signal generator 150, a scalp site signal generator 160, an EEG signal sampler 180, and a signal comparator 170, with status output 175 to the controller. In this embodiment, the controller initializes the expert system by control signal 185, and activates the EEG sampler for recording a data sample, that in one embodiment is a short term data sample, by control signal 197 and the state status indicator by the control signal 193. The task status indicator reports the status of the task performed from operant activities of the operator such as measured ocular and manual functions, and from electronic record of the task. On that basis, the expert system specifies the cortical neural sources estimated to be representative of the operator brain functions, and with that input, the neural source signal generator computes the activation signals of the sources. Similarly, the artifact status indicator reports the status of the artifacts from operant activities of the operator such as measured ocular and manual functions, recorded electromyograms (EMG) for muscle activities, and knowledge of the environment. With that input, the artifact source signal generator computes the artifact signals. In turn, with inputs of the neural source signals and the artifact signals, the scalp signal generator computes the expected scalp site potentials over the sample period from the location and orientation of the neural sources, and from the locations of the artifacts relative to the scalp. The simulated scalp potential sample and the EEG data sample are compared by site, and the match statistics are input to the controller, with a reset of the expert system 185 for refinement of the neural source selections and repeating the simulation of scalp potentials, depending upon the degree of fit.

The embodiment 100 may be embodied as a plurality of electronic modules, for example, in some implementations. The electronic modules may be implemented as hardware, software or a combination thereof. The modules may be implemented with a computer of computing device having one or more processors (or micro-processors) as known in the art that are specifically configured to execute coding necessary to implement embodiments of the present invention. Processor-executable instructions can be stored in a memory device and execute by the processors when needed. In some implementations, software code (instructions), firmware, or the like, may be stored on a computer or machine-readable storage media having computer or machine-executable instructions executable by the processor(s). The processor(s) may be a programmable processor, such as, for example, a field-programmable gate array (FGPA) or an application-specific integrated circuit (ASIC) processor. The methodology disclosed herein may be implemented and executed by an application may be created using any number of programming routines, such as MATLAB. Of course, any number of hardware implementations, programming languages, and operating platforms may be used without departing from the spirit or scope of the invention. As such, the description or recitation of any specific hardware implementation, programming language, and operating platform herein is exemplary only and should not be viewed as limiting.

Figure 2A:
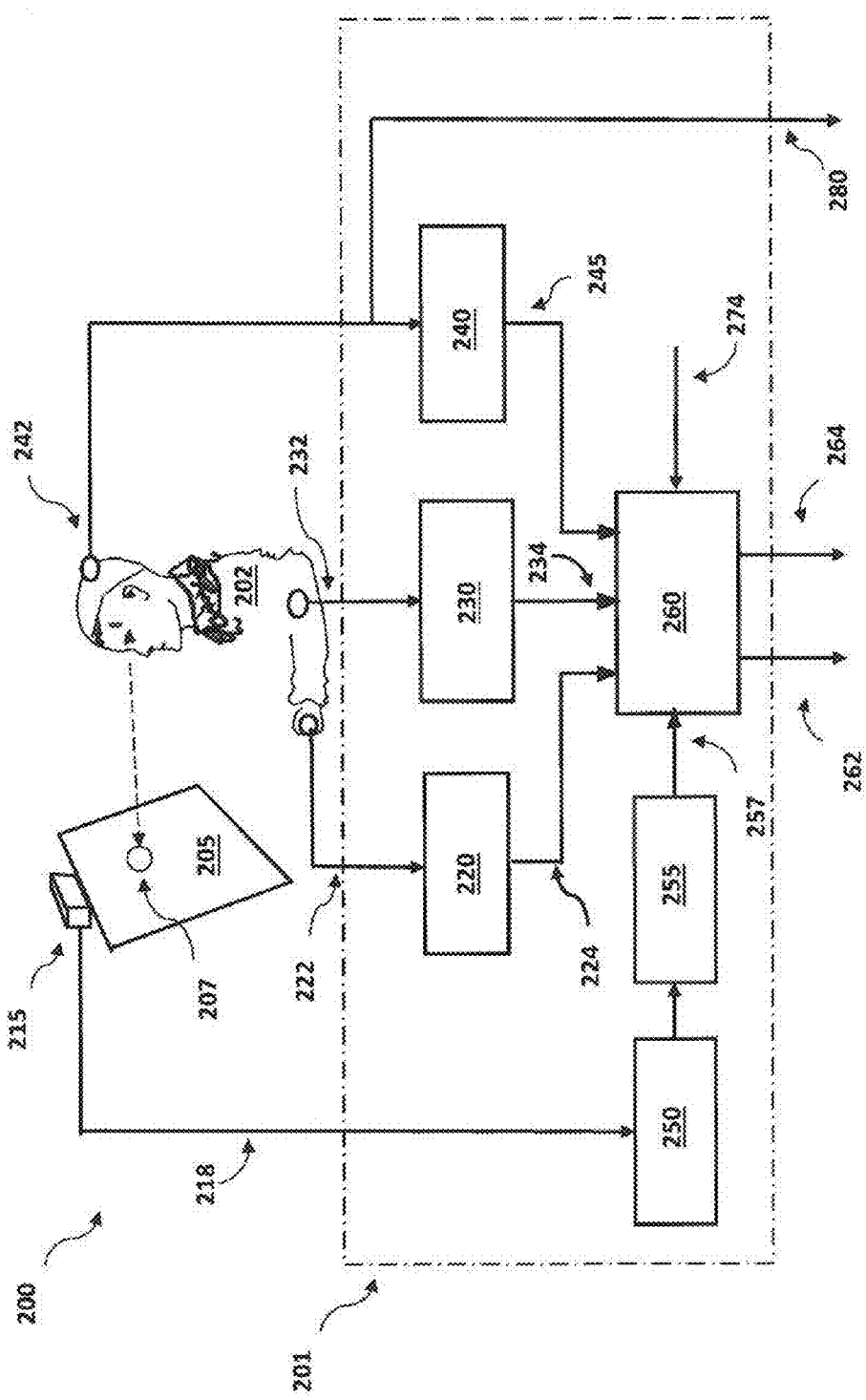
FIG. 2a is a schematic of pre-processor for Process Status Indicator.

The state status indicator recordings may be of real time status, and in some embodiments of short term statistics for the state processes. FIG. 2a is a schematic of a pre-processing system 200 for the state status indicator 120 (of FIG. 1), where the preprocessors receives recordings of the operator state. Here, the operator 202 is attending to an icon 207 presented on the visual display 205. Ocular functions may be recorded by an eye-tracker with video camera 215 in conjunction with a head-tracking for eye-movements, fixations, and blinks, and by electrooculograms (EOG) from skin site electrodes placed about the eye (not shown) and measuring skin potential induced by the corneo-retinal potential as the eye rotates. Manual functions may be recorded from limb activity measured by an actimeter 222 with embedded accelerometers attached to the wrist. In some embodiments, the EMG recordings 232 may be made using a bipolar electrode configuration for facial, head, and arm muscles. In some embodiments, the EEG signals collected from the scalp site electrodes may be processed as well. The EEG recording may be made from a scalp cap of multiple electrodes judiciously distributed about the scalp (for example, in a standard 10-20 International System electrode configuration, or the like), all with amplifiers having output 242. In this embodiment, these recordings are inputs to preprocessors within a module 201 for signal processing of the separate inputs. The video output 218 from the video camera goes to an eye tracker 250 with eye-movement processor 255, and output of eye-movements and fixation patterns 257; limb activity output 222 goes to motor activity estimator 220, for short-term movement and location statistics with output 224; EMG recordings to signal analysis module 230 for the linear envelope amplitude following filtering and wave rectified, and in some embodiments the power spectrum, with output 234; and EEG output to signal analysis module 240 for separation of artifact power from the raw signals and power spectrums for the treated signals by scalp sites, with output 245. The output 245 from the signal assessor 240, the output 224 from the motor activity estimator 220, and the output 252 from the eye-movement processor 257, are inputs along with the task status record 274 to 260 as a data router to the process state indicator 120 (of FIG. 1), with output 262 to (say) task status indicator 123 (of FIG. 1), and output 264 to artifact status indicator 127 (of FIG. 1); an additional output is of the raw EEG data 280 to the EEG sampler 180 (of FIG. 1).

In a further embodiment, the EEG signal analysis module 240 may be in the form of related U.S. patent application Ser. No. 14/499,562 showing innovative techniques for deriving an estimate of artifact and cortical sources from the short term EEG data base, and correspondingly deriving an estimate of the user's task attention state as inputs to router 260 as initial estimates for state modeling by the expert system 130 (FIG. 1). While an innovatively improved method of cortical network analysis, the techniques of the related application are limited to statistically similar data bases and since this is not necessarily the case in operational conditions, the method is applicable to initializing the task state modeling.

Figure 2B:
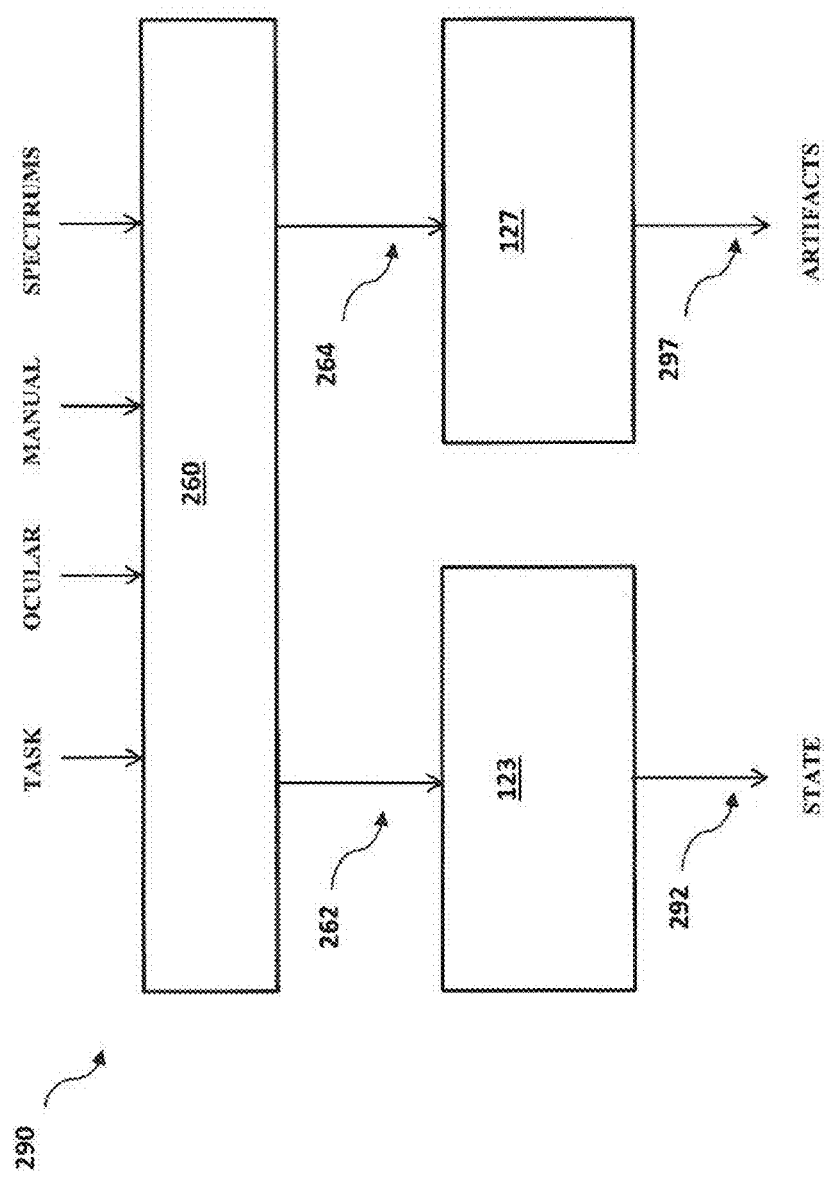
FIG. 2b is a schematic of Process Status Indicator modules.
Figure 4A:
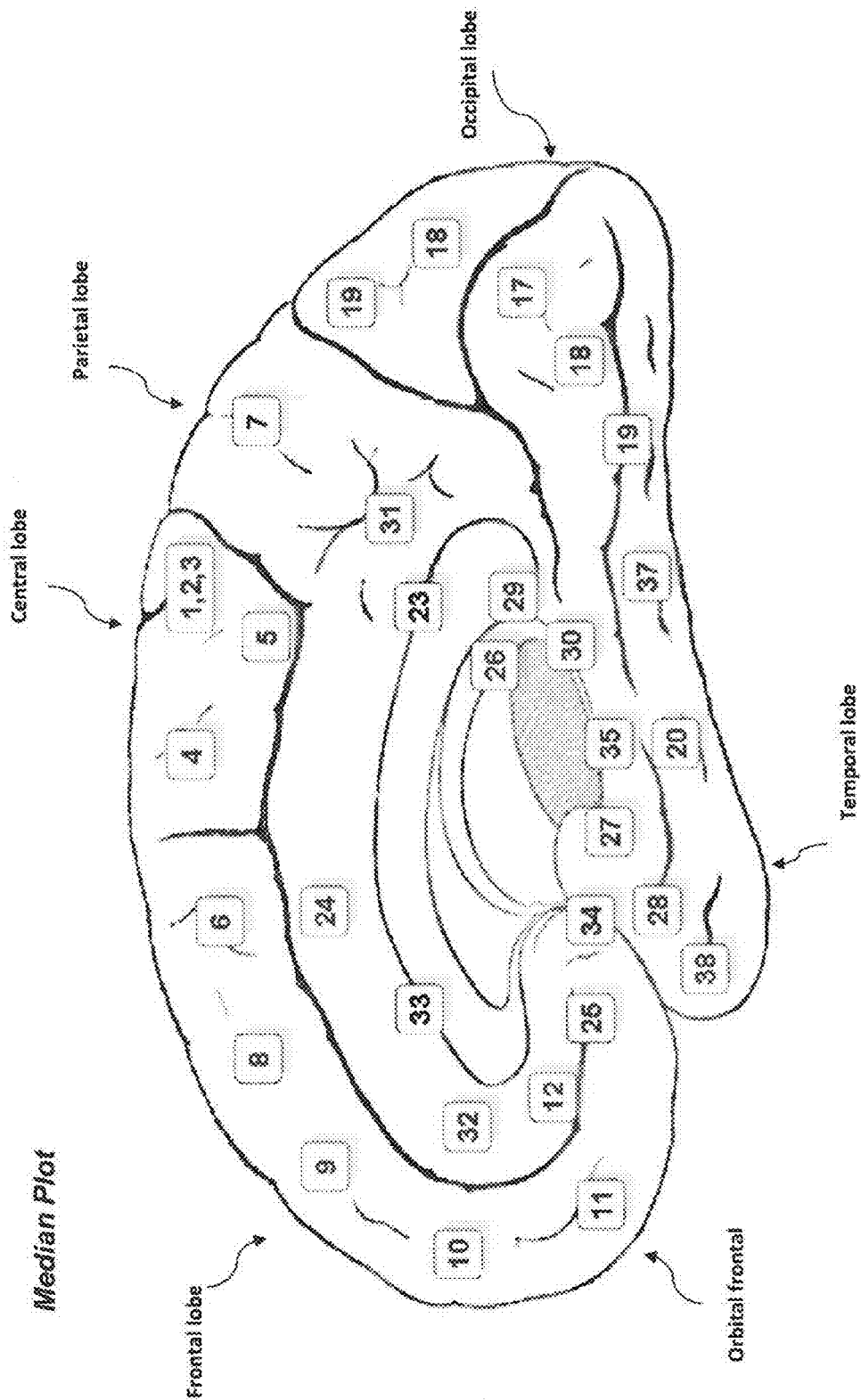
FIG. 4a shows a median view of the human cortex with numbered Brodmann Areas.
Figure 4B:
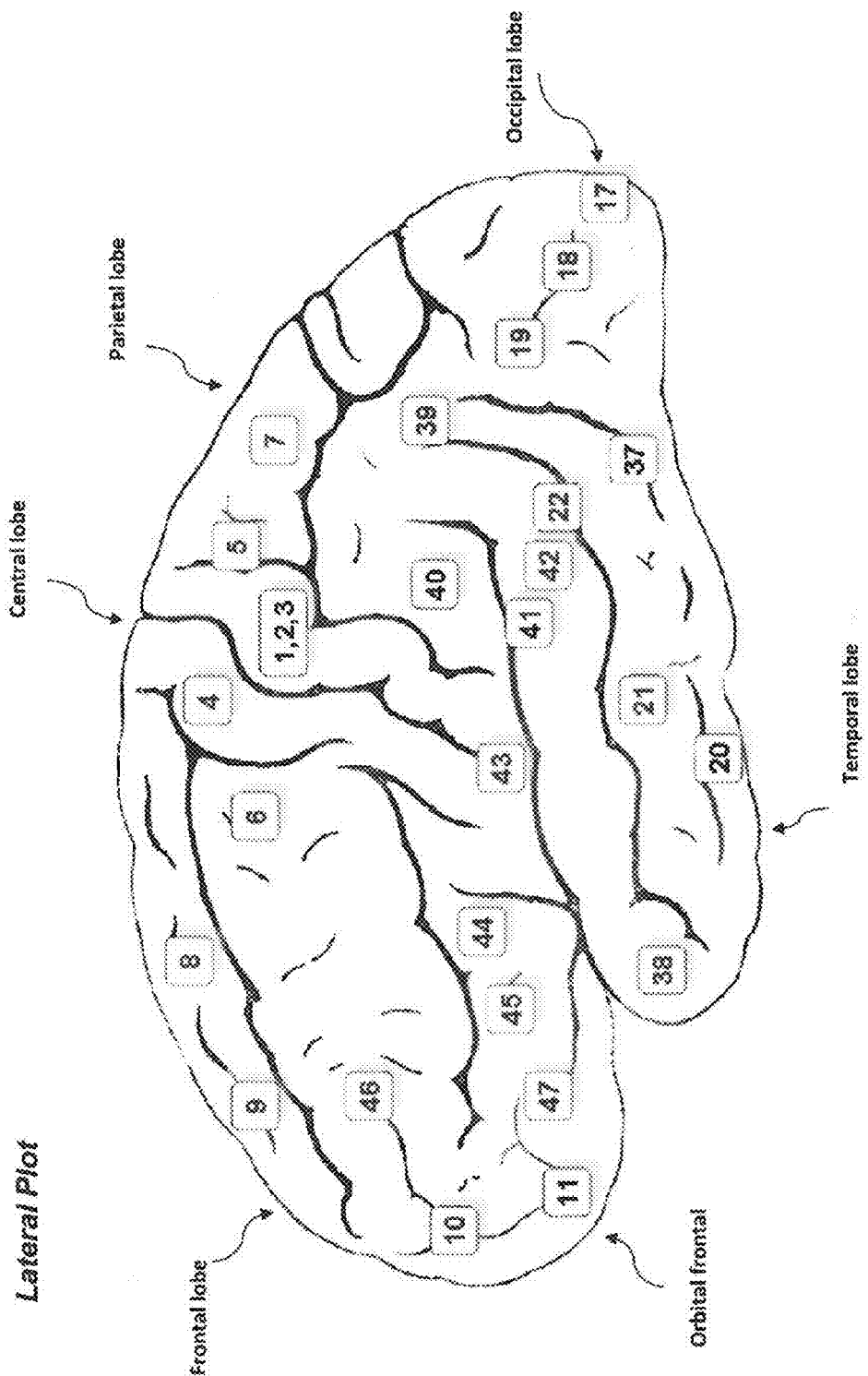
FIG. 4b shows a lateral view of the human cortex with numbered Brodmann Areas.

FIG. 2b is a schematic showing the routing connections 290 between inputs to router 260 (of FIG. 2a), and the outputs of the status indicators 123 and 127 (of FIG. 1). Here, the router inputs are data for the task status (TASK), the ocular activities (OCULAR), the manual activities (MANUAL), and the EMG and EEG artifact spectrums (SPECTRUMS). The inputs are combined in different sets depending upon the receiving status indicator, with the set for the task indicator 123 used to determine task attention state of the operator for output to the expert system, and that for the artifact indicator 127 used to determine the parameters for the artifact signal simulation. In one embodiment the task indicator set 262 (of FIG. 2a) consists of such as eye-fixation patterns and manual movement activities relative to that needed for the task, as well as the task performance record. Further, the artifact indicator set 264 consists of eye-movements and blinks relative to the EEG collection, and the EMG and EEG artifact spectrums. Here, the task indicator output 292 is of the task attention state to the expert system 130 (of FIG. 1), for determination of the brain functions. The artifact indicator output 297 is that of the artifact model parameters used in artifact signal generator 150 (of FIG. 1).

The expert system 130 (of FIG. 1) as shown as one embodiment in FIG. 3, is a knowledge base system 300 configured as an expert system 310, with an input buffer 330 (output 292 of FIG. 2b), knowledge base 360, inference engine 350, and inference rules 340, with input 320 here shown as task attention state (STATE), and following determination of the attention state, output 370 of representative brain cortical neural sources listing location, orientation, spectrum excitation parameters, and white noise driver properties. In this design, the input buffer may store time-wise sequential values. The knowledge base asserts relations among the inputs and brain states. The inference engine is an automated reasoning system that evaluates the current state of the knowledge-base, applies relevant rules, and then asserts new knowledge into the knowledge base using in one embodiment 'if-then' rules based on parameters set in a training session. In other embodiments, the classifier may be of different designs including those of discriminative models that maximize the output based on a training set, such as a logistic regression model, a support vector machine maximizing the margin between a decision hyperplane and the training set, or a multiple layered perceptron configured as an artificial neural network with nodes in an input, output, and hidden layers, with the nodes between adjacent layers connected with weighted links.

In this embodiment, the task attention state may be mapped through the knowledge base of the expert system to a state of information processing as expressed by a cognitive processing model for the human operator, and in particular, to the states of the separate processors making up the model from the corresponding cortical networks for the brain functions. In this process, the cognitive processing model may comprise cognitive processors controlled by a model executor, and rules for the activation of the corresponding processors as components of an information processing network. The model may be incorporated within a skills-based, rules-based, and knowledge-based model of cognitive processing; where the executor recalls task rules and in evaluation sets up the rules for activation, the rules base processor activates the rules directing control, and the skills based processor controls the task execution. In this model, the levels of involvement of the processors depend upon the attention state of the network as determined by the executor.

There is a neurological basis for the validity of such a model within the human cerebral cortex with the executor mapped to the orbitofrontal cortex involved in planning, the knowledge base to the temporal lobes, the rules processor to the anterior parietal and the pre-motor cortex with control setting to the motor cortex. The skills processor may be mapped to the cerebellum with a reference setting from the motor cortex and visual offset from the pontine nuclei via the posterior parietal for foveal vision or even directly from the visual cortex for peripheral vision. Further, the reference may be set by the parietal cortex in visual-egocentric coordinates for comparison to delayed visual returns. The cerebellum is believed essential to coordinating motor limb and digit movements. Each of these centers taken together may comprise cortical attention networks for eye-movements, working memory, spatial distribution, and temporal expectation, within the frontal, temporal and parietal brain regions.

In this model, the levels of processing comprise brain functions, where the brain functions are mapped to regions of the cerebral cortex having the same cytoarchitectural organization of neurons, labeled in the Talairach reference head space as Brodmann Areas (as defined and numbered by Brodmann in 1909). Talairach space is a 3-dimensional coordinate system of the human brain, which map the location of brain structures using Brodmann areas as labels for both lateral and median surface brain regions (as derived by Talairach and Szikla in 1967).

FIGS. 3a and 3b are Talairach space figures of median and lateral views of the cortex, with numbered Brodmann Areas (BA1, BA2, BA3, etc.). As reference, the cortical lobes are indicated: frontal, central, parietal, occipital, and temporal, along with the orbital frontal. These areas are organized as brain function processors by cortical lobes, with the occipital, somatosensory, and temporal cortical lobes organized for primary sensory areas (vision: BA17; somatosensory: BA1, 2, 3; temporal: BA41 for auditory, BA43 for gustatory), and secondary sensory areas (vision: BA18; somatosensory: BA5; temporal: BA42 for auditory), association areas (vision: BA19; somatosensory: BA7; temporal: BA22), along with multiple association areas in the parietal and temporal (BA20, 21, 15), which in turn lead to the frontal lobe for evaluation (BA9, 10, 11, 12), with pre-motor frontal eye-fields for directed vision (BA8), and secondary motor (BA6) and primary motor (BA4) for action. Specialized temporal and frontal areas process language understanding (BA39, 40) and generation (BA44, 45). These functions may be specialized further by cortical hemisphere. In addition, the anterior cingulate is believed involved in error detection (BA24, 32) and the posterior cingulate in emotion (BA23, 31). Further involved are the limbic system regions of entorhinal cortex (BA34), perirhinal cortex (BA35), and the ectorhinal area (BA36) of the perirhinal cortex, among others for spatial memory and orientation. Of course, this is not a complete rendition of brain areas and associated functions constituting the knowledge base.

Brain functions localized in Brodmann Areas are expressed in cortical networks connecting the neural sources, where the networks may be cortical attention networks for eye-movements, working memory, spatial distribution, and temporal expectation, within the frontal, temporal and parietal brain regions. Further, the active sources driving the network determine the state of task attention from the corresponding Brodmann Areas as to sensory processing (and as visual or auditory), association, evaluation and motor involvement. In this invention, the networks are conceptualized as activated by modulators acting as a white noise driver of the sources, through the frequency and power of noise source signals. In this process, the modulator sources are a measure of the strength of attention, while the network topology corresponds to the cognitive involvement. A default network corresponding to self-referral has less clustering and efficiency and is more spread out in a form of 'scale free' network; a task focused network would be spread out but with a high degree and high diameter, as well as high clustering and high efficiency; and a task response network would perhaps be a 'small-world' network that has less degree and diameter, and greater clustering and efficiency.

On this basis, the output 370 of the expert system to the source simulator 140 (of FIG. 1), comprises cerebral neural sources listed as infinitesimal electrical oscillator dipoles by cortical location and orientation (from location), as located by Brodmann Areas in the Talairach head space; along with the spectrum properties of the dipole oscillators, the network containing the sources, and the properties of the modulator as a white noise generator driving the network.

Figure 5:
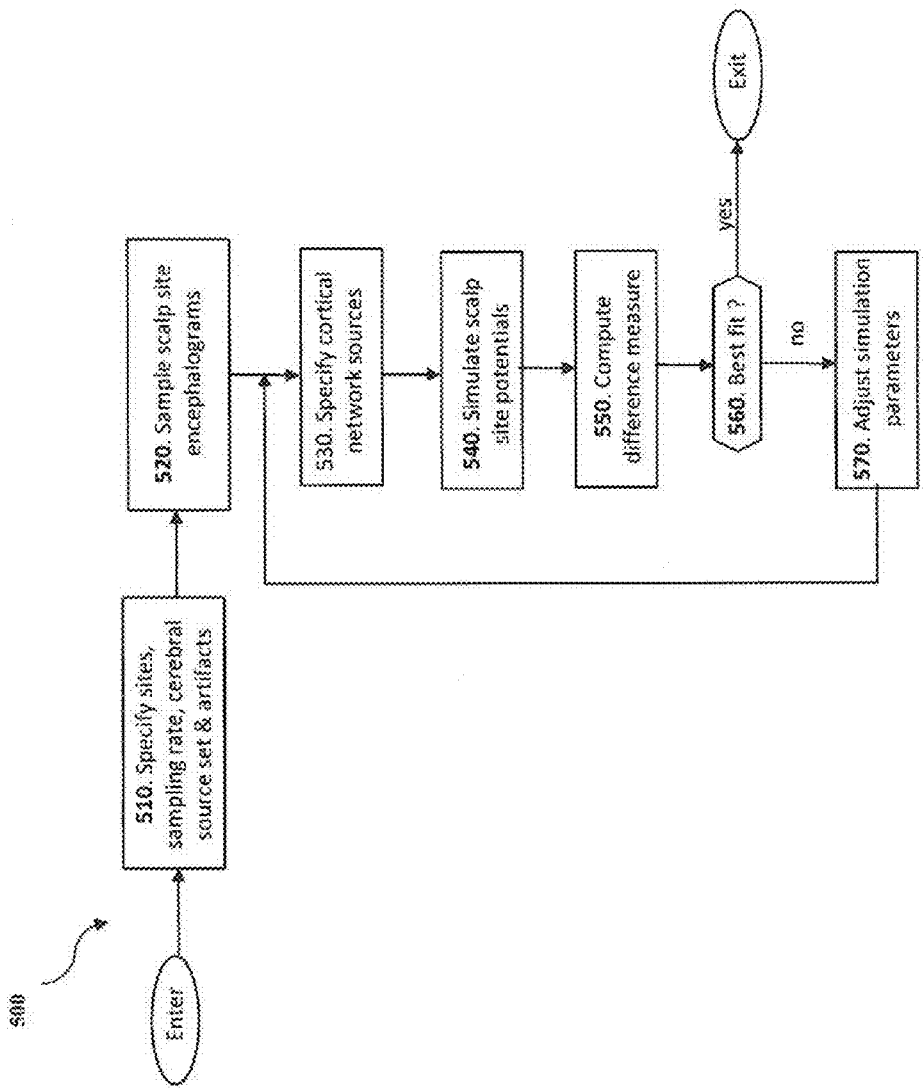
FIG. 5 is a flow chart of invention process for scalp signal simulation and sample comparison.

In one embodiment, the process for signal generation and sample comparison may be considered further from the flow chart of FIG. 5, where the invention sets up the simulation parameters 510, collects an encephalogram sample from scalp skin sites 520, and then enters a recursive routine in which the cortical neural sources are specified 530, the simulated scalp site potentials are calculated 540, and the computed signals are compared to the recorded data 550. This routine is repeated with adjustments to the source parameters 570 by the expert system until a best fit occurs 560, in which case the routine exits with the best fit cerebral source parameterization. These steps are elaborated as follows:

Simulation Parameters:

The parameters for the simulation are specified: the number of skin scalp electrode sites and the label and location according to the extended 10-20 electrode system in the coordinates of the spherical head model; the locations of the eyes and muscle artifact sources in the head model; the functional condition of the electrodes (good contact, broken contact, snapping contact); the sampling frequency and sample time; the parameters of the resonators representing the neural sources such as the peak frequency, bandwidth and fractional power; the parameters for an autoregressive process representing the neural source activations such as the autoregressive pole order and the process header needed for process stability; the characteristics of the motoneuron spiking sources for the muscles such as the number of contractile neuron motor units, the maximum normalized threshold, and the firing rate parameters; the scalp topological weighting factor for the spread of the source potentials over the scalp to the site as a function of the separation distance $(100/2pi*r)$; and then computes the inter-site separations between the sites and the eyes and the muscle sources.

Figure 6:
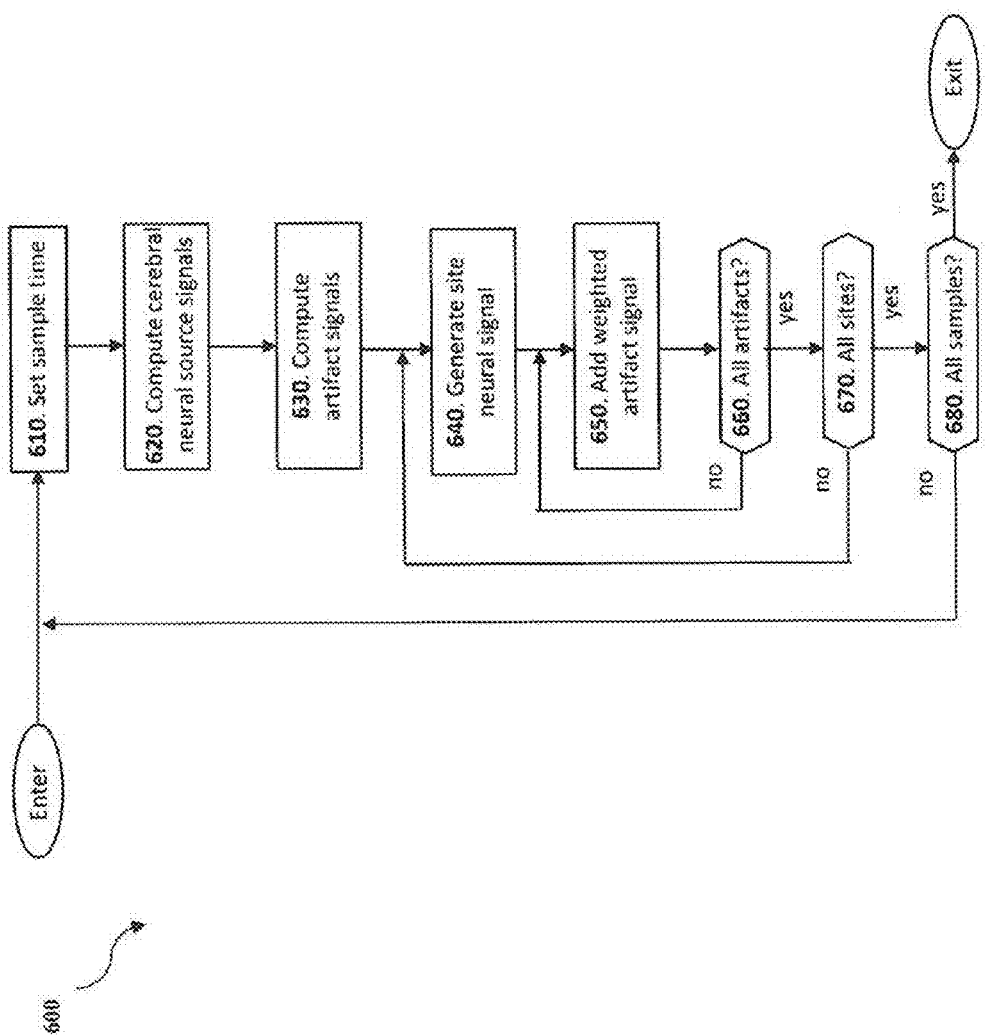
FIG. 6 is a flow chart of invention process for simulating scalp site potential.

Head Scalp Simulation:

The process provides a format for head scalp recording simulation by the location of electrode sites and artifact sources on a template of the head scalp referenced in the standard spherical head model (85 mm radius). The simulated electroencephalogram is the sum of the brain potential at a site with the potentials from these sources, following attenuation caused by the spread of the source potential over the scalp. Considering the scalp as a planar conducting surface (the skull being insulating), the attenuation is related to the inverse of the scalp distance of the source from the site; while the scalp level brain potential is commonly on the order of microvolts, the sources are commonly in the millivolt range. A time course specified for the scalp site brain potentials and the sources may be used to generate simulated electroencephalogram recordings. In detail, following the flow chart of FIG. 6, the method for each sample time 610, computes the cerebral source activations 620 as described below ('Neural Source Activation'), computes artifact signals 630 that in one embodiment are the eye electrooculograms ('Eye Movement Artifact Potential') and blink potentials ('Eye Blink Artifact Potential') following specifying the time path trajectory of a visual target being viewed, and the muscle potentials ('Muscle Artifact Potential') following specifying of excitation force time forms for muscle movements. The simulation projects the neural source potentials to the scalp sites 640 ('Neural Source Scalp Potentials'), and the simulated sample site signals are then computed for each sample time by adding the eye potentials and muscle potentials to the site brain potential following adjustment for the attenuation by the inter-site distance over the scalp 650, for all artifacts 660, and all sites 670. This process is repeated 680 for all sample times.

Figure 7A:
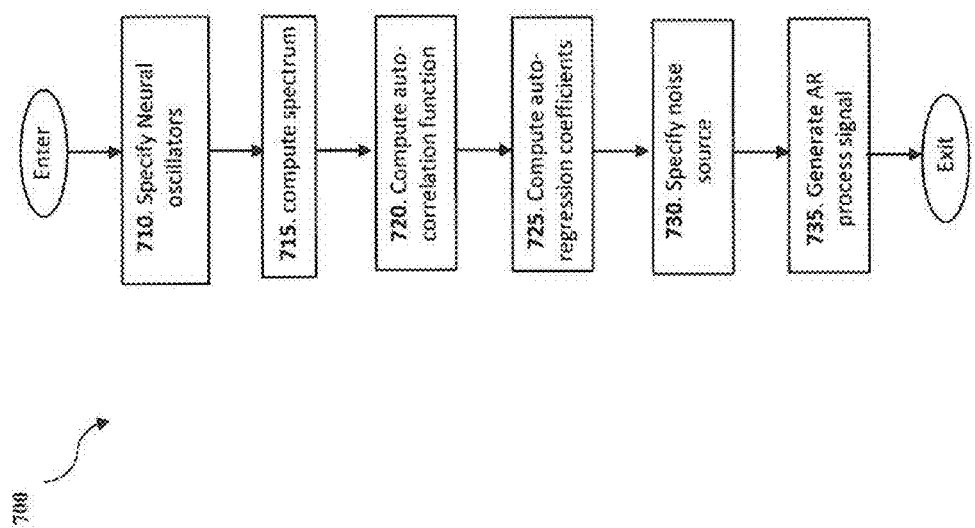
FIG. 7a is a flow chart of invention process for simulating cortical neural source activations.

Neural Source Activation:

The neural source activation is simulated as a set of neural oscillators for the different frequency bands: delta, theta, alpha1, alpha2, beta1, beta2, gamma, or as appropriate (FIG. 7a), where each oscillator is specified 710 by a set of spectral parameters composed of a central frequency, a half-power bandwidth, and the fractional power in the spectrum. The central frequency for the delta band (type I oscillator) is zero since the spectrum is centered at the origin, while an appropriate frequency for remaining type II is about 10 Hz for the alpha band and about 20 Hz for the beta band. The spectrum may be readily computed 715 for these simple units from the parameter set and in turn the autocorrelation functions computed 720 for the spectrum; see Table 1 for spectrum function pairs for the two types of oscillators. The signal spectrum is the sum of those for the oscillators, while in turn the signal autocorrelation function is the sum of those for the same.

Next, a set of autoregressive coefficients may be iteratively solved 725 for a noise driven filter representation of the signal from the autocorrelation function using the Levinson-Durbin recursive process (MATLAB 'levinson' function); the optimal order of the filter model may be determined from the Akaike information criteria as a measure of the relative goodness of fit. Finally, using a normal random noise source 730 for driving the filter, the source activation may be computed 735 by the autoregressive process assuming a minimum phase process (Matlab 'filter' function with random Gaussian noise input where the output is truncated to the last samples to avoid start-up transients).

Figure 7B:
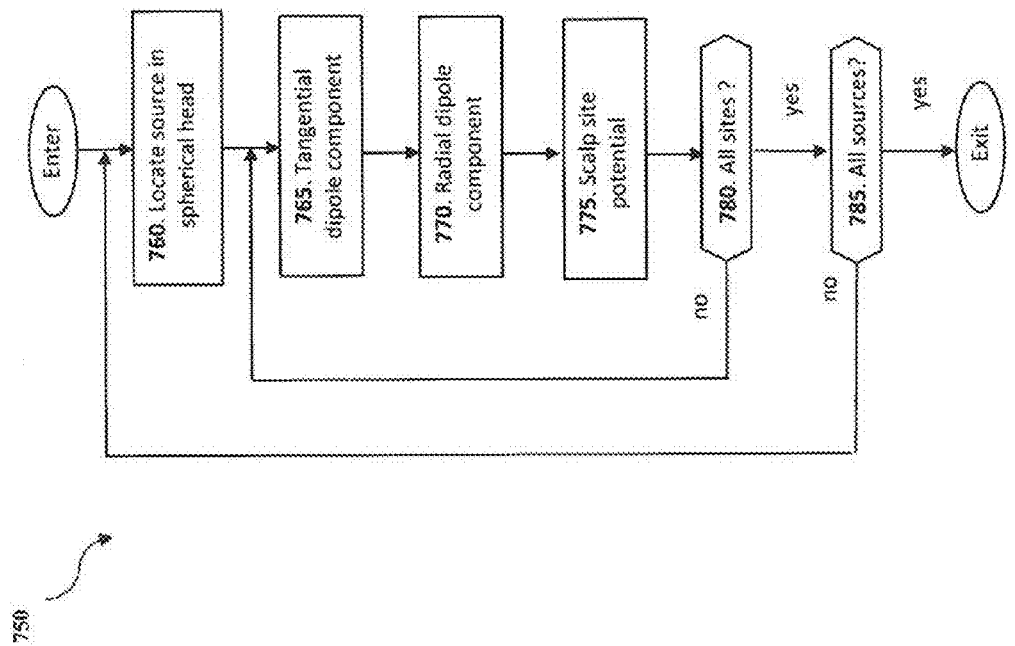
FIG. 7b is a flow chart of invention process for simulating cortical neural source head scalp potentials.

Neural Source Head Scalp Potential:

Cortical potentials at the head scalp sites are generated as the sum of the potentials from simulated neural dipole sources embedded in a NMI reference Talairach coordinate space with delta, theta, alpha, and beta band task specific spectral parameters of power, bandwidth, and peak amplitude. In this process 750 of FIG. 7b, the source locations are transformed to four-shell spherical head model locations 760, where the spherical head model may be mapped from a standard cortical space reconstructed from Montreal Neurological Institute (MNI) MRI data, and in turn from the Talairach space for the location of Brodmann Areas. The dipole source potentials at the scalp site are the resultant of tangential 765 and radial dipole 770 components computed from the source location and orientation relative to the head model spherical surface, using the dipole moment intensity with Berg parameters, for layer conductivities based on the Stok head model. The scalp site potentials generated by the neural sources are computed 775 for all sites 780 and all sources 785.

Eye Movement Artifact Potential:

The simulation makes use of the knowledge that the eye-movement artifact is generated by the dipole potential between the cornea and the retinal of the eye. As the eye rotates in the eye-orbit the change in the scalp surface potential induced by the dipole corneo-retinal potential is proportional to the angular rotation in both the vertical and horizontal directions; the dipole moment is constant for a steady state of dark adaptation and visual stimulus. The induced scalp surface potential distribution varies with the rotational angle and is attenuated with distance along the scalp from the eye-orbit. The simulation method depends upon the design of the pre-processor 201 (FIG. 2), where in one configuration, the electrooculograms for the eyes may be collected along with the encephalograms with electrodes positioned about the eye-orbits; the electrooculogram is proportional to the eye rotational angle relative to a reference potential as determined by the electrode montage, and the angle and therefore the corneo-retinal dipole potential may be estimated accordingly. In another configuration, the eye rotational angle may be measured with an eye-tracker and with knowledge of the viewing target and environment, the corneo-retinal dipole potential estimated. At the least, the simulation may use the corneo-retinal dipole potential multiplied by an amplification factor as the source of the artifact and compute the eye-movement artifacts for the sites from the scalp attenuation.

In a further embodiment, the invention may use statistics collected over the sampling interval to model eye-movements as a check on the determinations. This is based on research showing that eye movements are saccades or pursuit, driven by two different neurological control systems in response to angular offset of the foveal center from a visual target. Saccades are rapid ballistic rotational jumps made in response to target offsets greater than 0.5 degrees, with the angular velocity being sinusoidal and the maximum occurring half-way through the movement. Pursuit movements are slow steady rotations at a constant angular rate limited to a maximum velocity of 25 to 30 degrees per second, but greater than 1-degree per second. Saccadic jumps during pursuit are made in response to a target perceived as moving faster than 30-degrees per second. The eye with a 200 ms saccadic recovery time acts as a sampled data control system for unpredicted targets; however, the system can lead a predicted target. According to research, the saccade amplitude and duration are determined by target offset, with duration being a linear function of the offset and the maximum velocity an exponential function; as measured in experiments, nominal values for the duration are: $t=2.7*abs(offset)+37$, in ms, and for the maximum velocity: $Vm=551*(1-exp(-abs(offset)/14))$, in degrees per second.

Figure 8:
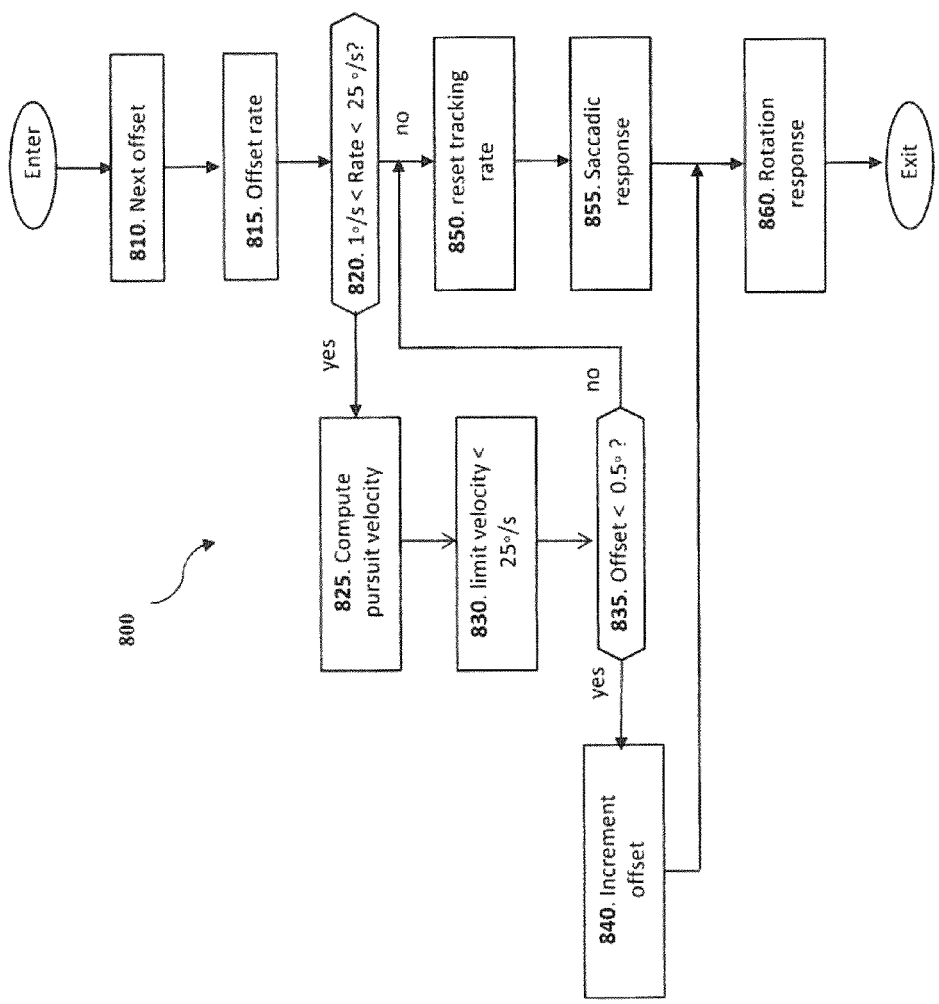
FIG. 8 is a flow chart of invention process for simulating eye-movement potential.

Following this reasoning, the simulation routine 900 for eye-rotations (FIG. 8), first predicts the next offset 810 increment from the sampled offset, computes the offset rate 815 for the sample period, and if the rate is greater than 1-deg/sec and less than 25-deg/sec[820], computes the pursuit velocity 825 (limited to 25-deg/sec[830]), and if the offset increment is less than 0.5 deg [835], continues to increment the angular response 840 at the pursuit rate for the sampling period; otherwise, the program resets the tracking rate 850, computes the response duration and maximum velocity for a saccadic response 855, and increments the rotation for the duration period 860. The end position is then held until the next sampling period. The electrooculogram is proportional to the eye rotational position relative to a reference potential as determined by the electrode montage, and the eye-movement artifact potential is computed accordingly.

Eye Blink Artifact Potential:

The simulation makes use of the knowledge that the blinking of the eyes performed as a rapid closing and opening of the eyelid, generates a positive upwards directed dipole potential across the cornea that appears in the encephalograms as an increase in the vertical electrooculogram. The pulse maximum amplitude varies from minimal to that equivalent to an electrooculogram potential for a 15-degree eye-rotation angle; the pulse duration is commonly 100 to 400 ms. The simulation method depends upon the design of the pre-processor 201 (FIG. 2), where in one configuration, the electrooculograms for the eyes may be collected and the blink occurrence reduced from the signal, along with the amplitude and duration. In another configuration, the blink may be measured with an eye-tracker. At the least, the simulation may use the blink generated potential multiplied by an amplification factor as the source of the artifact and compute the eye-movement artifacts for the sites from the scalp attenuation.

Figure 9:
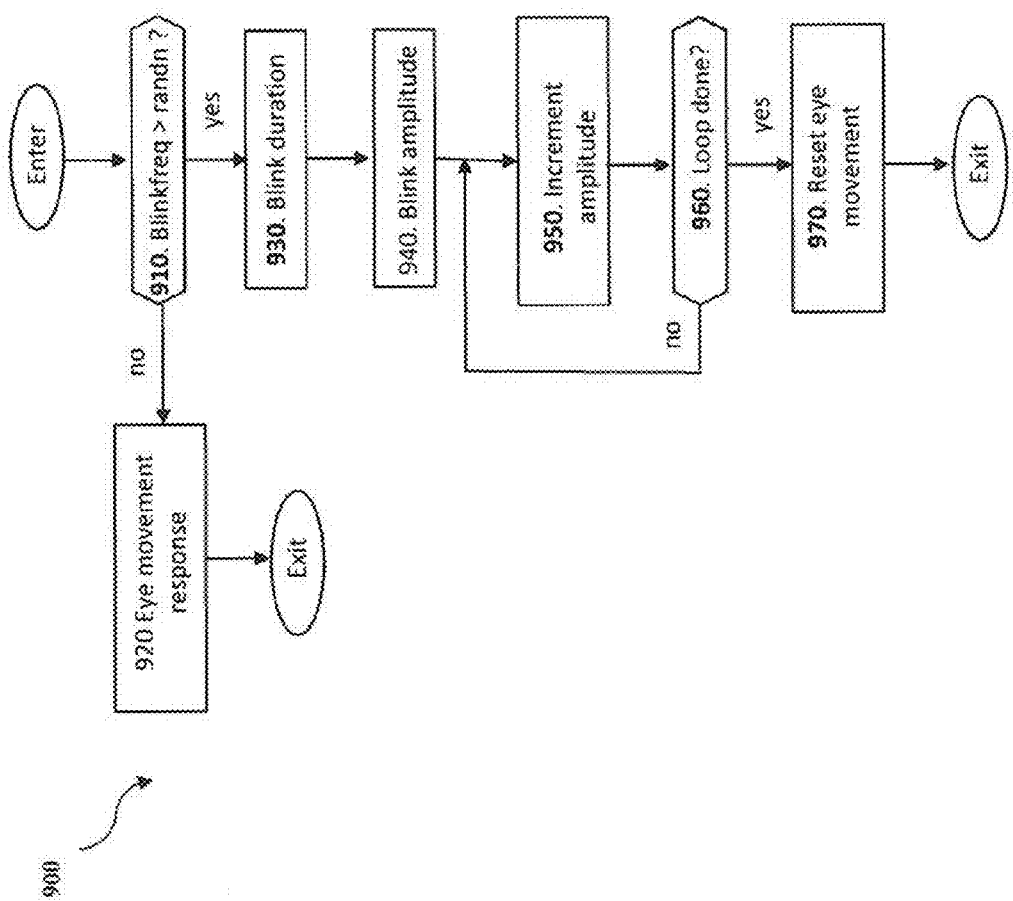
FIG. 9 is a flow chart of invention process for simulating eye-blink potential.

In a further embodiment, the process may use statistics collected over the sampling interval to model eye-blinks as a check on the determinations. This is based on research showing that blink rates vary with the individual averaging about 10 blinks per minute for adults in a laboratory setting; generally, blinks are separated by an interval of 2-10 seconds. The rate decreases to about 3 to 4 times per minute when the eyes are focused on an object for an extended period of time such as during reading. Such visual fixations are usually followed by a flurry of 2 or 3 blinks. Blinks may occur at the start of an eye movement, but rarely during a movement. Following this reasoning, the simulation routine 900 for eye-blinks (FIG. 9), tests for the occurrence of a random eye blink 910, and if so computes the blink duration 930 and maximum amplitude 940 as random draws, then computes the change in blink potential pulse as a function of sampled time 950, adding such to the eye position potential, and upon completion of the blink 960, resets the potential to that of the fixed eye 970; otherwise, proceeds to compute 920 the eye movement potential.

Muscle Artifact Potential:

The simulation makes use of the knowledge that a muscle may be conceptualized as driven by a set of motor neuron units that innervate the muscle and relate to muscle strength. The muscle may be modeled as a set of such motor units where recruitment threshold, firing rate and twitch force of the units are related. As force is generated the neurons are recruited by an orderly activation of a potential spike noise train with a variable firing rate. An activation function determines how many units are recruited and their mean firing rate for a particular excitation force. For each motor unit recruited, a spike train with a Gaussian inter-spike interval distribution is generated and each spike causes a muscle twitch, with the total muscle force being the sum of all the twitches in all the recruited motor units for a given force trace. The firing rate is a function of the activation and the recruitment threshold for the unit; the coefficient of variation of the inter-spike interval is fixed for the individual. In this simulation the muscle model is determined by the number of motor units with the maximum voluntary force for the muscle related to the number of motor units, and to the range of recruitment thresholds. The simulation method depends upon the design of the pre-processor 201 (FIG. 2), where in one configuration, the muscle activation traces and model parameters are determined for muscle sources from electromyograms positioned over the sites. In a further embodiment, the invention may use statistics collected over the sampling interval to model the muscle artifact potentials.

Figure 10:
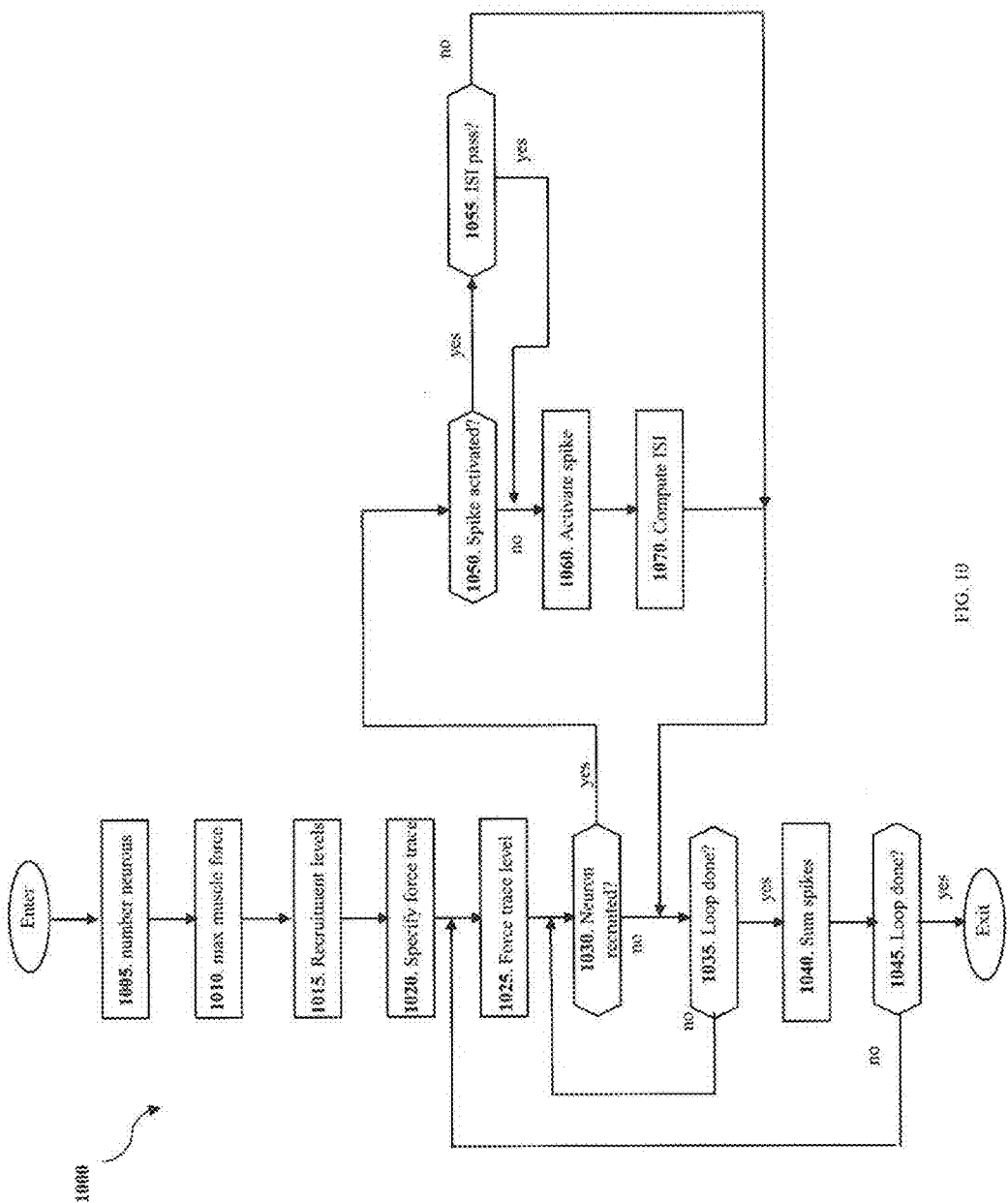
FIG. 10 is a flow chart of invention process for simulating muscle-train noise potential.

Following this reasoning, the simulation routine 1000 (FIG. 10) specifies the number of motor units 1005 in the motoneuron pool and then computes the corresponding maximum muscle force 1010 as an upper bound and the recruitment threshold 1015 for each of the neurons in the pool. Specifying an excitation force time trace 1020 specific to the muscle application, the neurons recruited for each force trace time 1025 are computed along with the activated motor spikes 1050, which summed together 1040 form the potential spike train 1035 for the force time trace. Recruiting a neuron causes a potential spike to be released 1060; the corresponding inter-spike interval 1070 and the time for the next spike are computed for reference. A spike is released 1050 once that time is passed, and the process is repeated 1045 until the force trace is less than the recruiting threshold. Table 2 lists the relations used in the simulation: the normalized recruitment threshold (th) for the ith motoneuron as a function of the recruitment range (RR) and the number of neurons in the pool (nm), where the recruitment range is expressed in percent of maximum voluntary extension, normalized to 100% full range; the mean firing rate (fr) as a function of the recruitment threshold (th) and excitation force trace level (ft), both normalized ($0<th<1$; $0<ft<1$), with the maximum threshold from 0.65 to 1.0 depending on the muscle; and the interspike interval (ISI) which is a Gaussian normal distribution about the mean given by the inverse of the mean firing rate, where the interspike interval coefficient of variance (cv) relating the mean interval to the deviation is constant with the value (0.2 to 0.6) depending upon the individual.

Considering again FIG. 1, the outputs of the source signal generators 140 and of the artifact signal generators 150 are the respective signal voltages at each site for each sample time, and these outputs as inputs to the scalp signal generator 160, are added together by the generator to simulate the net signal voltage at the sites for that time. The comparator 170 then compares the simulated signal to the raw encephalograms collected by the EEG sampler 180 from the scalp sites. In one embodiment, the comparison is done for each site at each sample time, and the scalp surface electrode montage is the template for the comparison. Note that the generator needs to reference the simulated signals in the same manner used with the EEG collection system and in the same montage configuration. Considering now the scalp surface electrodes, the 10-20 electrode system or extensions thereof are commonly used for locating electrode placement on the scalp for EEG recordings.

Figure 11:
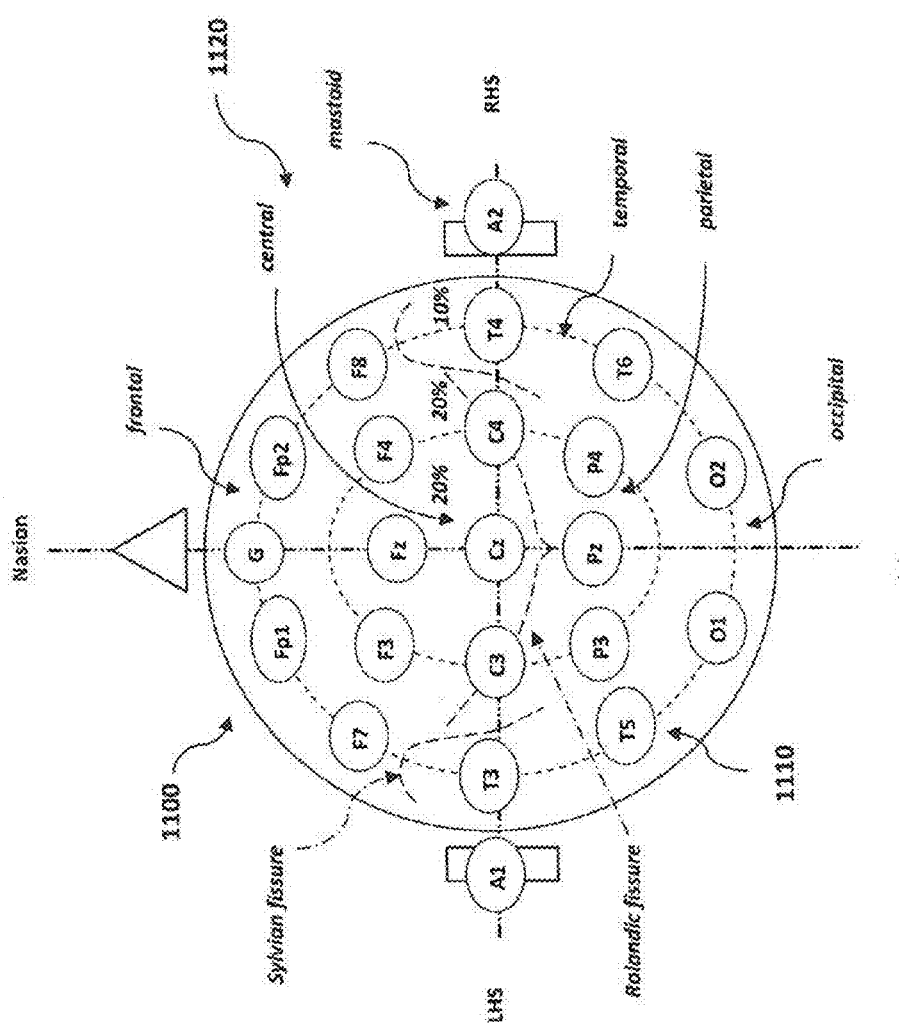
FIG. 11 is a schematic of an electrode site reference configuration for sample comparison.

For reference, FIG. 11 is a schematic of a single plane projection of the human scalp showing the nineteen electrode sites of the International 10-20 electrode system 1100 and the Rolandic and Sylvian fissures of the underlying brain for reference, with the projection to the level of the Nasion at the front of the skull and the Inion at the back. In this electrode system, the sites are located in the sagittal plane at 20% intervals along the scalp mid-line Nasion to Inion distance, with the frontal site a distance of 10% from the Nasion; and located in the coronal plane at 20% intervals along the scalp between points just anterior to the tragus of each ear, with the most lateral site a distance of 10% from the tragus. The most forward and lateral sites define a horizontal plane for reference in electrode placement. The sites are labeled 1110 by letters corresponding to the underlying cortical lobe structure 1120, such as: frontal, temporal, central, parietal, and occipital; and by number corresponding to distance from the horizontal plane, with the even numbers on the right side of the head (RHS), and the odd numbers on the left side (LHS). The sites A1 and A2 are for mastoid references used in unipolar electrode montages. A site labeled 'G' may be used for the amplifier ground in the EEG collection system. EEG recording caps (not shown) of elastic lightweight fabric that fit over the head are available with electrodes and shielded recording wires for electrode placement in both standard montages and higher density electrode configurations, with scalp site preparation and conducting gel inserted at the electrode sites after fitting. The electrodes may be combined in different montages for recording purposes depending upon the purpose of the EEG study. In bipolar recordings, the electrodes are linked in pairs to the two inputs of differential amplifiers and the recordings are the voltage differences between the pairs. In unipolar (referential) recordings, the electrodes are linked to one input of the associated differential amplifiers and the other input of all amplifiers are linked to a separate reference electrode, either one of the mastoid sites (or the ear lobes) or the average of the two, or a separate site on the scalp or in some cases, the face or body; the recordings are of the voltage differences between the exploratory scalp electrodes and that of the reference. In a further development, the recordings may be added or subtracted in different combinations for a change in reference voltage and bipolar or unipolar configurations depending upon the focus of the study.

Figure 12B:
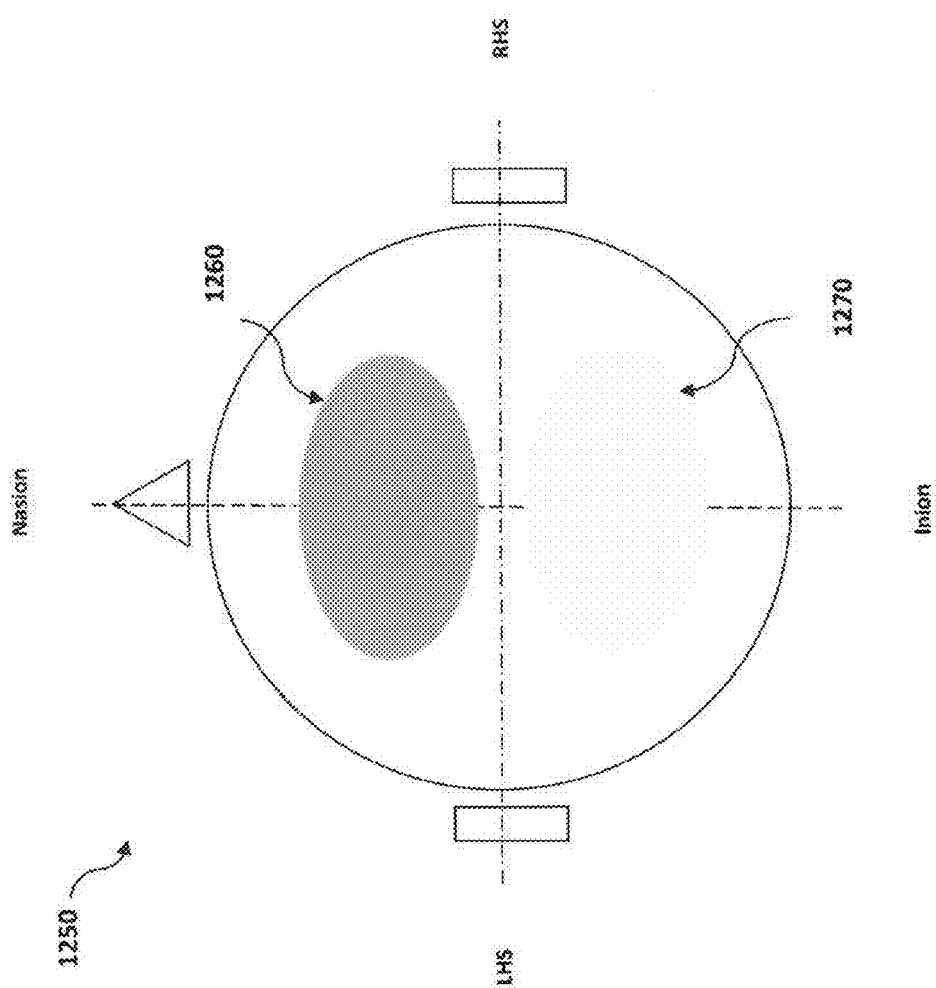
FIG. 12b is a schematic of sample comparison process results for neural source mismatch.

Various methods may be used for comparison depending upon the embodiment. For example, the site statistics over the sample period may be computed for the average and standard deviation of the site signal differences. In a further embodiment, the statistics may be for the site signal power spectrum differences, and still further, such for frequency bands of interest in a head skull topological plot. Such plots may be used by the comparator 170 (FIG. 1), for refinement of the simulation depending upon the location and amplitude of the differences. For example, FIG. 12a is a schematic of a head skull topological power spectrum plot 1200 showing a predominance of positive power difference behind the frontal eye orbits 1210 with a peak (light gray) directly behind the eyes, suggesting that the eye-movement model needs to be refined. Similarly, a predominance of a positive spectrum difference (light gray) is shown in the region for the left head muscle 1220 and a negative spectrum difference (dark gray)

for right 1230 head muscles. Further, FIG. 12b is a schematic of a head skull topological power spectrum plot 1250 showing no difference in artifacts, but a difference distributed over the scalp varying from a negative (dark gray) anterior distribution 1260 and a counterbalancing positive (light gray) posterior distribution 1270, suggesting refinement in source spectrum, location or orientation. These distributions may be by different measurements such as spectrum band peak amplitude or band power content, among others.

Demonstration for Case Studies

The methods of the invention has been applied to determine the effectiveness of several standard neurophysiological data processing and analysis techniques of the prior art, where the determination was made for a range of artifact settings in the simulation. These applications include: (1) the effectiveness of a set of artifact rejection routines used with EEGLAB for analysis of EEG (http://sccn.ucsd.edu/eeglah), with the routines used to isolate EEG segments with artifacts from the data set, where the effectiveness is determined from the scalp potentials for the remaining data set as a function of the rejection settings; (2) the effectiveness of an independent-component analysis for isolating artifact sources from the component sources after the artifact rejection process has been applied, where the effectiveness is determined from the signals at the scalp sites that are projected back from the component sources that remain; and (3) the effect of the data-collection reference electrode placement on the accuracy of the back projection after artifact rejection and an independent component analysis. In these applications, the effectiveness is determined by the fit of the scalp site potential following treatment for the data-base with the artifacts to that for the data-base without the artifacts, where the fit is measured relative to threshold statistics (see FIG. 2; Napflin, Wildi, Sarnthein (2007). "Test-retest reliability of resting EEG spectra validates a statistical signature of persons", *Clinical Neurophysiology*, 118, 2519-2524 (http://sccn.ucsd.edu/papers/napflin_EEGretest_clinph2007.pdf)), for an expected variation in scalp potentials from cortical sources alone. The advantages of the invention over the prior art was demonstrated by a comparison of the approaches showing that unlike the prior art with results difficult to interpret, application of the invention with use of a ground truth reference for the cortical signal results in a precise determination of the limitations of the treatment techniques.

It is noted that many of the results are presented herein as scalp topology of signal potentials that were originally color-scaled with 'red' being maximum potential and 'blue' minimal potential; in keeping with standard practice, these figures have been submitted in the application in gray-scale with the result that both red-colored and blue-colored potentials appear as dark gray and intermediate potentials as light gray, and for that reason extensive labeling of the figures are used to differentiate the difference.

Effectiveness of EEGLAB Artifact Rejection Techniques

Purpose:

Estimate validity of EEGLAB artifact rejection routines applied to electroencephalograms (EEG) time series for isolation of cortical sources by use of power spectrum density (PSD) analysis.

Method:

Apply artifact rejection techniques to a simulated data base generated from known artificial cortical sources and superimposed eye-movements, blinks, and muscle movements; and compare the isolated source signal following application of the rejection techniques to the original as a 'ground-truth reference' for degree of validity.

Source Configurations:

Point sources located at scalp electrode sites for a spherical shell head, with the point sources constituting the electrode site measurements that would occur without artifacts. The sources are modeled as an autoregressive filter process driven by white noise, where the filter coefficients are derived for the spectrum of the source as a set of oscillators with strong alpha band power centered at 10 Hz.

Site Configuration:

The electrode scalp sites correspond to the 10-20 electrode system composed of 19-electrode channels, and a left and right EOG configuration. In this study, all sites are activated by the same source spectrum.

Artifact Generation:

Artifacts are simulated using mathematical models for the different artifact sources of muscle movements, and eye-movements and blinks; the source potential at the electrode sites is weighted by the scalp topology separation distance.

Figure 13:
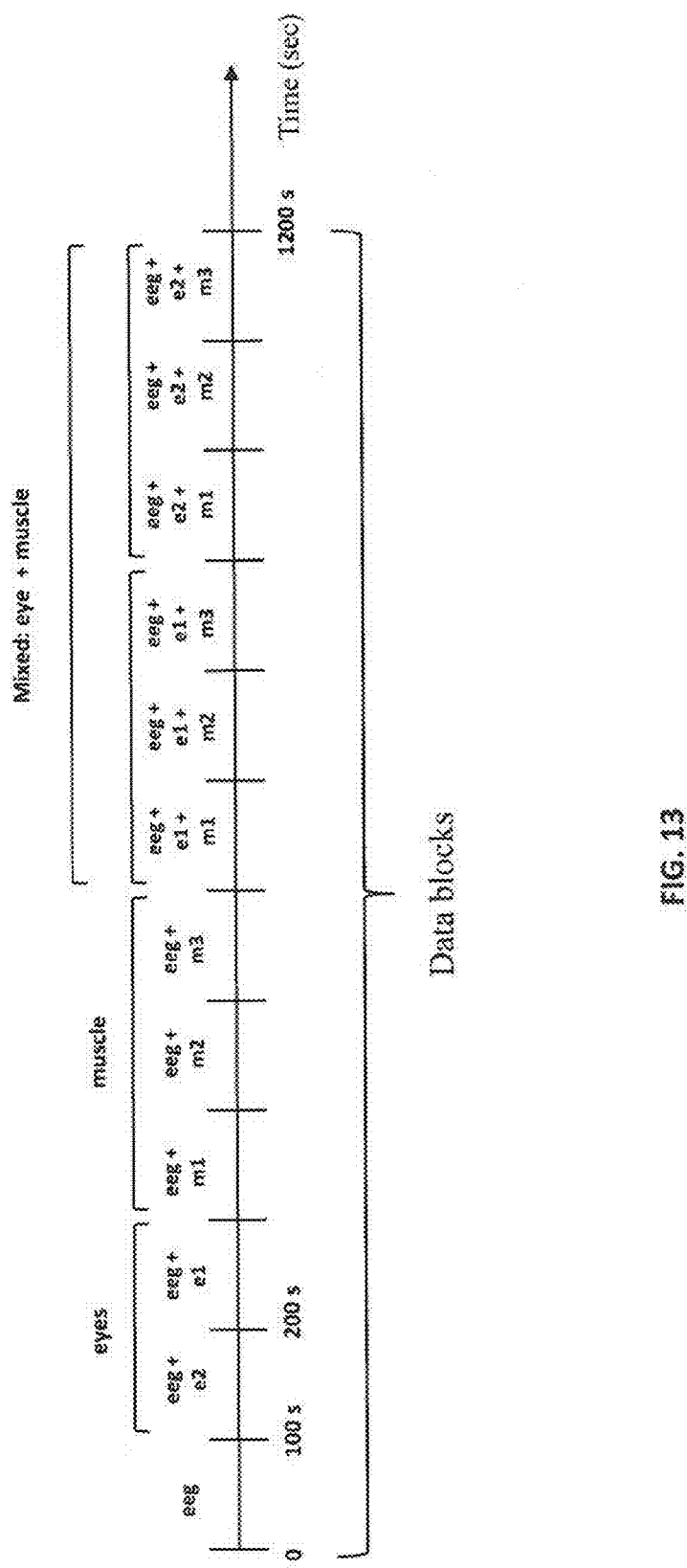
FIG. 13 shows a simulation data set format showing artifact blocks.

Data Base Format:

The database is composed of 20-minutes of 21-channel (19 sites, 2 EOG sites) data sampled at 256 Hz; the data is in 12 blocks each 100-seconds, where the blocks are combinations of the artificial source signal, the EOG (two levels), and the EMG (3-levels), with the source signal occurring in all blocks (FIG. 13), and with the addition of an event file of time-locked events occurring at 0.5 sec intervals for epoching the data base where appropriate. The absolute maximum source amplitude was set to about 20 uV, under program control. Block 1 containing source signal without artifacts constituted about 8.3% of the data; however, the eye movements and blinks only occurred occasionally in the corresponding blocks, and the muscle artifacts build up and decrease according to a half-sinusoidal envelope (simulating slow head rotation and back). The result is that all blocks have portions with true source signals.

Artifact Rejection Process:

A standard EEGLAB analysis process (http://sccn.ucsd.edu/eeglab) prepared the data base for application of epoch rejection using software commands as follows:

'Edit/select data': The scalp site channels 1-19 were selected for analysis;

'Tools/Remove baseline': The baseline is removed from all channels;

'Tools/Filter the data/Basic FIR filter': All channels were digitally band pass filtered with a 50-Hz low-pass filter, and then a 1-Hz high-pass filter;

'Tools/Extract epochs': Epoch selection (0-0.5 s), epoch baseline removal (0 0);

Each of the EEGLAB epoch rejection techniques were then applied in turn to the resulting data base for a range of settings for epoch rejection by amplitude (+/−[10:5:45] uV), slope (+/−[5:5:40] uV/epoch, at Rc=0.3), abnormal probability and kurtosis ([1:1:8]%; [1:1:8]%), and abnormal spectrum (+/−[15:5:50] dB). In all cases, the range of settings was selected to reject all to none of the data base as much as possible.

Study Statistics: The study statistics are based on a sample from the literature of resting EEG for alert subjects with eyes closed (see FIG. 2; Napflin, Wildi, Sarnthein (2007). "Test-retest reliability of resting EEG spectra validates a statistical signature of persons", *Clinical Neurophysiology*, 118, 2519-2524; [(http://sccn.ucsd.edu/papers/napflin_EEGretest_clinph2007.pdf)]), for which the peak power and peak frequency were normally distributed, following decibel logarithmic transformation of the power spectrum ($10*\log_{10}$ [uV$^2$/Hz]). For a sample size of 75, the mean and standard deviation reported for the transformed peak power are: 11.7+/−7.0 dB, and for the peak power frequency: 9.7+/−1.1 Hz. On this basis, the standard error 95% Confidence Interval for the study spectrum peak amplitude taken as a mean is: CI=+/−1.40 uV$^2$/Hz, and that for the peak amplitude frequency is: CI=+/−0.25 Hz.

Study Process: The spectrums of the source isolated at electrode site Cz are computed for each technique by the rejection settings, using the power-spectral-density (PSD) representation of the signal (Matlab 'Aryule.m' function); the originating source spectrum is assumed a ground truth reference since the source is simulated by a specified autoregressive process.

Study Results

Figure 14A:
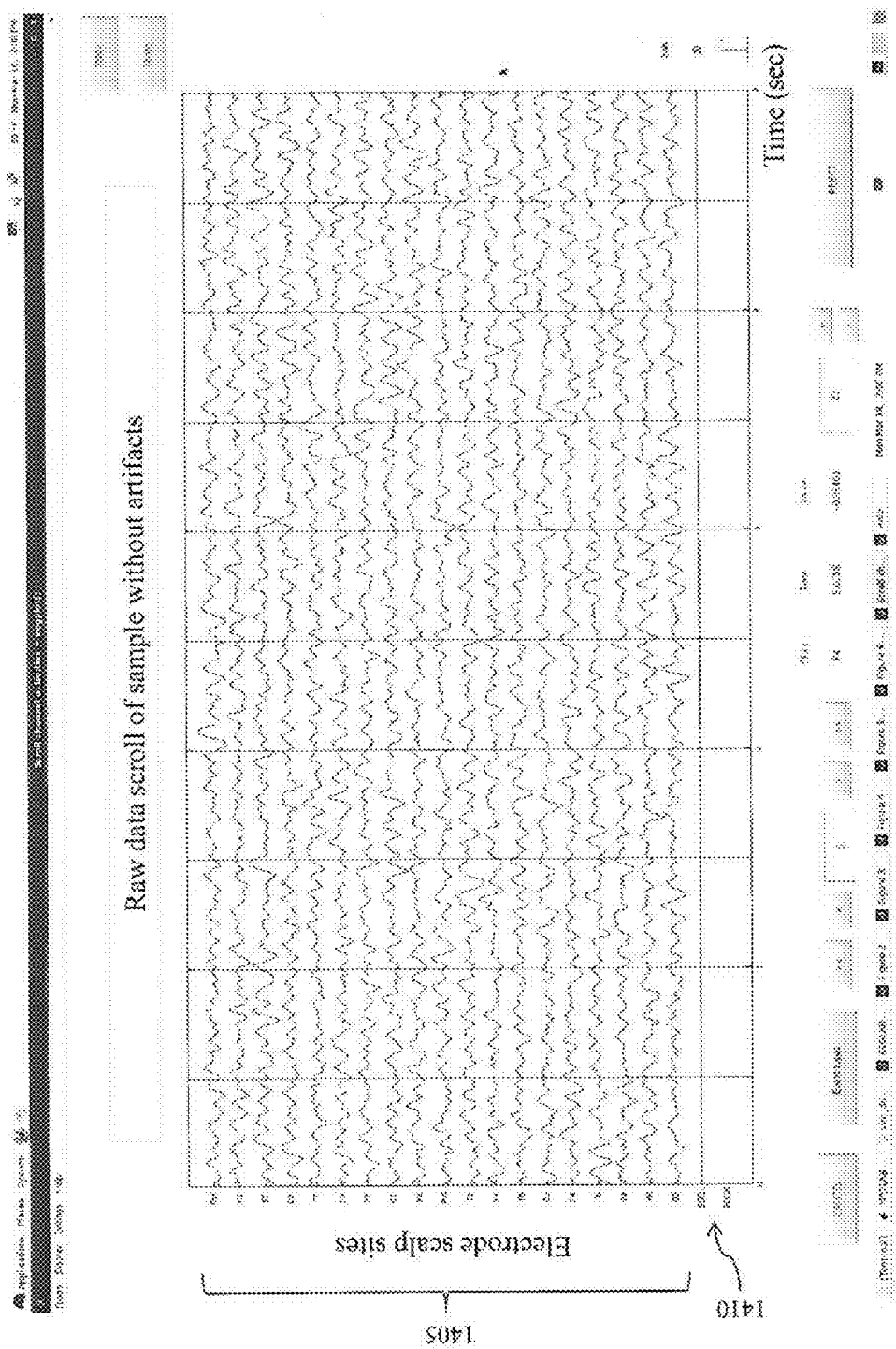
FIG. 14a shows simulated raw data scroll scalp site voltage sample without artifacts.
Figure 14B:
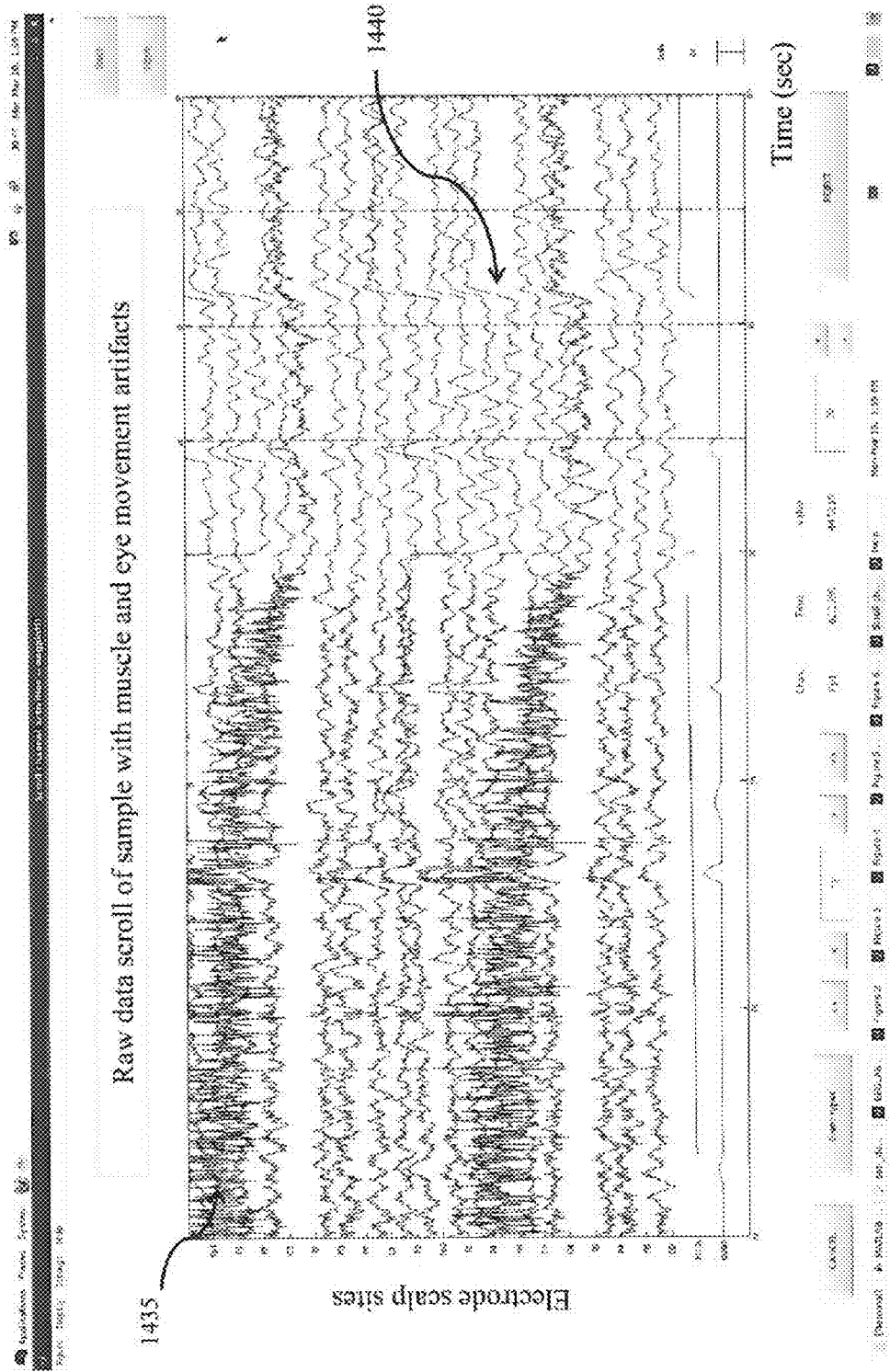
FIG. 14b shows simulated raw data scroll scalp site voltage sample with muscle and eye-movement artifacts.
Figure 14C:
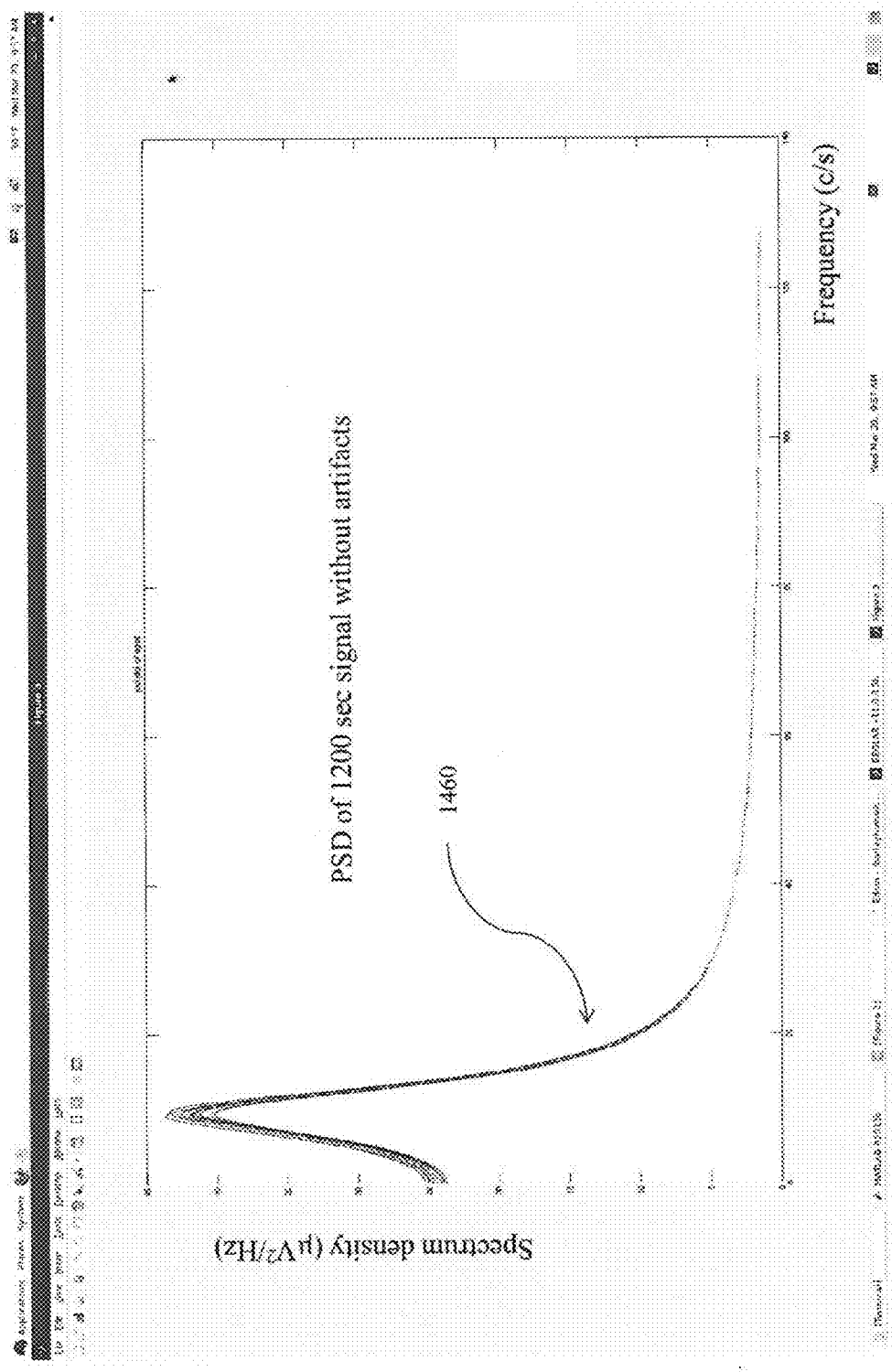
FIG. 14c is a power spectrum density plot of scalp site (Cz) signal without artifacts.

Simulation Waveforms:

The EEG simulation process produces a reasonable database for analysis as seen from the figures. FIG. 14a shows sample data time-line signal scrolls for the 19-sites 1405 (and two EOG sites 1406), for a five second portion of the database without artifacts (Block-1), and FIG. 14b for a portion with overlaid muscle 1435 and eye-movement 1440 artifacts (Block 11 & 12). The figures show seemingly realistic traces for EEG both with and without contaminations suggesting a reasonable simulation for analysis.

Data Sample Size:

The 1200 sec sample is a suitable data sample size for analysis. FIG. 15 shows power spectrum density (PSD) plots in uV$^2$/Hz (0-45) vs. Hz (0-140), of the source signal without artifacts for the 120 s blocks of the 1200 sec sample, with all block spectrums overlaid 1460. The plots show that the spectrums are practically the same with only a minor separation at the 10-Hz peak, implying source signal stability over the data set.

Artifact Rejection Techniques:

The results are summarized in bar-plots of the amplitude of the spectral peaks for the PSD of the treated data plotted by rejection setting, along with the peak amplitude for the ground-truth source with 95% CI bounds. The major spectral peaks are roughly at 10 Hz in agreement with that for the ground-truth source, a minor peak occurs at about 40 Hz for most of the plots, and at higher settings, a peak occurs at about 27 Hz for some techniques.

Figure 15A:
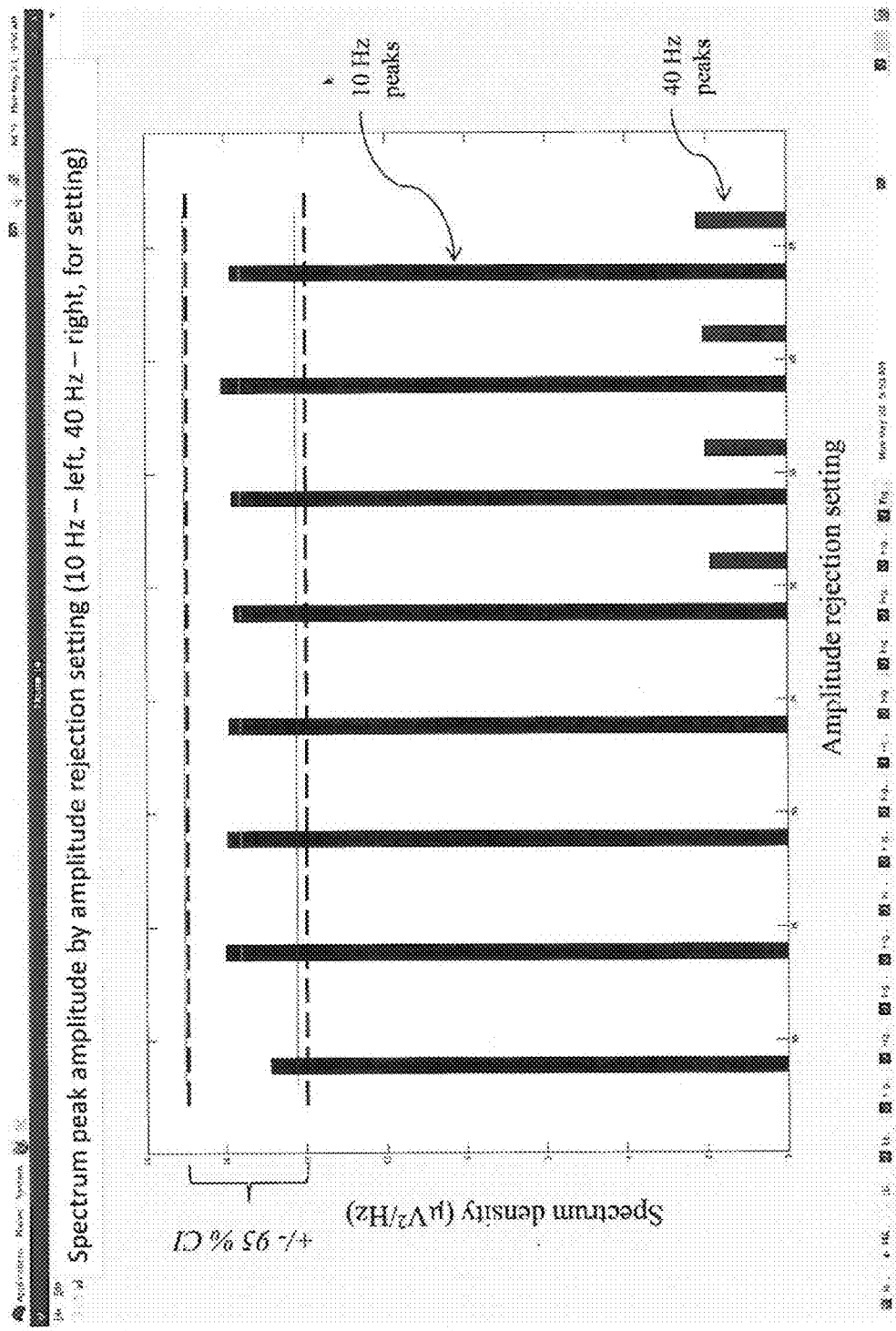
FIG. 15a shows spectrum peak amplitude of scalp site by signal amplitude rejection setting.

Abnormal Amplitude:

The bar-plots of FIG. 15a show that the major peak amplitude (at 10 Hz) is stable and slightly higher than that of the source over a rejection range in signal waveform amplitude of 10 to 45+/−uV, with a corresponding rejection from 70% to 30% of the data; the higher the setting, less data is rejected. The EEGLAB manual recommended setting of +/−25 uV is within this range. Spectral plots are mainly in agreement with the source spectrum, with however the plot for the low setting (with most data rejected), is lower in peak amplitude while those for higher settings are close to that for the source as shown by the +/−95% confidence interval about the true value 10 Hz peak amplitude. A secondary peak at about 40 Hz appears at higher settings, and increases in amplitude with increased setting.

Figure 15B:
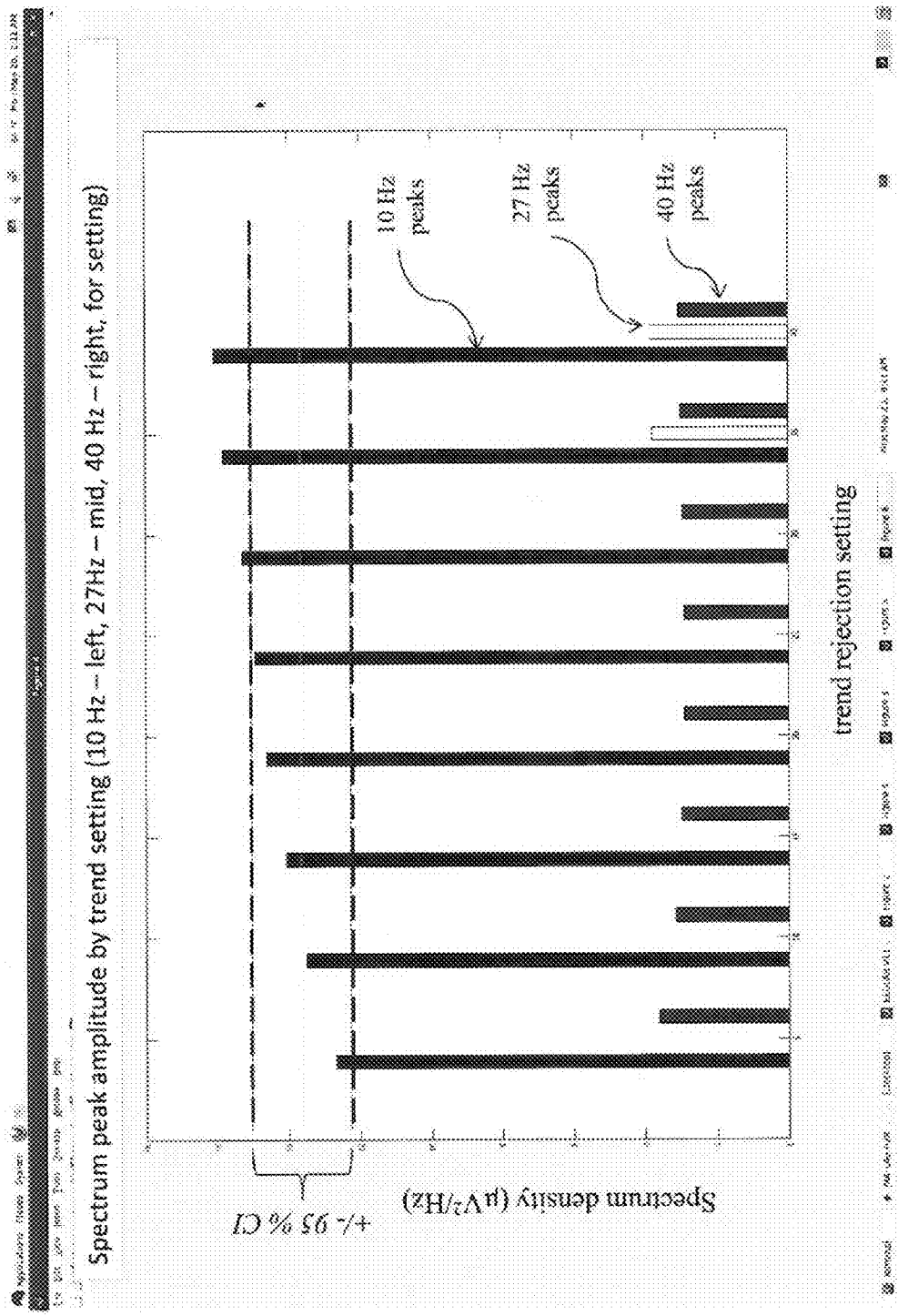
FIG. 15b shows spectrum peak amplitude of scalp site by signal trend rejection setting.

Abnormal Trend:

The bar-plots of FIG. 15b show a continual rise in the major peak amplitude about that of the source overt a rejection range in signal waveform slope of 5 to 40+/−uV/epoch (Rc=0.3), with a corresponding decrease in data rejection. A secondary peak occurs at 40 Hz, while a tertiary peak at appears at 27 Hz for settings above +/−30 uV/epoch. The spectral plots show a spread of peak amplitude about that of the source, and distortions at the low frequencies and higher frequencies, as shown by the +/−95% confidence interval about the true value 10 Hz peak amplitude.

Figure 15C:
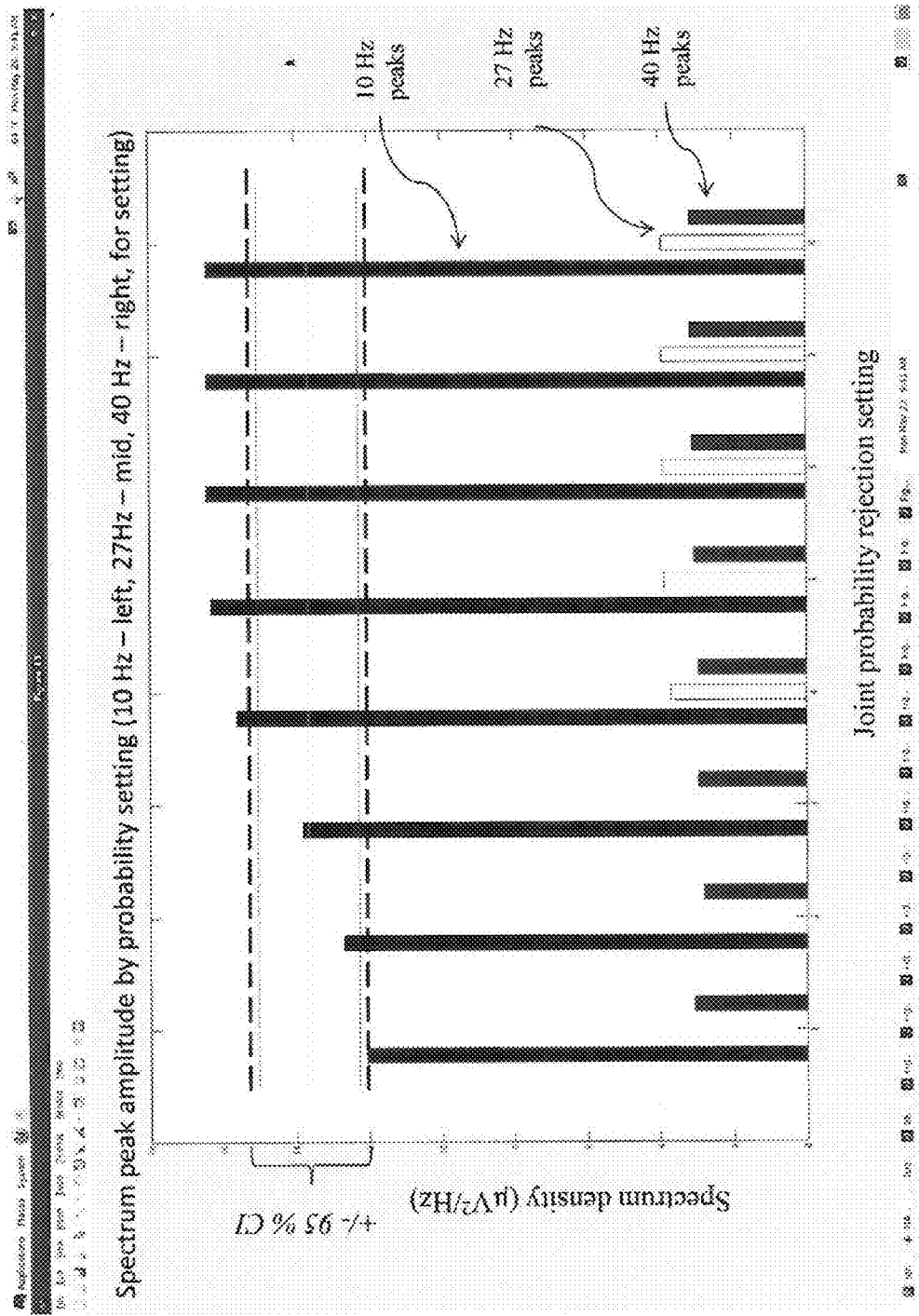
FIG. 15c shows spectrum peak amplitude of scalp site by signal joint probability rejection setting.

Abnormal Joint Probability:

The bar-plots of FIG. 15c for rejection settings from %1 to 8%, show that the major peak amplitude is displaced but mainly stable over the low end of the setting range of 1% to 2%, with a corresponding data reduction of roughly 30 to 95%, but shows a continual increase in amplitude with intermediate settings; this rise is steepest in the 2% to 6% range (30% to 3% data reduction), which includes the EEGLAB manual recommended 5%. A secondary peak occurs at about 40 Hz, and a tertiary peak appears at 27 Hz for the higher settings. The spectral plots show a spread of peak amplitude about that of the source, and distortions at the low frequencies and higher frequencies, as shown by the +/−95% confidence interval about the true value 10 Hz peak amplitude.

Figure 15D:
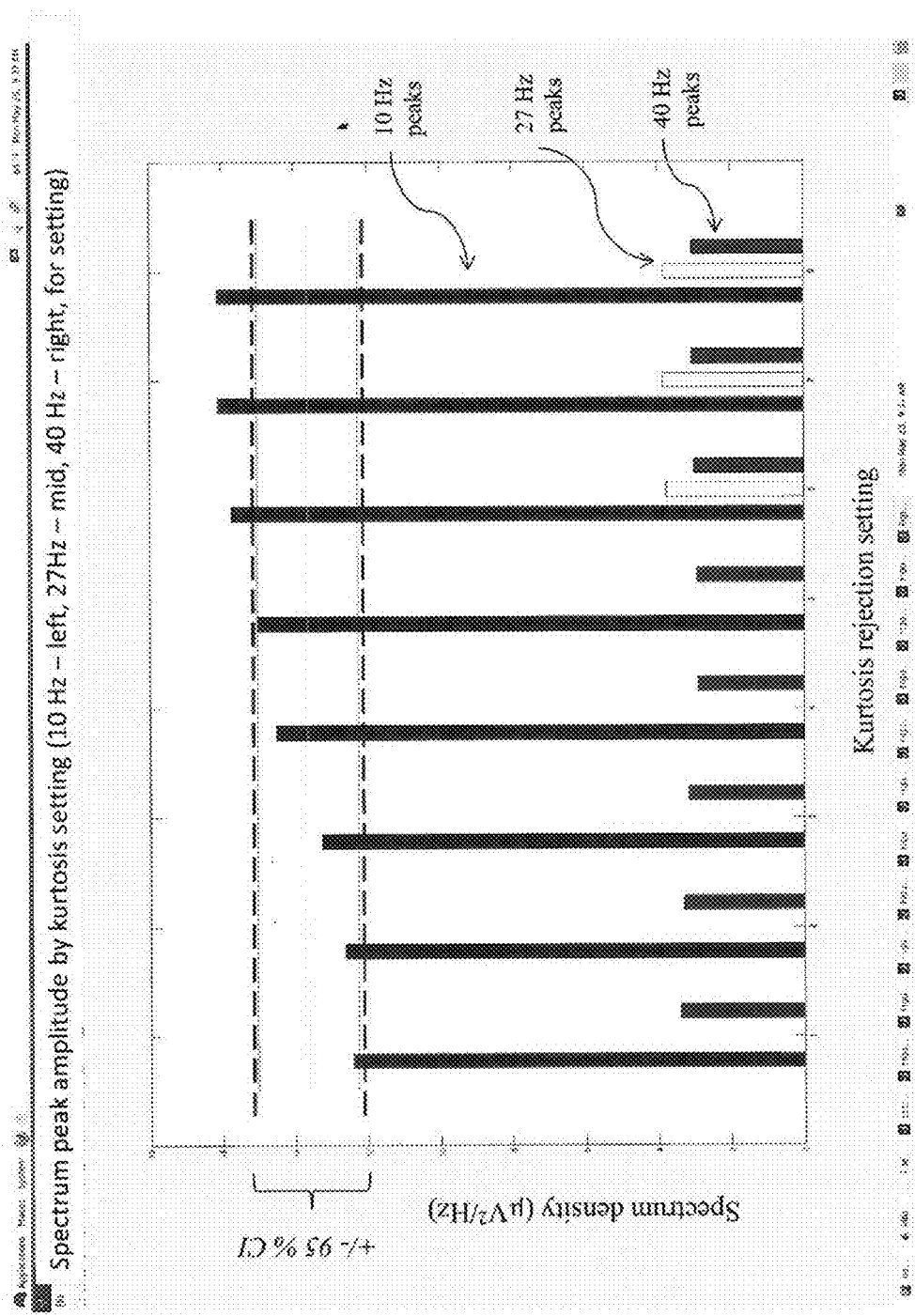
FIG. 15d shows spectrum peak amplitude of scalp site by signal kurtosis rejection setting.

Abnormal Kurtosis:

As with the Joint Probability method, the bar-plots of FIG. 15d for rejection settings from 1% to 8%, show that the major peak amplitude is displaced but mainly stable over the low end of the setting range of 1% to 2%, with a corresponding data reduction of roughly 30 to 95%, but shows a continual increase in amplitude with setting for higher settings; this rise is steepest in the 4% to 6% range (3% to 7% data reduction), which includes the EEGLAB manual recommended 5%. A secondary peak occurs at about 40 Hz, and a tertiary peak appears at 27 Hz for the higher settings. The spectral plots show a spread of peak amplitude about that of the source, and distortions at the low frequencies and higher frequencies, as shown by the +/−95% confidence interval about the true value 10 Hz peak amplitude.

Figure 15E:
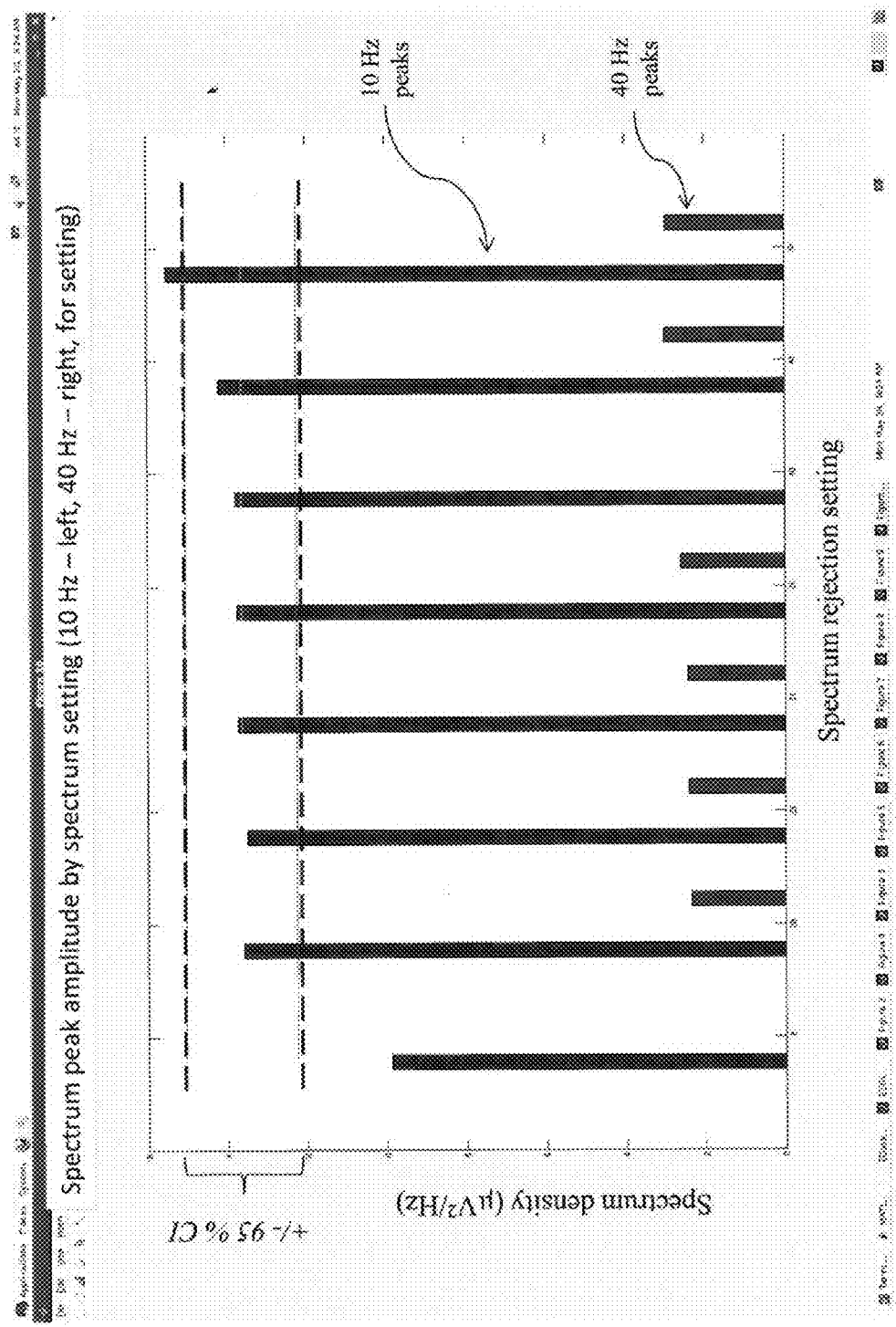
FIG. 15e shows spectrum peak amplitude of scalp site by signal spectrum rejection setting.

Abnormal Spectrum:

The bar-plots of FIG. 15e for a rejection range of 15 to 40+/−dB, show show that the major peak amplitude is stable and about equal to that of the source over the rejection range of 20 to 40+/−dB, with a corresponding rejection from about 90% to 40% of the data; the higher the setting, less data is rejected. A secondary peak at the 40 Hz is present as well. The EEGLAB manual recommended setting of +/−25 dB is within this range. The spectral plots are in mainly in agreement with the source spectral, with however the plot for the low setting (with most data rejected), severely distorted, those in the mid-range in close agreement, and those for the highest settings in higher amplitude that for the source, as shown by the +/−95% confidence interval about the true value 10 Hz peak amplitude.

Summary:

Of the artifact rejection techniques studied, the abnormal spectrum rejection was the most effective resulting in an accurate reproduction of the source signal following parameterization, over a wide range of settings. For pre-processing with the spectrum method, the major peak amplitude of the signal isolated by the analysis results is closely equal to that of the source over a wide range of rejection settings except at the range ends. Essentially, the spectra fit is close for the mid-range of settings, but decreases for low settings in which a large amount of data is removed either because there is too little data or because the remaining signal are not representative, and decreases at high settings for which little data is removed and artifacts remain. Similar comments apply to the abnormal amplitude method with however the spectral fit not being as close. The joint probability and kurtosis methods have a similar effect of a relatively stable fit with a bias offset over the lower setting ranges of 1 to 2%, with a larger amount of data rejected, but a trending offset to the fit for higher settings. The abnormal trend technique following band-pass filtering was largely ineffective. All techniques lead to distortions in the signal spectra, resulting in additional minor peaks at higher frequencies for the higher settings. Apparently, the distortions are influenced by the artifacts rejection, which implies that the signal results from data preprocessed at different settings may not be properly comparable for statistical analysis.

Effects of Epoch Size, Electrode Site Location, and Artifact Intensity and Quantity Purpose:

Estimate the effects of epoch Size, electrode Site Location, and artifact intensity and quantity on the validity of EEGLAB artifact rejection routines applied to electroencephalograms (EEG) time series for isolation of cortical sources by use of power spectrum density (PSD) analysis.

Method:

Apply artifact rejection techniques to a simulated data base generated from known artificial cortical sources and superimposed eye-movements, blinks, and muscle movements; and compare the isolated source signal following application of the rejection techniques to the original as a 'ground-truth reference' for degree of validity.

Figure 16A:
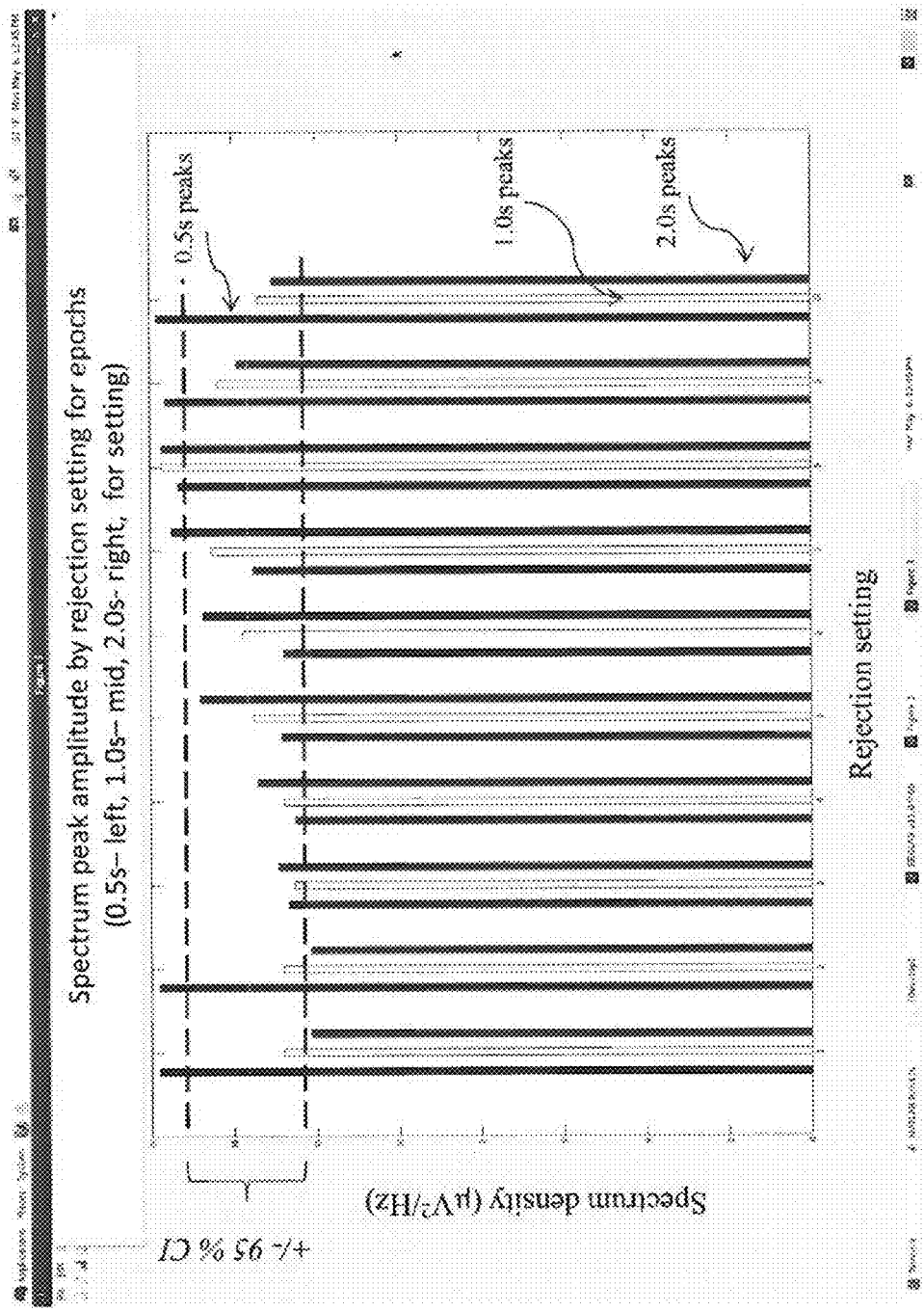
FIG. 16a shows spectrum peak amplitude of scalp site by rejection setting for epochs.

Study Results:

Effect of Epoch Size:

The effectiveness of the artifact rejection techniques is apparently influenced by the epoch size. These results follow a study in which the rejection techniques were applied in combination together sequentially over a range of settings for epoch sizes of 0.5 sec, 1.0 sec, and 2.0 sec, with the settings varied together for the amplitude, trend, and spectrum over the range [10:10:140], and the joint probability and kurtosis over [1:1:10]. FIG. 16a shows the peak amplitude of the PSD spectral of the isolated source for the three epoch sizes (left to right: 0.5 s, 1.0 s, 2.0 s), as a function of the setting increment. The figure shows a consistent increase in peak amplitude but different values by epoch size with setting increment over the middle range. While the peak amplitude for the larger epoch sizes are less than that for the true source at the lower range, that for 0.5 s size is originally much larger. Similarly, spectral plots show that the peak amplitude frequency for the three epoch sizes is a function of the setting increment. Here, while the frequencies are near that of the true source near the middle range, the frequencies for the larger epochs are less while that for the 0.5 s is larger, and all are less at the higher setting range, as shown by the +/−95% confidence interval about the true value 10 Hz peak amplitude.

Figure 16B:
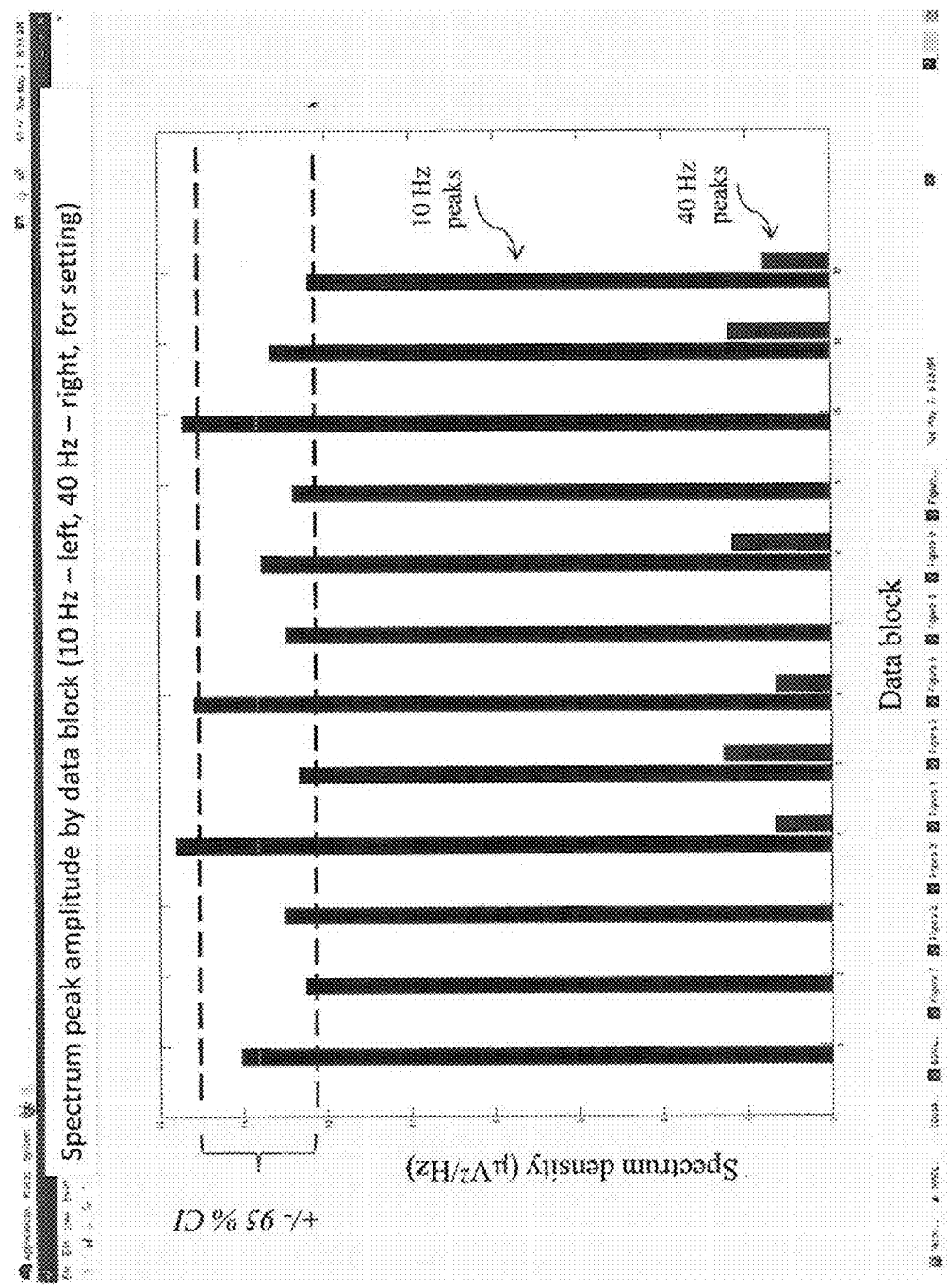
FIG. 16b shows spectrum peak amplitude of scalp site by artifact data block.
Figure 16C:
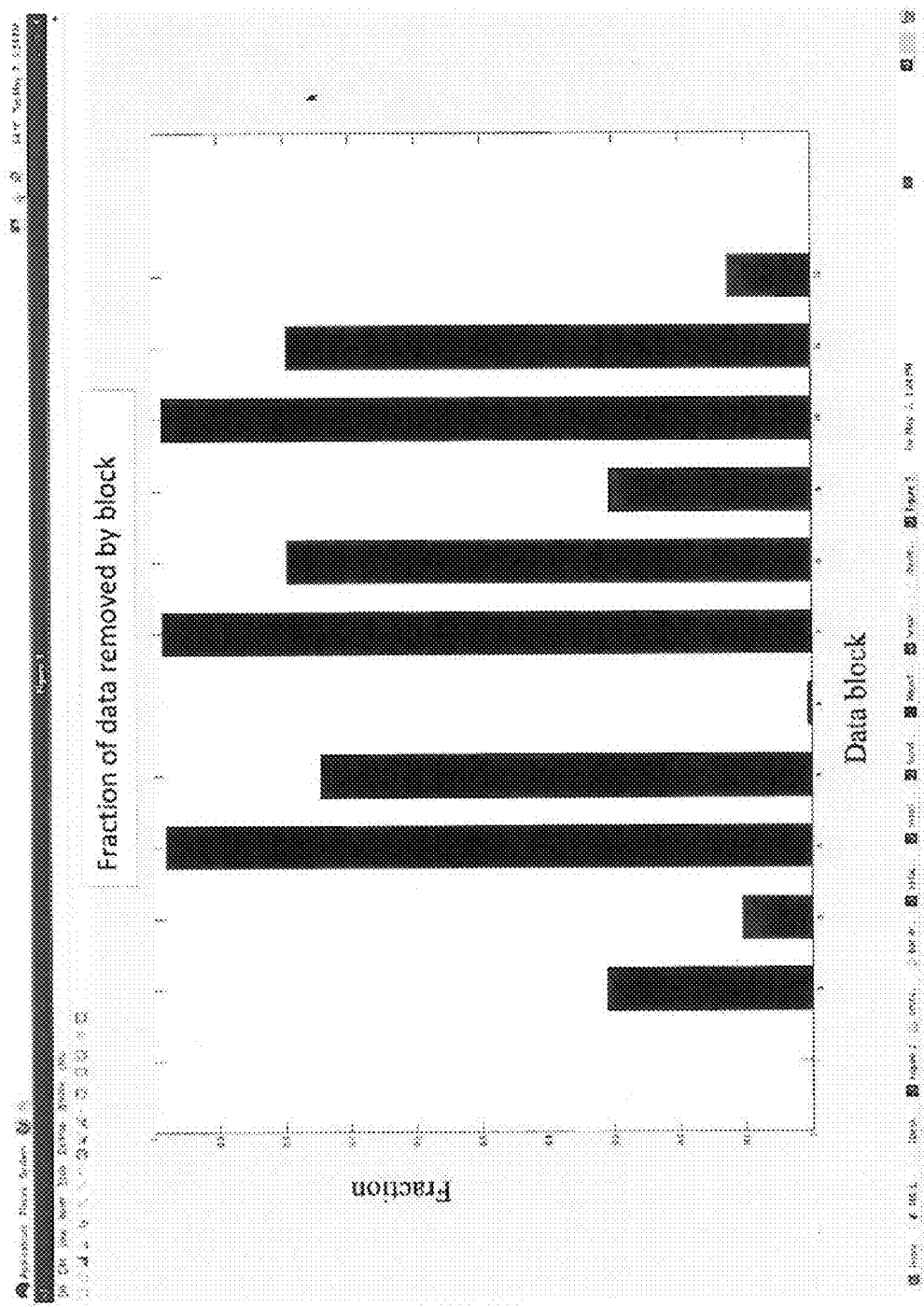
FIG. 16c shows a fraction of data removed by artifact data block.

Effect of Artifact Intensity:

The effectiveness of the artifact rejection techniques is apparently influenced by the artifact intensity. These results follow a study of the database statistics of the data blocks (1 thru 12) for which the rejection techniques were applied in combination together sequentially to the database for the 0.5 s epoch size, with the settings set at the recommended level for the amplitude, trend, and spectrum at [25;50;25], and the joint probability and kurtosis at [5;5]. FIG. 16b shows the peak amplitude of the PSD spectral of the isolated source for the Cz site computed separately for each of the data blocks 1-12 (10 Hz: left, 40 Hz: right). The blocks with embedded muscle artifacts show an additional low power in the 40 Hz range corresponding to a residual of muscle power. The blocks 4, 7, and 10 with high muscle intensity show reduced residual because of the artifact rejection; those blocks with medium intensity (5, 8, and 11) show a higher residual because of reduced rejection from the higher setting, while those with low intensity (6, 9, and 12) show low residual because of the smaller intensity, as can be seen by comparison with the +/−95% confidence interval about the true value 10 Hz peak amplitude. This interpretation is supported by FIG. 16c, which shows the fractional amount of signal removed by the rejection process by block; here, most of the data is removed for the high muscle intensity blocks (4, 7, 10), a moderate amount for the medium intensity blocks (5, 8, 11), and a marginal amount for the low intensity blocks (6, 9, 12).

Effect of Severity:

The effectiveness of the artifact rejection techniques apparently does not depend upon the amount of artifacts in the data as long as the artifact statistics remain the same and sufficient data remains after application for a proper autoregressive analysis. In this study, the results of the application of the EEGLAB techniques at the recommended settings were compared for two databases with the same artifacts but different activation periods. The two databases were of the same configuration as used in this study, but in one case 10% of the block data contained activated artifacts, while in the other, 100% of the block data did so. Artifact rejection applied to the two data bases [in succession of abnormal amplitude (setting: +/−25 uV), trend (+/−50 uV/epoch), joint probability (5%), kurtosis (5%), and spectrum (+/−25 dB) for epoch rejection], removed 31.18% of the data for the 10% activation severity, and 88.58% for the 100% severity database, leaving enough data in either case for a proper PSD analysis. A spectrum plot (not shown) indicates that the PSD plots for the Cz site following epoch removal are practically the same suggesting no effect of severity, and except for distortions in the delta and beta band region, close to the source PSD plot as well.

Figure 16D:
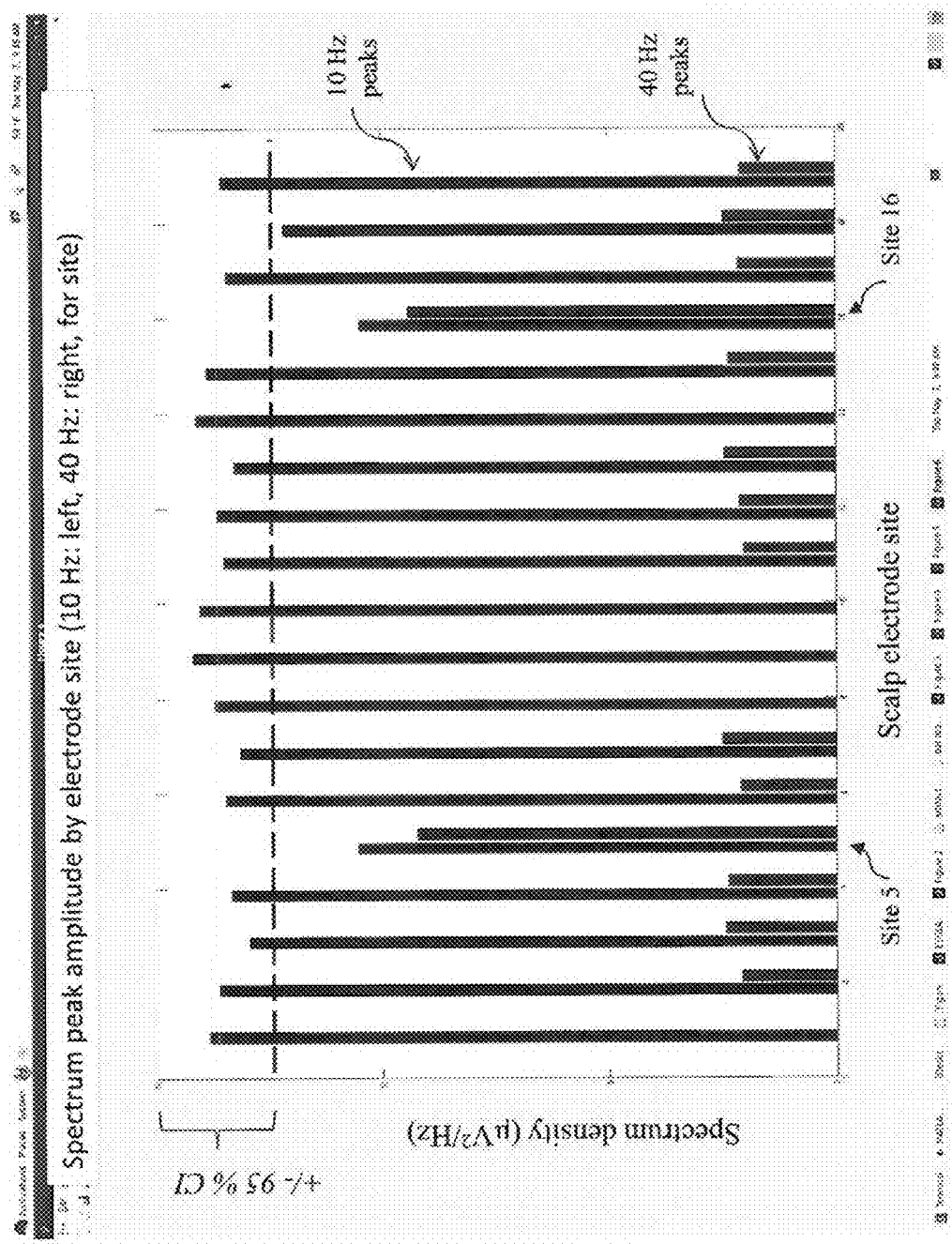
FIG. 16d shows spectrum peak amplitude by scalp electrode site.
Figure 16E:
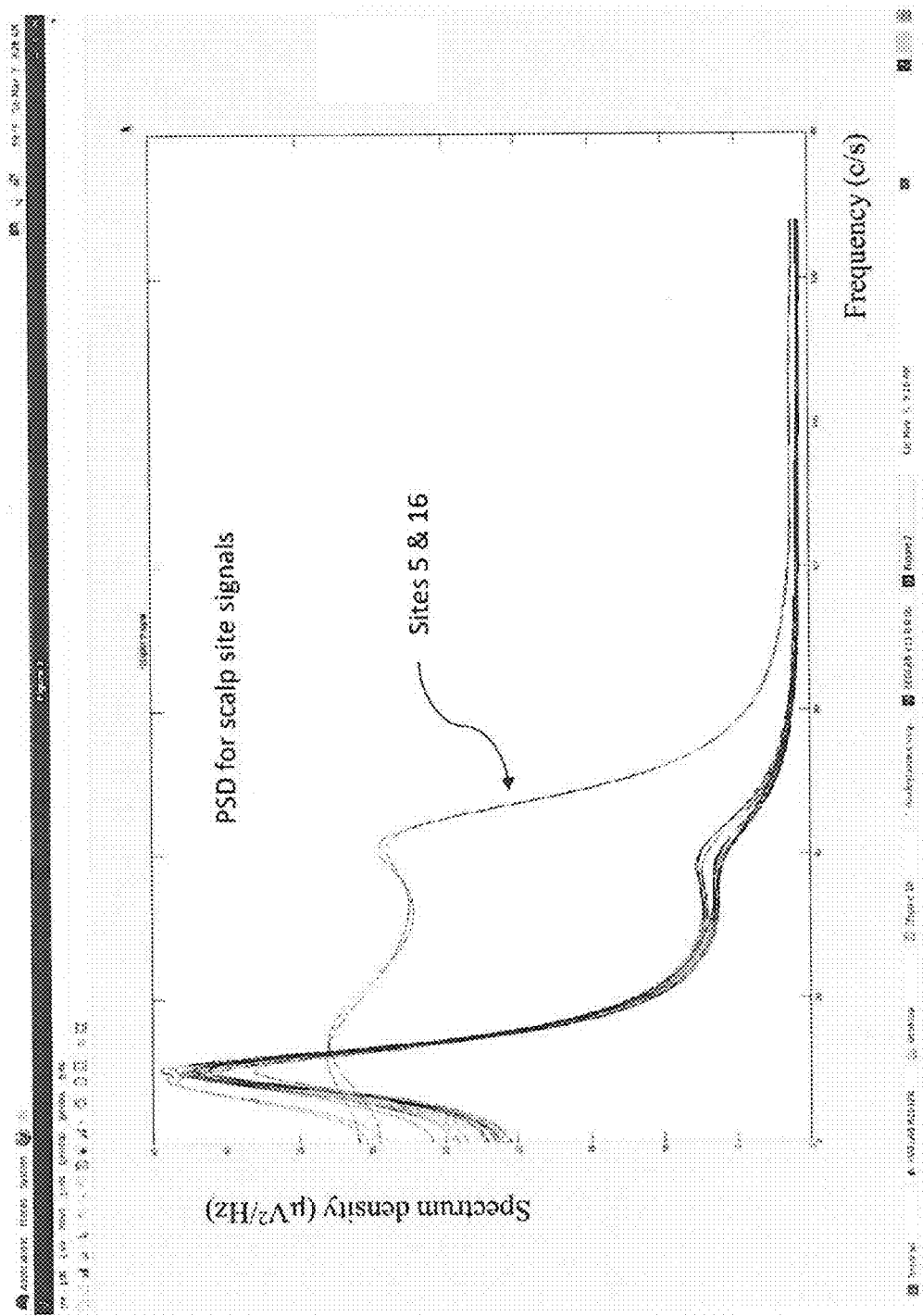
FIG. 16e is a power spectrum density plot for scalp site signals.

Effect of Site Location:

The effectiveness of the artifact rejection techniques is influenced by the site location. These results follow a study of the database for which the rejection techniques were applied in combination together sequentially to the database for the 0.5 s epoch size, with the settings set at the recommended level for the amplitude, trend, and spectrum at [25;50;25], and the joint probability and kurtosis at [5;5]. FIG. 16d shows the peak amplitude of the PSD spectral (10 Hz: left, 40 Hz: right), of the isolated source following epoch rejection for the electrode sites 1-19 numbered according to the 10-20 electrode system. The figure shows the sites about the temple regions retain some low power in the 40 Hz area due to muscle artifact retention. In particular, the T7 (site 5) and T8 (site 16) electrodes are dominated by the artifacts. The +/−95% confidence interval about the true value 10 Hz peak amplitude is shown for comparison. Similarly, FIG. 16e shows that the spectral plots for T7 (site 5) and T8 (site 16) are largely dominated by the artifact power certainly in the 20 to 60 Hz range and showing a corresponding 40 Hz amplitude peak.

Summary:

The effectiveness of the artifact rejection techniques is influenced by the epoch size, the electrode site location, and the artifact intensity, but apparently does not depend upon the amount of artifacts in the data as long as the artifact statistics remain the same and sufficient data remains after application for a proper autoregressive analysis.

Effectiveness of Independent Component Analysis

Purpose: Estimate validity of EEGLAB Independent Component Analysis applied to electroencephalograms (EEG) time series for isolation of parameterized cortical sources, by use of power spectrum density (PSD) analysis.

Method: Apply Independent Component Analysis for source isolation following artifact rejection to a simulated data base generated by known artificial cortical sources and superimposed eye-movements, blinks, and muscle movements; and compare the projected scalp site signals to those generated by the cortical sources without the artifacts.

Source Configurations:

Cortical sources are simulated dipole sources embedded in a MNI Talairach reference coordinate space with delta, theta, alpha, and beta band task specific spectral parameters of power, bandwidth, and peak amplitude. The sources are modeled as an autoregressive filter process driven by white noise, where the filter coefficients are derived for the spectrum of the source as a set of oscillators with strong alpha band power. In this study, 34 sources were used with all sources activated by the same spectrum, but random orientation.

Cortical Head Scalp Site Potentials:

Cortical potentials at the head scalp sites are generated as the sum of the potentials from the simulated cortical dipole sources transformed to four-shell spherical head model locations. The dipole source potentials are the resultant of tangential and radial dipole components computed from the source location and orientation relative to the head model spherical surface.

Site Configuration:

The electrode scalp sites correspond to the 10-20 electrode system composed of 19-electrode channels, and a left and right EOG configuration. For reference to the figures, Table 3 lists the site numbers and equivalent labels.

Artifact Generation:

Artifacts are simulated using mathematical models for the different artifact sources of muscle movements, and for eye-movements and blinks; the source potential at the electrode sites is weighted by the scalp topology separation distance.

Data Base Format:

The database is organized as in the prior studies with 12 blocks each 100-seconds, where the blocks are combinations of the artificial source signal, the EOG (two levels), and the EMG (3-levels), Block 1 containing source signal without artifacts constituted about 8.3% of the data; Blocks 2 and 3 contain ocular artifacts (high, low level movements), Blocks 4 thru 6 contain muscle artifacts (high, mid, low intensity), while Blocks 7 thru 9 contain the same with high level ocular movements, and Blocks 10 thru 12 such with low level ocular movements. Note that the eye movements and blinks occur only occasionally, and the muscle artifacts build up and decrease according to a half-sinusoidal envelope (simulating slow head rotation and back) in the corresponding blocks. The result is that all blocks have some portions with mainly true source signals.

Artifact Rejection Process:

A standard EEGLAB analysis process prepared the data base for application of the ICA using software commands as follows:

'Edit/select data': The scalp site channels 1-19 were selected for analysis;

'Tools/Remove baseline': The baseline is removed from all channels;

'Tools/Filter the data/Basic FIR filter': All channels were digitally band pass filtered with a 50-Hz low-pass filter, and then a 1-Hz high-pass filter;

'Tools/Extract epochs': Epoch selection (0-0.5 s), epoch baseline removal (0 0);

'Tools/Epoch rejection (all techniques)': the rejection techniques were applied sequentially for the 0.5 s epoch size, with the settings set at the recommended level for the amplitude (+/−25 uV), trend (+/−50 uV/epoch), and spectrum (+/−25 uV dB), and the joint probability and kurtosis (5%; 5%).

ICA Process:

The EEGLAB command 'runica.m' was applied to the resulting data set; an automated technique for component classification as signal or artifact was applied to the resulting independent component dipole set based on the IC activation spectrum (goodness of quadratic fit), spectrum peaks by number of peaks below 3 Hz (eye-movements) or above 30 Hz (muscle spectrum), and dipole location within the Talairach reference coordinate space (within sphere, behind eye-orbit regions). The automated results were reviewed using the EEGLAB routines for component scroll, spectrum, topological power distribution (2-D map), and dipole location in the Talairach representation for component removal and back projection of the component activations to the scalp sites.

Study Process:

The spectrums of the back projected signals isolated at the electrode sites are computed using the power-spectral-density (PSD) representation of the signal (Matlab 'Aryule.m' function); the originating 'true' source spectrum is assumed a ground truth reference since the source is simulated by a specified autoregressive process.

Study Features:

The number of IC's retained and the spectral content are study features, as well as the method of projecting the retained activations back to the electrode sites.

Retained Components:

While some components are obvious ocular or muscle artifacts and therefore should be removed, other components are graded combinations of source and artifact spectrums and may be ranked accordingly for removal. The automated technique and manual provided two separate sets of such components by study features.

Projection Methods:

A direct method of conditioning the retained activations for projection back to the electrode sites is compared to that using an inverted reduced matrix commonly derived by the Moore-Penrose pseudoinverse method, where the direct method sets to zero the inversion matrix weights for the rejected sources.

Study Statistics:

As in the prior studies, the study statistics are based on a sample from the literature of resting EEG for alert subjects with eyes closed (see FIG. 2; Napflin, Wildi, Sarnthein (2007). "Test-retest reliability of resting EEG spectra validates a statistical signature of persons", *Clinical Neurophysiology*, 118, 2519-2524).

Study Results:

The independent components, the scalp site projections for the true sources, and the scalp site projections for the sources by artifact category and projection method are presented.

Figure 17A:
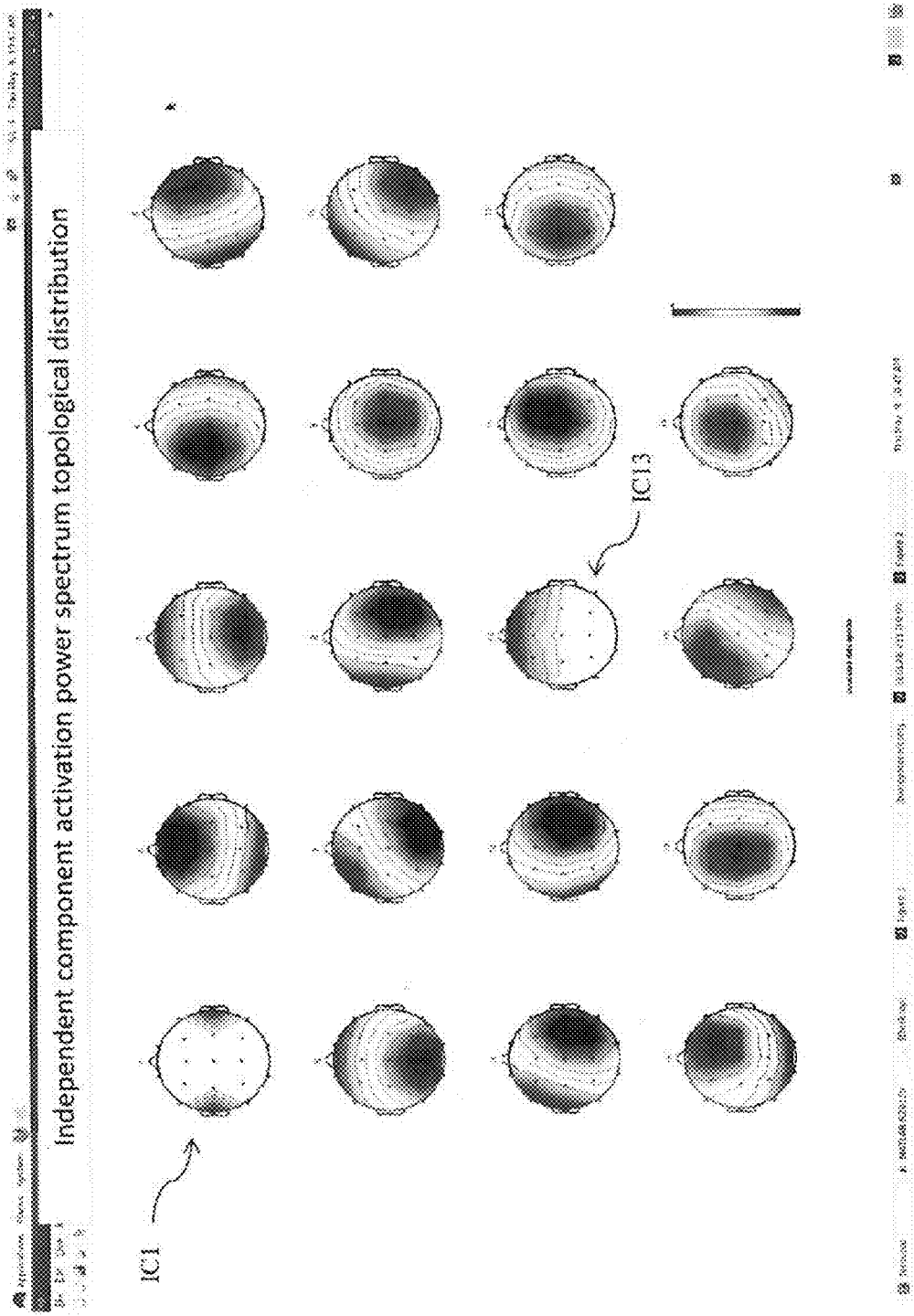
FIG. 17a shows independent component source activation power spectrum topological distribution.
Figure 17B:
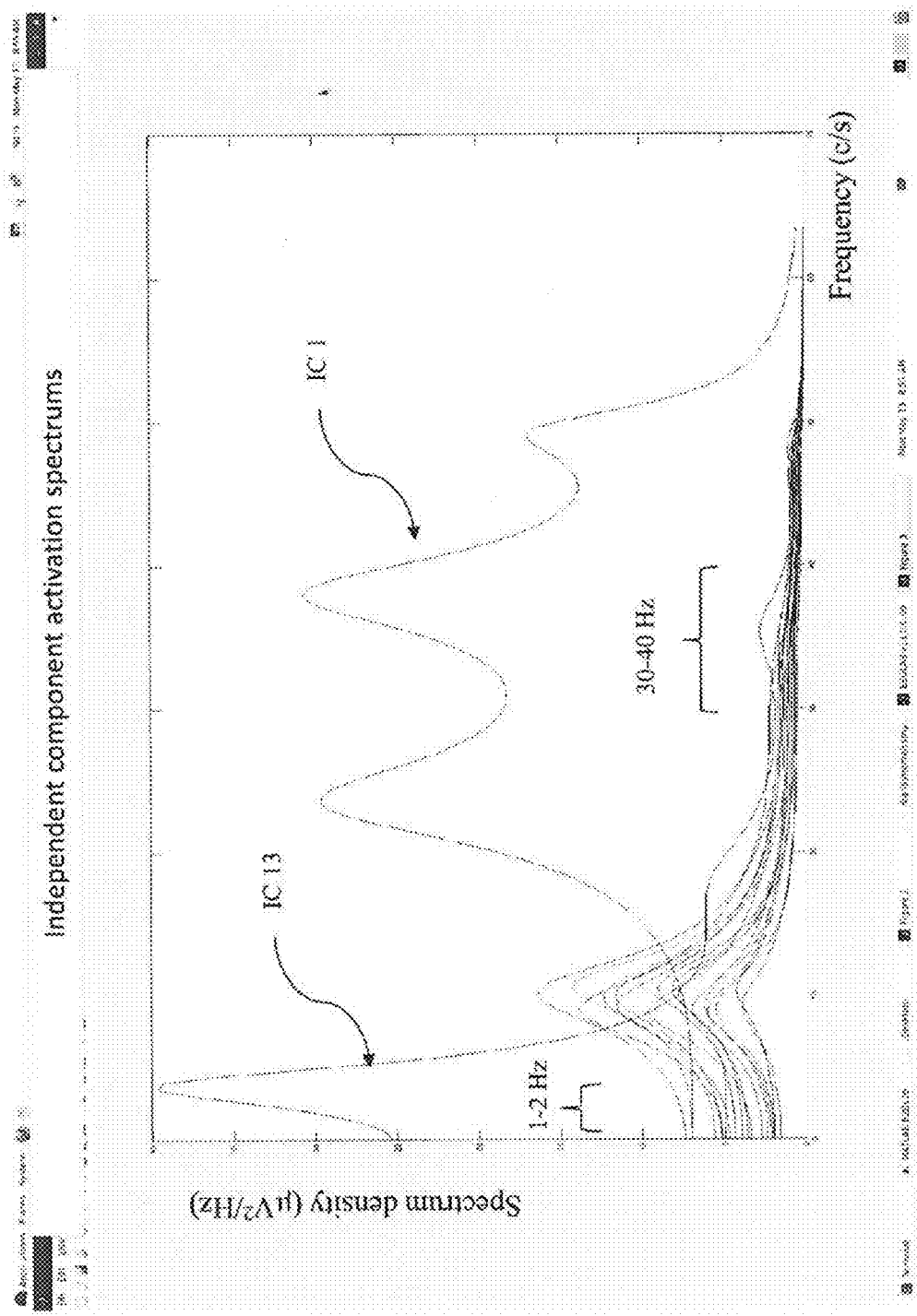
FIG. 17b shows independent component source activation power spectrum density.
Figure 17C:
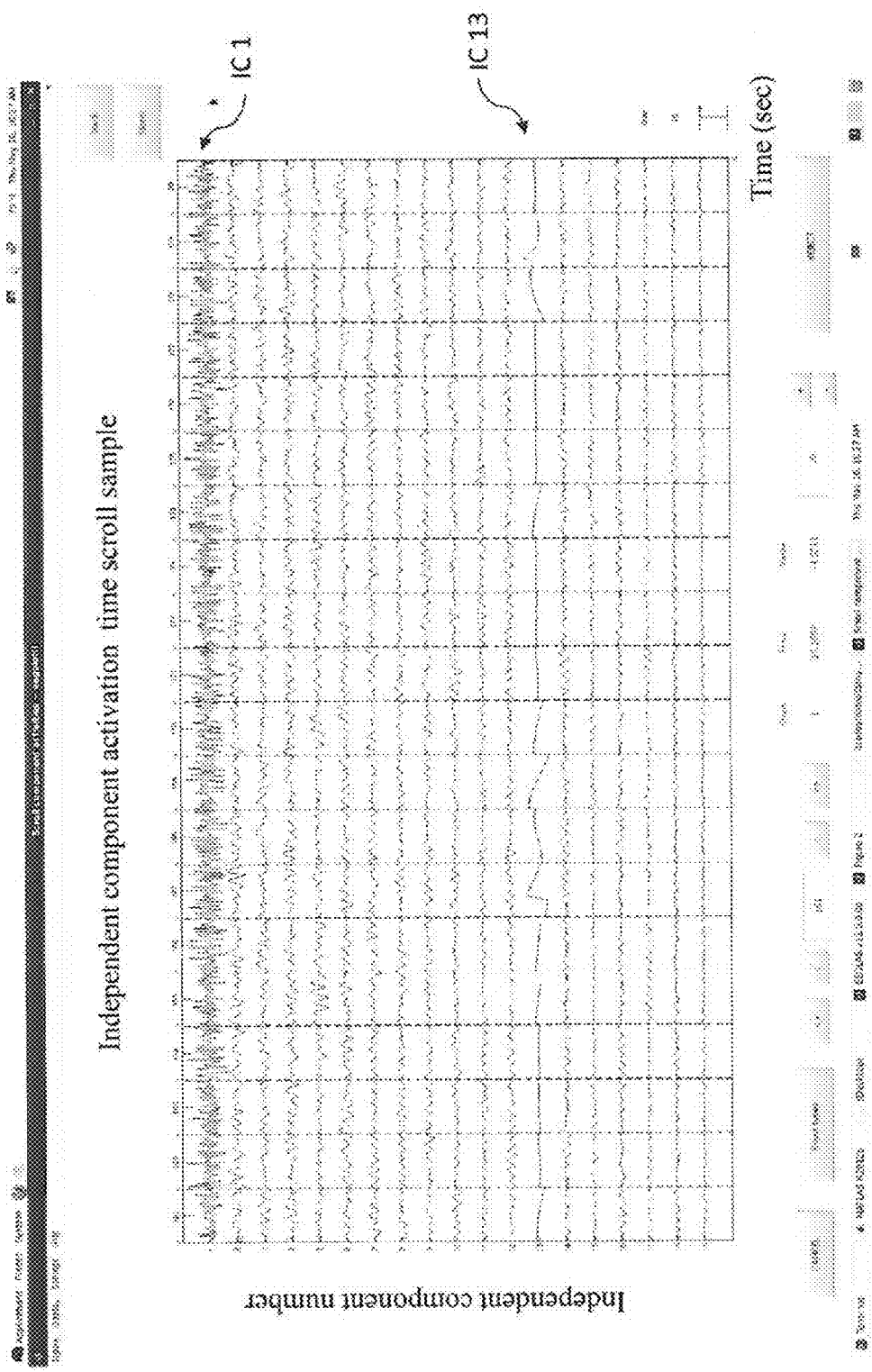
FIG. 17c shows independent component source activation time scroll sample.

Independent Components:

Topological 2-D power plots, activation spectrum plots and activation time line scroll charts are shown in FIGS. 17a, 17b, and 17c for the independent components resulting from the IC analysis. FIG. 17a is a 2-D topological power spectrum plot over the scalp for each of the nineteen independent components (IC); the plot shows patterns for IC1 and IC13 that are suggestive of muscle and eye-movement sources, respectively. A 'dipfit' 3-D diagram (not shown), of the source locations in Talairach space coordinates shows the IC13 source as located in the eye-orbit region. FIG. 17b shows the spectrum plots as organized by source rejection according to the automated or manual rejection criteria. The spectrums for IC1 and IC13 were rejected by both criteria, with the spectrum for IC1 showing high power in the higher frequency range 30-40 Hz corresponding to muscle activity, while the spectrum for IC13 has a high peak in the 2-3 Hz range corresponding to ocular movements. The spectrum for IC 3, 5, and 8 having obvious alpha content were rejected by the automated process because of secondary peaks in the higher frequency range above 30 Hz. The remaining sources were accepted by both methods as limited to alpha content and are colored in blue. Thus, the sources may be considered as forming three categories: (1) obvious artifact sources, (2) sources with a mixture of true signal content and artifact content, and (3) sources limited to pure source content. On this basis, the sources selected for back projection of the activation to the electrode sites are considered for two categories: (I) manual rejection of the IC1 and IC13 sources of obvious artifacts, but retention of the mixed content sources; and (II) the automated rejection of both obvious and mixed content sources, leaving the true content sources. FIG. 17c is a time line scroll sample of the activation functions for the nineteen independent components clearly showing the activation for IC-1 with muscle patterns and that for IC-13 as ocular movements, but little apparent difference among the other activations by time.

Figure 17D:
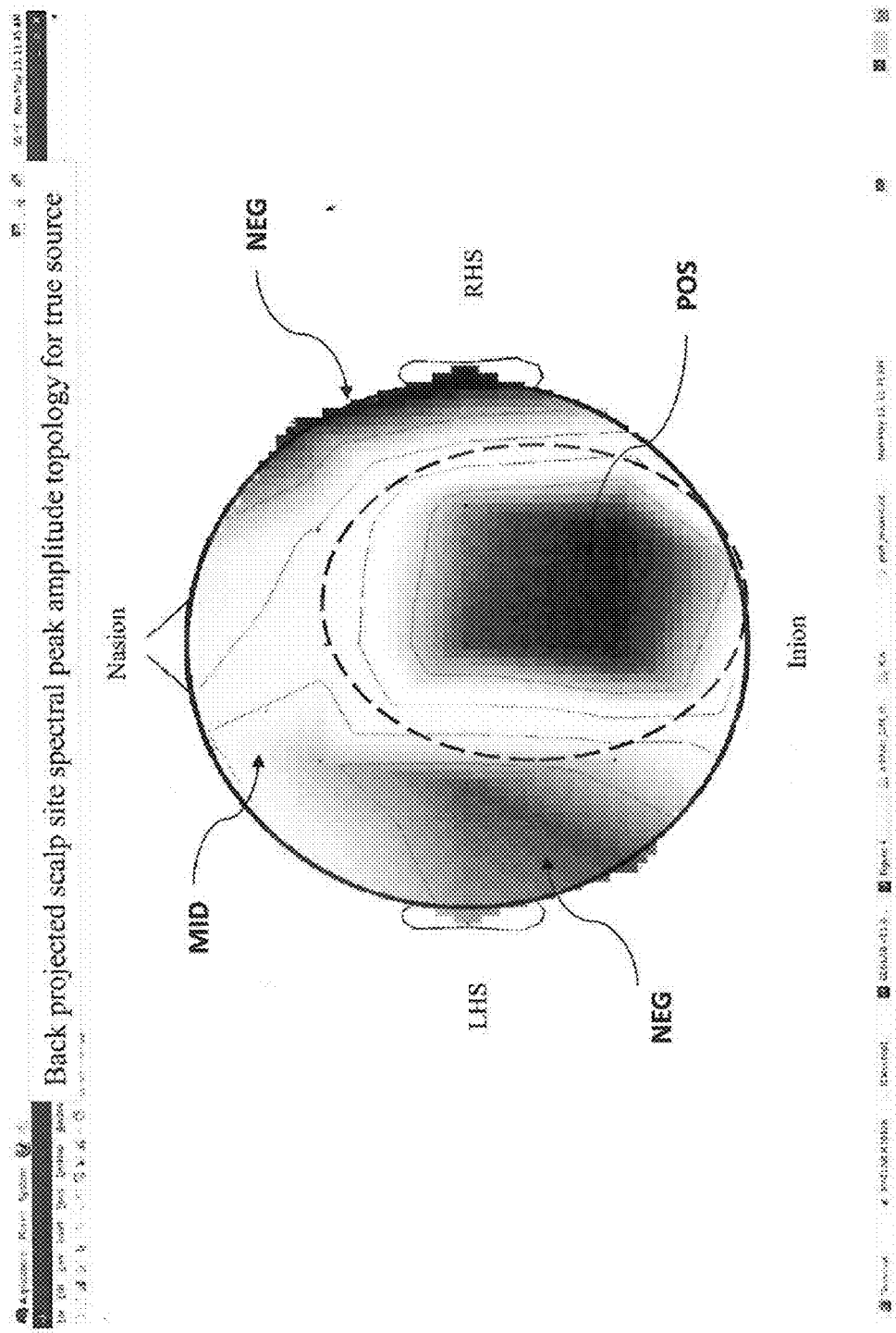
FIG. 17d shows back-projected scalp site spectral peak amplitude topology for true source.

'True' Source Reference:

For reference, FIG. 17d shows a 2-D topological map of the peak amplitudes over the scalp of the electrode site power spectrums generated by the true sources. Although the source distribution is largely uniform (MID), the random source orientations generate a slight positive bias (POS) in the right parietal region (dashed elliptical line), and negative bias to the left and right sides (NEG). The plot is orientated top forward as indicated by the 'Nasion', 'Inion', and 'LHS' and 'RHS' labels.

Back Projection to Electrode Sites:

The results of the back projections of the source activations to the electrode sites are presented for the sources categories and projection methods, and compared to the source projections for the true sources.

Method I. Pseudoinverse Matrix

The back projections are computed from the retained activations using the inverse of the reduced weight matrix calculated by the Moore-Penrose pseudoinverse method. Here, Category I is referred to as case 1 and Category II as case 2 in the figures.

Signal Category I.

Figure 18A:
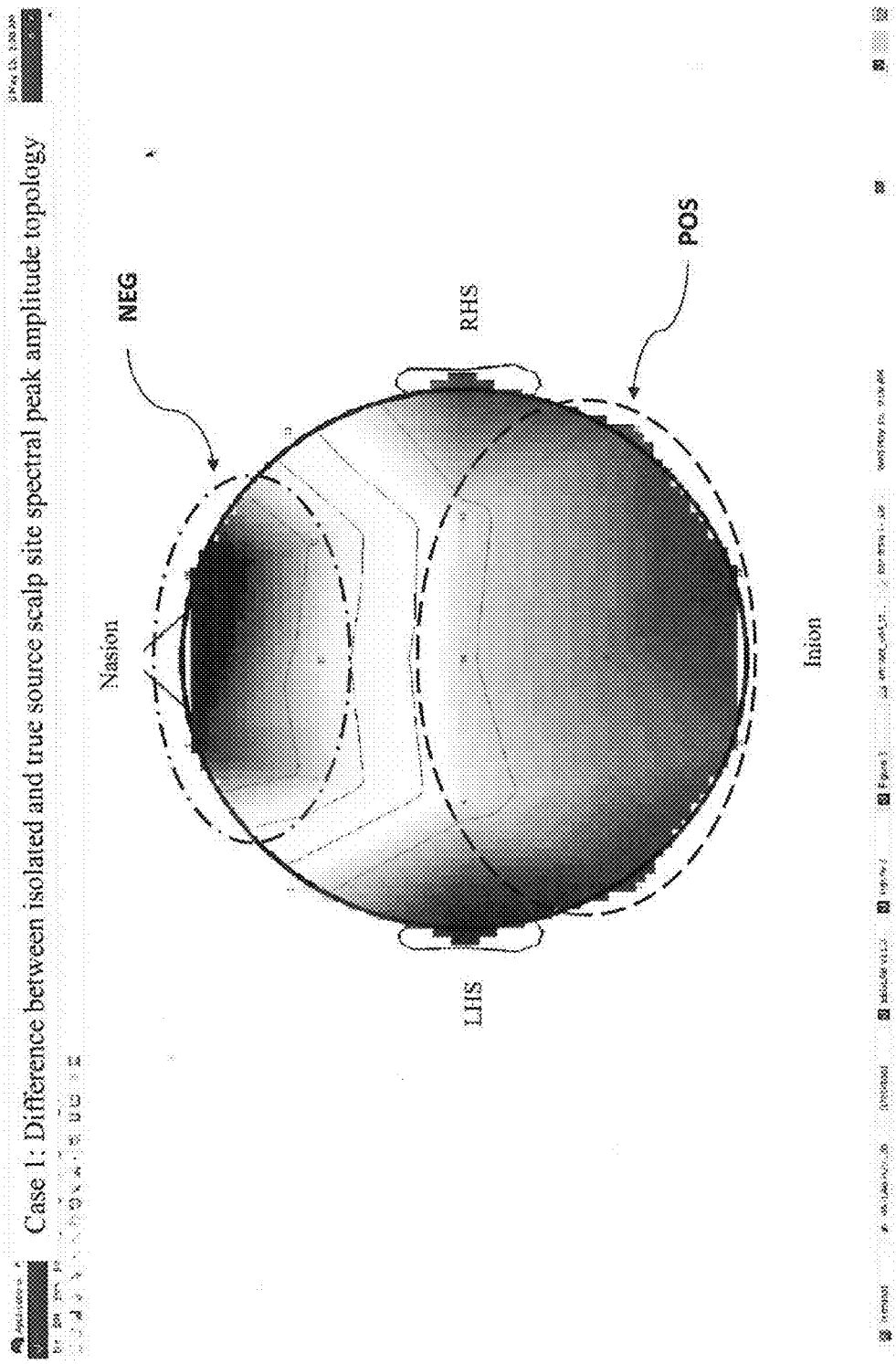
FIG. 18a shows Case 1: Difference between isolated and true source scalp site spectral peak amplitude topological distribution.
Figure 18B:
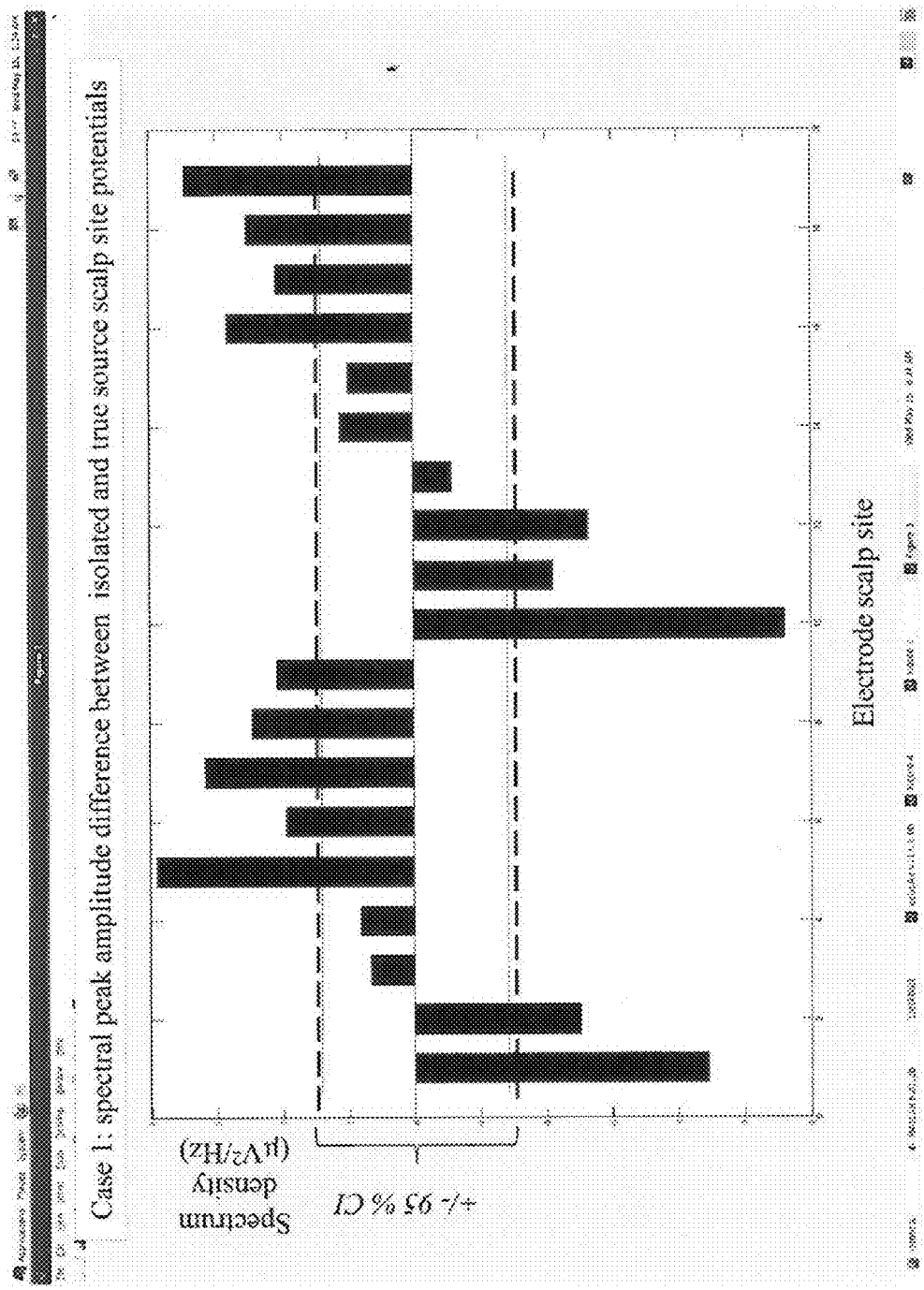
FIG. 18b shows Case 1: spectral peak amplitude difference between isolated and true source scalp site potentials by scalp electrode site.

Sources IC1 and IC13 are rejected, while all others are retained. The difference between the true source spectrum and that for the case sources varies with the site scalp location, with the spectrum for the true source much larger for the anterior site, about the same for the central, and much lower for the posterior. FIG. 18a is a topological plot of the electrode site peak amplitude differences between the true source and case source spectrums; the case source peak amplitude is significantly lower (NEG) in the anterior region (dot-dashed elliptical line), and significantly higher (POS) in the posterior region (dashed elliptical line). FIG. 18b shows this difference by electrode site number for the nineteen sites; the figure shows 95% CI for the differences, and most of the differences extend beyond the interval. A statistical sign-test (and Binomial test), shows that the occurrence of 14 excursions out of 19-events outside the CI bounds is significantly different from random (50% chance) at a one-tail 0.03 probability level. The amplitudes appear to track with a pairwise Pearson correlation coefficient of Rc=0.45, (Matlab 'corrcoef.m'), just barely significant at the 0.05 level.

Signal Category II.

Figure 19A:
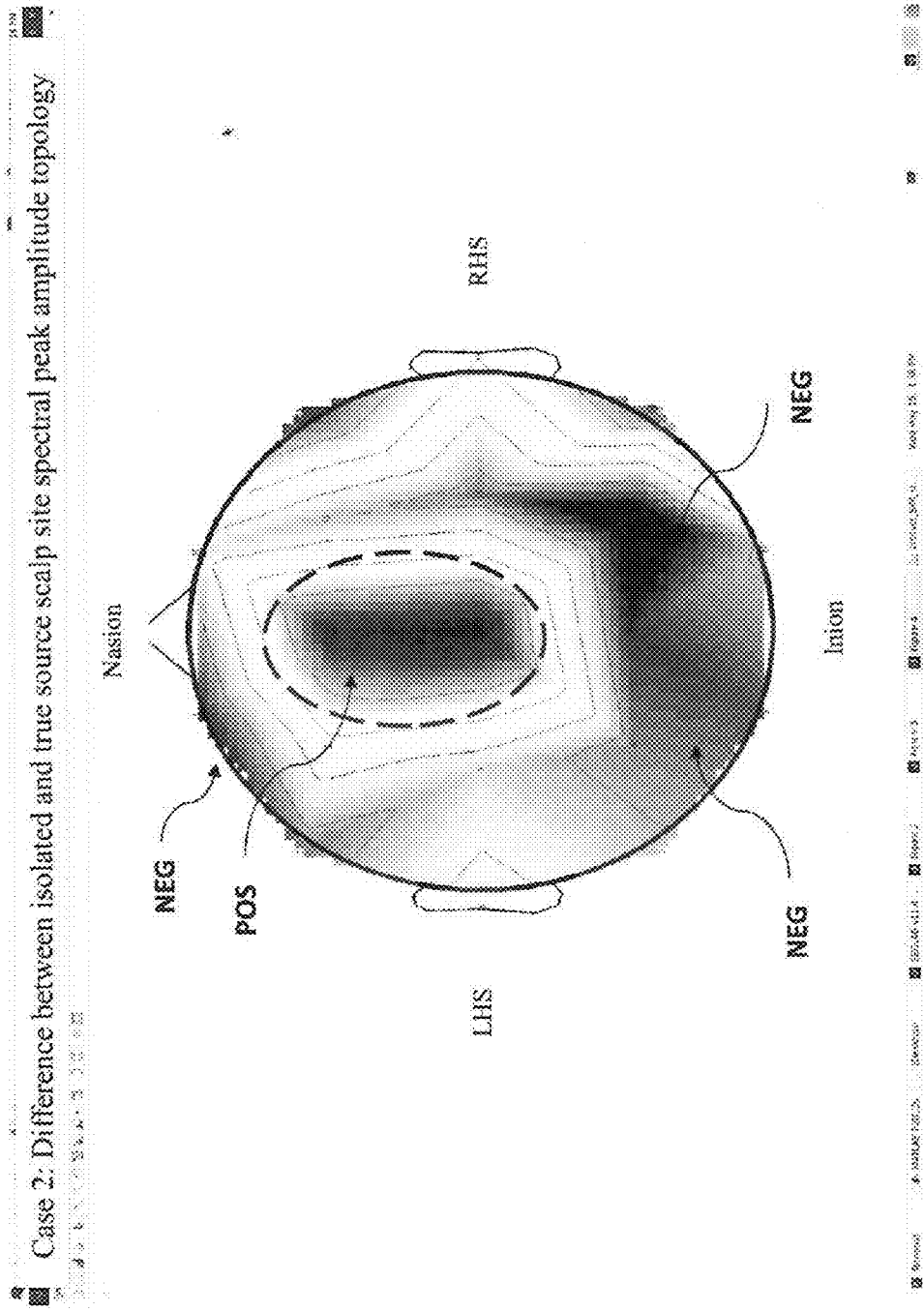
FIG. 19a shows Case 2: Difference between isolated and true source scalp site spectral peak amplitude topological distribution.
Figure 19B:
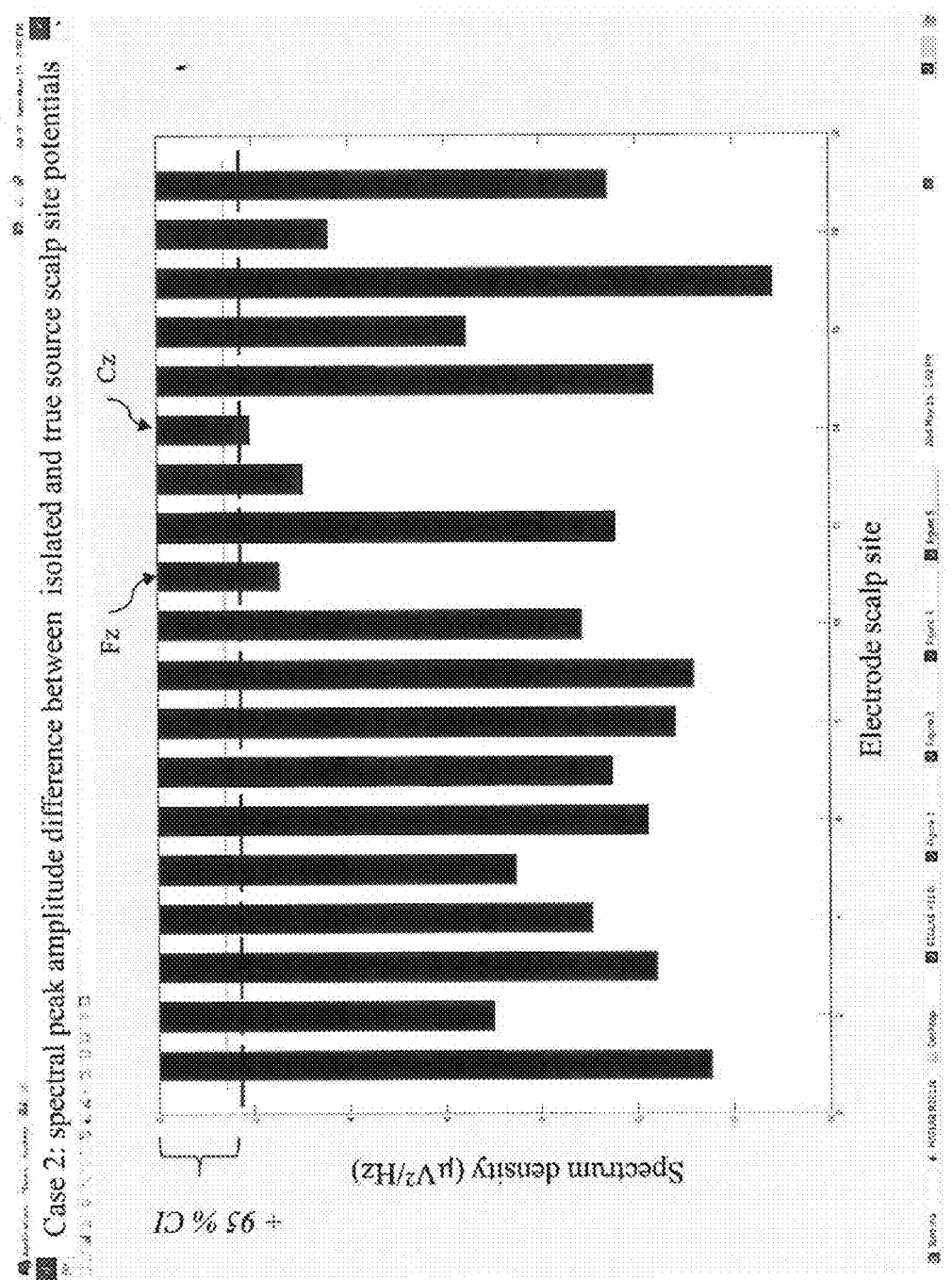
FIG. 19b shows Case 2: spectral peak amplitude difference between isolated and true source scalp site potentials by scalp electrode site.

Sources IC1 and IC13 are rejected along with IC 3, 5, and 8 which show mixed spectrum contents, while the remaining sources are retained. Although the true source spectrum is larger than those for the case sources, the difference varies with the site scalp location, with the spectrum closest in the central region. This is shown by FIG. 19a, a topological plot over the scalp of the electrode site peak amplitude differences between the true source and case source spectrums. The plot shows positive bias in the central region (POS), as indcted by the dashed elliptical line, and negative bias (NEG) at the left frontal and posterior regions of the scalp. FIG. 19b shows this difference by electrode site number for the nineteen sites; the figure shows all differences well outside the 95% CI band (lower limit indicated by the horizontal line). The amplitudes with a pairwise Pearson correlation coefficient of Rc=0.06, (with p=0.84, insignificant from Rc=0), do not appear to track the true value. The case source peak amplitudes are closest to those of the true source between the midline frontal Fz (site 11) and central Cz (site 14) sites.

Method II: Conditioning Activations

The back projections are computed from direct conditioning of the retained activations, using the inverse of the original weight matrix. Here, Category I is referred to as case 3 and Category II as case 4 in the figures.

Signal Category I.

Figure 20A:
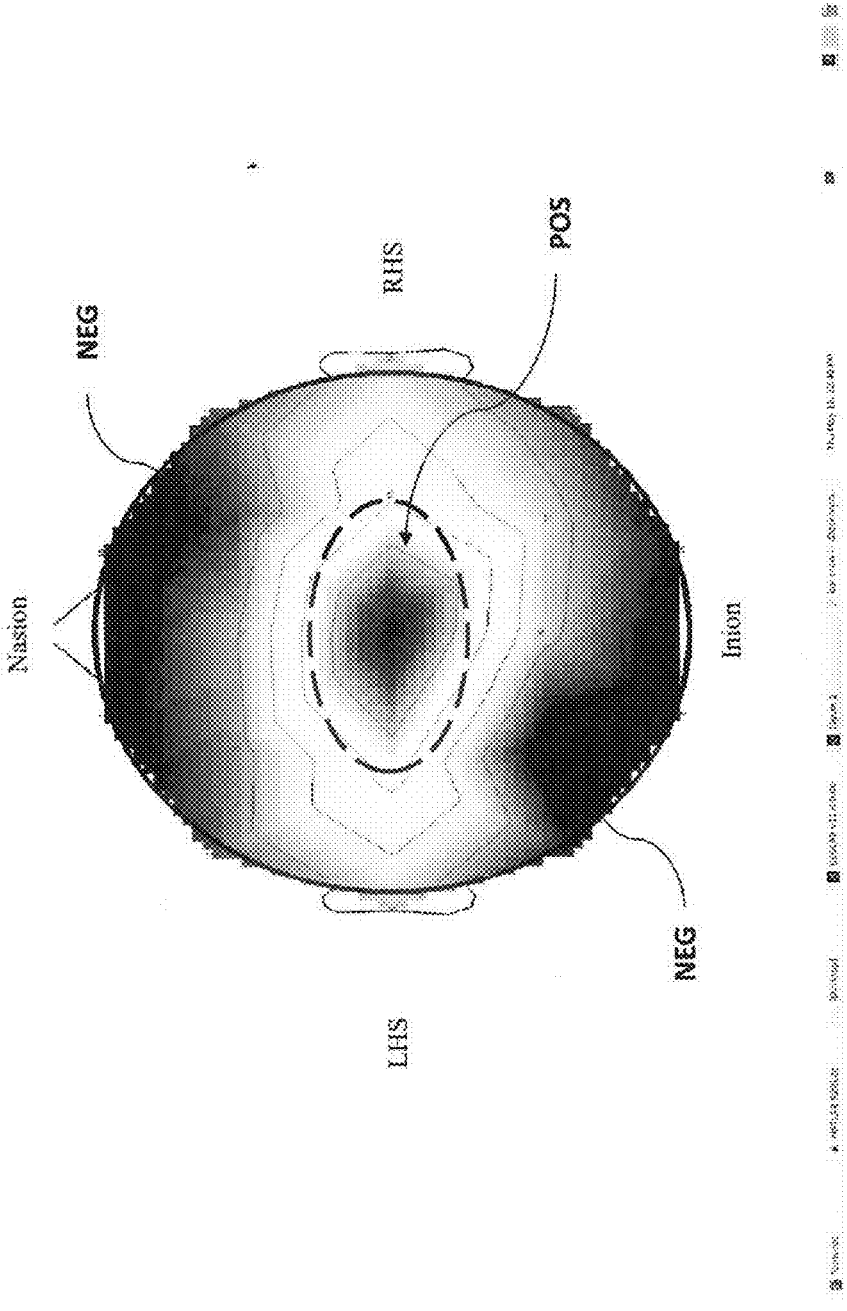
FIG. 20a shows Case 3: Difference between isolated and true source scalp site spectral peak amplitude topological distribution.
Figure 20B:
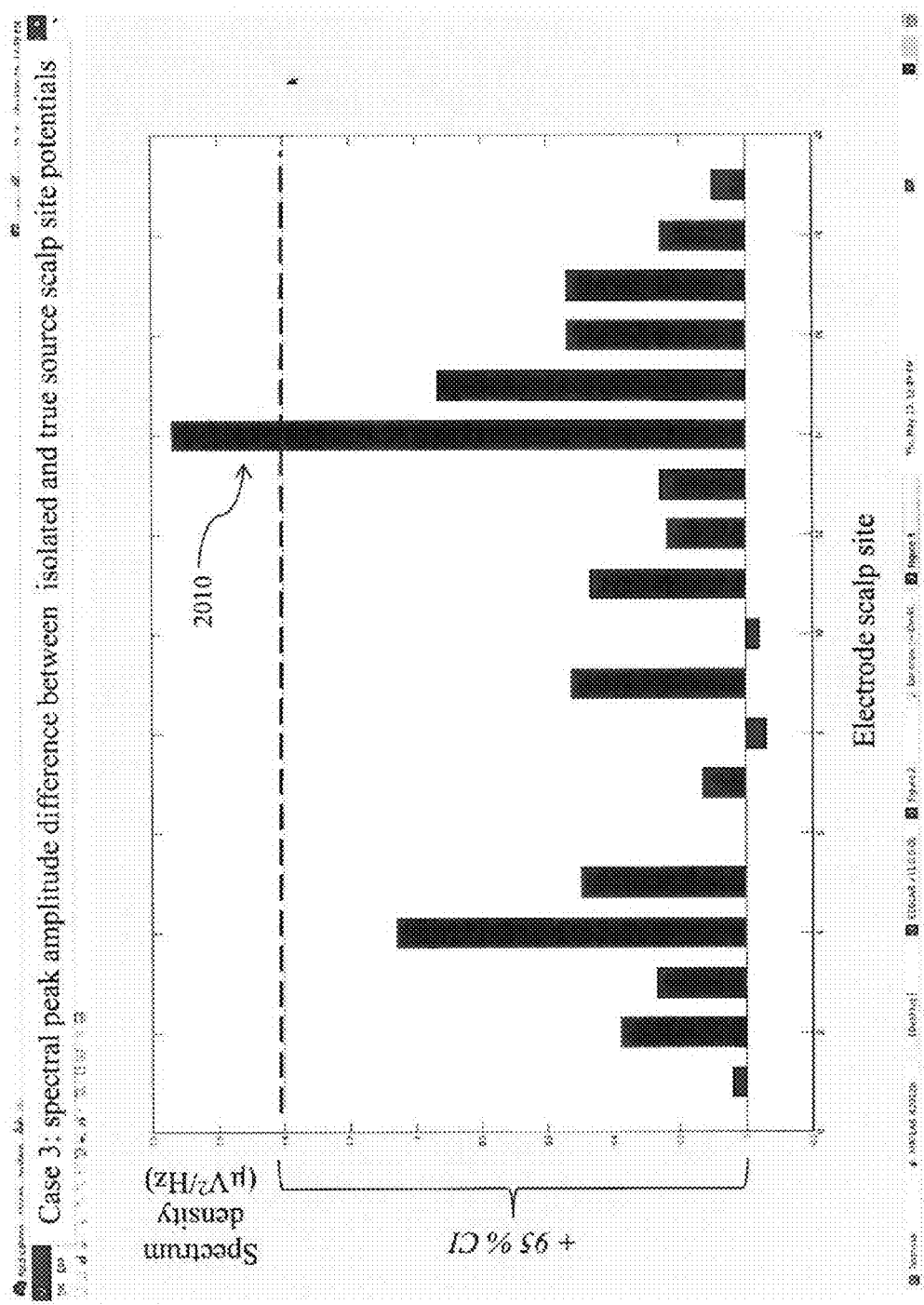
FIG. 20b shows Case 3: spectral peak amplitude difference between isolated and true source scalp site potentials by scalp electrode site.

As before, sources IC1 and IC13 are rejected, while all others are retained. There is little difference between the true source spectrum and that for the case sources by site scalp location. FIG. 20a is a topological scalp plot of the electrode site peak amplitude differences between the true source and case source spectrums; the case source peak amplitude is significantly higher (POS) in the central region centered on the Cz site as indicated by the dashed elliptical linecentered on the Cz site, and lower (NEG) in the frontal and left posterior regions. FIG. 20b shows this difference by electrode site number; the figure shows 95% CI, and only the Cz site 2010 is significantly different. A statistical sign-test (and Binomial test), would shows that the occurrence of one excursion outside the CI bounds for 19-events is insignificantly different from random (50% chance). The amplitudes appear to track with a pairwise Pearson correlation coefficient of Rc=0.949, (Matlab 'corrcoef.m'), highly significant at the p=0.0000 level. The mean difference is 0.451, and the standard deviation is 0.442; suggesting that Cz is an outlier to the distribution.

Signal Category II.

Figure 21A:
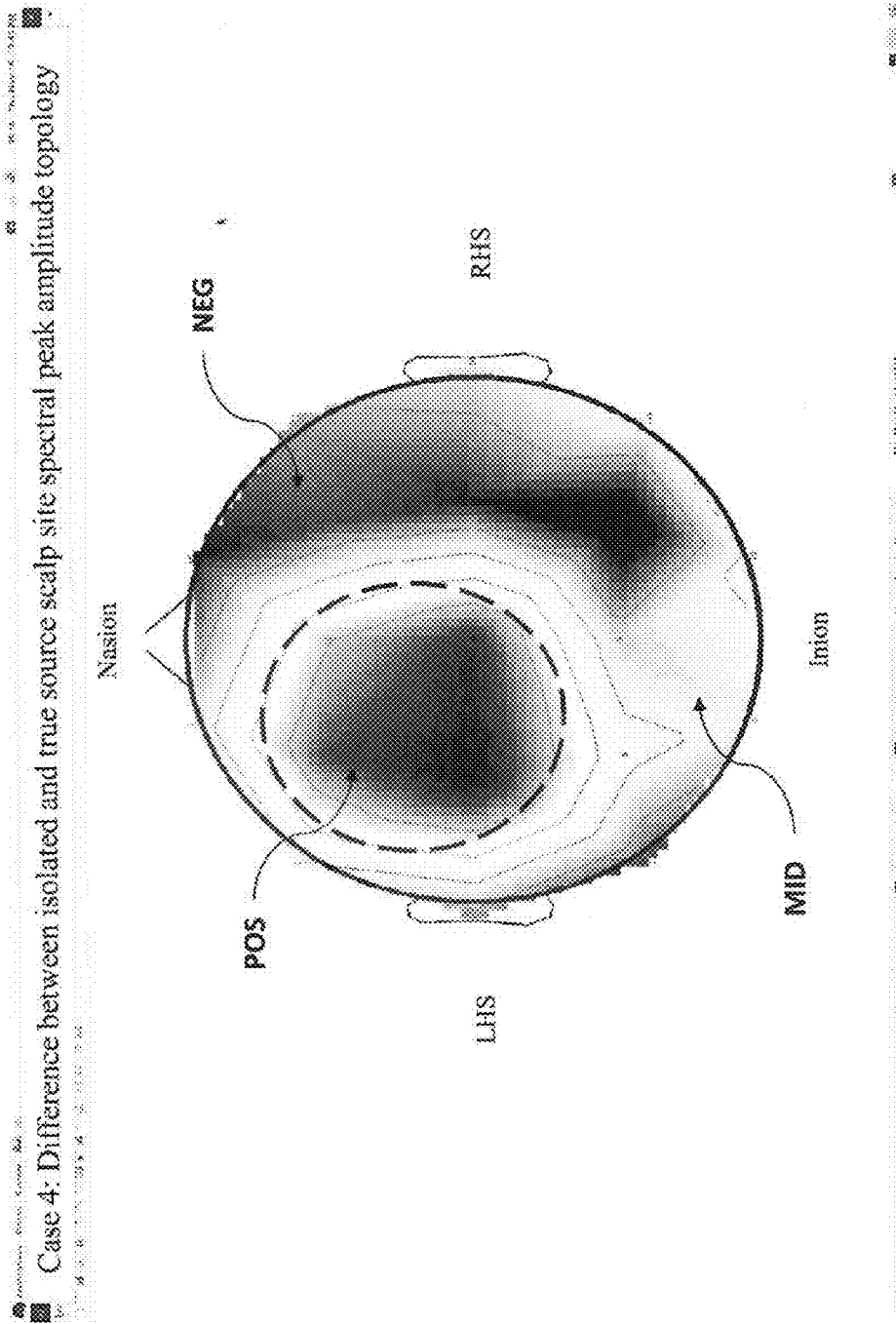
FIG. 21a shows Case 4: Difference between isolated and true source scalp site spectral peak amplitude topological distribution.
Figure 21B:
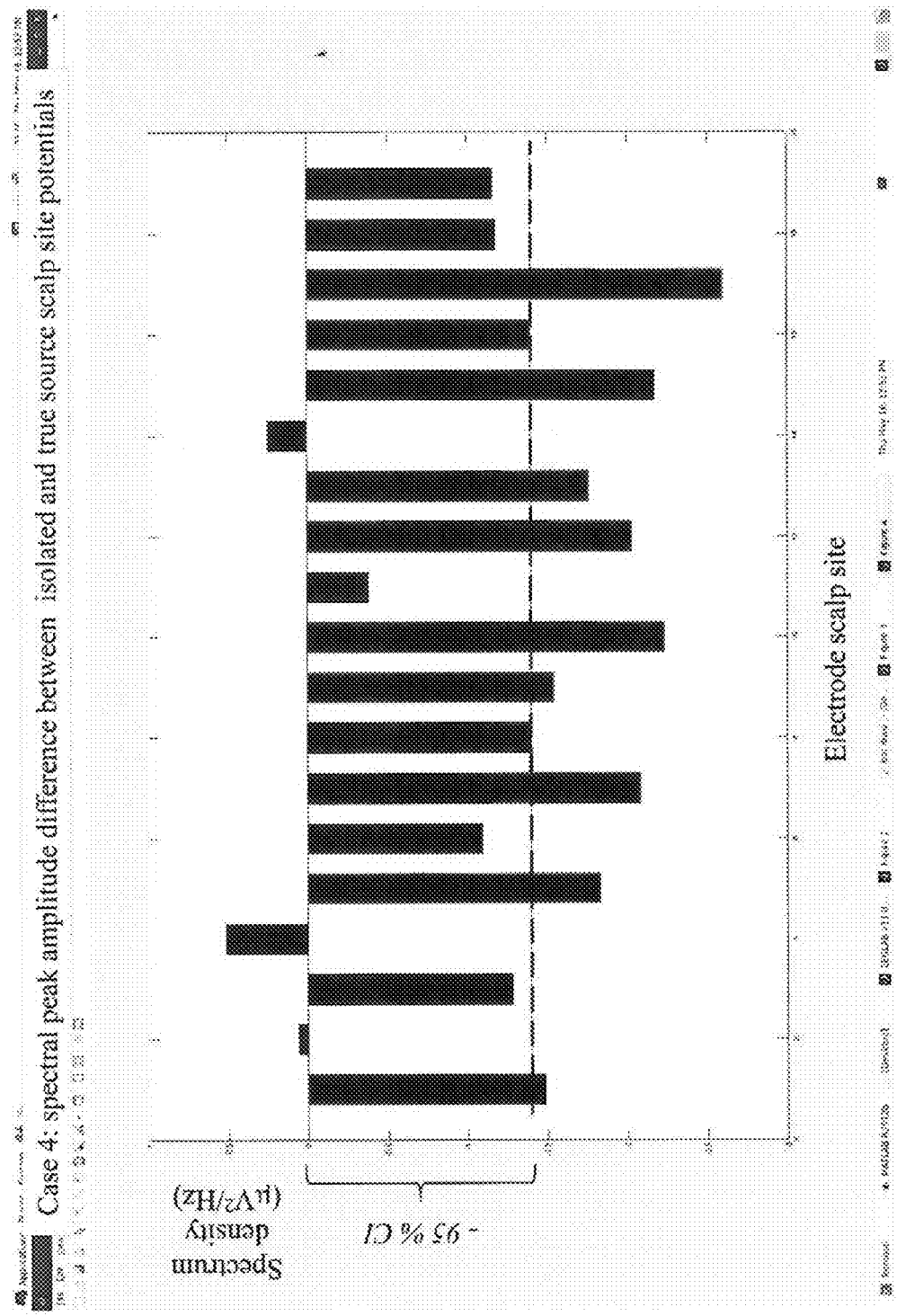
FIG. 21b shows Case 4: spectral peak amplitude difference between isolated and true source scalp site potentials by scalp electrode site.

As before, sources IC1 and IC13 are rejected along with IC 3, 5, and 8 which show mixed spectrum contents, while the remaining sources are retained. There is little difference between the true source spectrum and that for the case sources by site scalp location. This is shown by FIG. 21a, a topological plot of the electrode site peak amplitude differences between the true source and case source spectrums; the case source peak amplitude is larger in the left frontal region (POS) as enclosed by the dashed elliptical line, and less (NEG) in the right frontal and the parietal region centered about the P4 site (site 17). FIG. 21b shows this difference by electrode site number; the figure shows significant differences outside the 95% CI band (dashed line) for sites along the right medial hemisphere (sites 10, 12, 13, 15, 17); however, a statistical sign-test (and Binomial test), would shows that the occurrence of nine excursions outside the CI bounds for 19-events is insignificantly different from random (50% chance). The amplitudes appear to track with a pairwise Pearson correlation coefficient of Rc=0.761, (Matlab 'corrcoef.m'), highly significant at the p=0.0002 level. The mean difference is −1.305, and the standard deviation is 0.866; no outliers are suggested.

Discussion: The study shows an interaction between the back projection method and the number and type of components rejected. The projected scalp distributions are influenced by the back projection method with the pseudoinverse matrix method showing significant bias in distribution and significantly less power depending upon the number and type of components rejected. This is in contrast to the activation conditioning method which results in distributions closer to that of the true sources, with however, insignificant bias in distributions depending upon the components rejected. The matrix product of the reduced matrix and the pseudoinverse provides a measure of the level of conditioning of the process, where perfect conditioning would result in a unity matrix product (all diagonal elements equal to unity and all off-diagonal elements equal to zero); meaningful statistics are the mean and standard deviation of the matrix, the diagonal elements, and the off-diagonal elements. Table 4 lists pseudoinverse matrix statistics by component category as an indicator of the number of components removed. Noting that a unity matrix (column rank 19) has a matrix average of 0.053 and mean standard deviation of 0.229, the table shows that as the matrix is reduced the pseudoinverse is less like a unity matrix; for Category I with two components removed, the matrix mean is reduced to 21.1% of that for the unity matrix, and for Category II with five components removed, the matrix mean is 3.8% of that for the unity matrix, resulting in less accurate back projection of the activations.

There is a secondary effect of the type of components rejected. While some components are obvious ocular or muscle artifact sources, other components are graded combinations of source and artifact spectrums and may be ranked accordingly for removal. The strength of the back-projected scalp potentials is increased by including more components, but the lower frequency muscle spectrum content may distort the topological distribution. A review of the secondary and tertiary amplitude peaks shows that while all scalp sites have a low amplitude tertiary peak (about 47 Hz) under all analysis treatments presumably induced by the preprocessing low pass filtering, the distribution of the secondary peak (about 27 Hz), depends upon the component rejection process. For the manual process in which the obvious artifact component sources for muscle and ocular movements (IC 1 and 13) were rejected, the secondary peaks were present at the sites 4, 9, 10, and 13-16, but not the remaining sites, corresponding to a right central bias in this frequency content. In contrast, for the automatic process in which the additional components 3, 5, and 8 were removed based upon their expended spectrums, the secondary peak is present at nearly all scalp sites and of reduced amplitude. A reasonable interpretation of these results is that the ICA process using kurtosis amplitude distribution statistics separates the higher frequency muscle artifacts but leaves a residual of the lower frequency content in the 35 Hz range and possibly into the alpha band range. This would explain site 14 as an outlier for case 3 (see FIGS. 23 and 24), in which the stronger residual of components 3, 5, and 8 are carried over to bias the central temporal sites.

Summary: The effectiveness of Independent Component Analysis is determined by the number and spectrum of the independent components retained, as well as by the method of projecting the retained activations back to the electrode sites, at least as shown by this simulation study using power spectrum density (PSD) analysis. While some components are obvious ocular or muscle artifact sources and therefore should be removed, other components are graded combinations of source and artifact spectrums and may be ranked accordingly for removal. The strength of the back-projected scalp potentials is increased by including more components, but the lower frequency muscle spectrum content may distort the topological distribution. Perhaps the ICA process inadvertently separates the higher frequency muscle artifact from a lower frequency residual that with an amplitude distribution that is more sinusoidal is added into the cortical signal spectrum. For small electrode sets such as the 10-20 electrode system, a direct method of conditioning the retained activations for projection back to the electrode sites may be more effective than using an inverted reduced weight matrix commonly derived by the Moore-Penrose pseudoinverse method because of the resulting ill-conditioning. In this study as an example, back projection by the pseudoinversive matrix following removal of obvious artifact components for ocular and muscle resulted in a significant bias toward the parietal scalp sites and away from the frontal sites as compared to the true source signals; with the same projection method following removal of both obvious artifacts and severely graded sources, the bias was toward the mid-line central scalp with significantly reduced signal. In contrast, a direct method of back projection resulted in insignificant bias toward the central sites; however, the projection fit was less for the case of removing just the obvious artifact components, although the strength was reduced when both obvious and graded sources were removed.

Effects of Reference Electrode Configuration

Purpose:

Determine the effect of the reference electrode on the back-projection methods for three reference configurations: inert non-scalp site (ear), average of scalp sites (average), and linked ear average (linked).

Method:

An Independent Component Analysis was applied for source isolation following artifact rejection to a simulated data base generated by known artificial cortical sources and superimposed eye-movements, blinks, and muscle movements; and compared to the projected scalp site signals to those generated by the cortical sources without the artifacts. The rejection and analysis was applied following referencing of the simulated data base using the EEGLAB 'pop_reref.m' routine.

Source Configurations:

Cortical sources are simulated dipole sources embedded in a MNI Talairach reference coordinate space with delta, theta, alpha, and beta band task specific spectral parameters of power, bandwidth, and peak amplitude. The sources are modeled as an autoregressive filter process driven by white noise, where the filter coefficients are derived for the spectrum of the source as a set of oscillators with strong alpha band power. In this study, 34 sources were used with all sources activated by the same spectrum, but random orientation.

Cortical Head Scalp Site Potentials:

Cortical potentials at the head scalp sites are generated as the sum of the potentials from the simulated cortical dipole sources transformed to four-shell spherical head model locations. The dipole source potentials are the resultant of tangential and radial dipole components computed from the source location and orientation relative to the head model spherical surface.

Site Configuration:

The electrode scalp sites correspond to the 10-20 electrode system composed of 19-electrode channels, and a left and right EOG configuration. The digital average of sites labeled T7 and T8 (sites number 5 and 16), were used for the linked ear common reference.

Artifact Generation:

Artifacts are simulated using mathematical models for the different artifact sources for muscle movements, and for eye-movements and blinks; the source potential at the electrode sites is weighted by the scalp topology separation distance.

Data Base Format:

The database is organized in a manner similar to the prior studies in 12 blocks each 100-seconds, where the blocks are combinations of the artificial source signal, the EOG (two levels), and the EMG (3-levels), Block 1 containing source signal without artifacts constituted about 8.3% of the data; Blocks 2 and 3 contain ocular artifacts (high, low level movements), Blocks 4 thru 6 contain muscle artifacts (high, mid, low intensity), while Blocks 7 thru 9 contain the same with high level ocular movements, and Blocks 10 thru 12 such with low level ocular movements. Note that the eye movements and blinks occur only occasionally, and the muscle artifacts build up and decrease according to a half-sinusoidal envelope (simulating slow head rotation and back) in the corresponding blocks. The result is that all blocks have some portions with mainly true source signals.

Artifact Rejection Process:

A standard EEGLAB analysis process prepared the data base for application of the ICA using software commands as follows:

'Edit/select data': The scalp site channels 1-19 were selected for analysis;
'Tools/Remove baseline': The baseline is removed from all channels;
'Tools/Filter the data/Basic FIR filter': All channels were digitally band pass filtered with a 50-Hz low-pass filter, and then a 1-Hz high-pass filter;
'Tools/Extract epochs': Epoch selection (0-0.5 s), epoch baseline removal (0 0);
'Tools/Epoch rejection (all techniques)': the rejection techniques were applied sequentially for the 0.5 s epoch size, with the settings set at the recommended level for the amplitude (+/−25 uV), trend (+/−50 uV/epoch), and spectrum (+/−25 uV dB), and the joint probability and kurtosis (5%; 5%).

ICA Process:

The EEGLAB command 'runica.m' was applied to the resulting data set; an automated technique for component classification as signal or artifact was applied to the resulting independent component dipole set based on the IC activation spectrum (goodness of quadratic fit), spectrum peaks by number of peaks below 3 Hz (eye-movements) or above 30 Hz (muscle spectrum), and dipole location within the Talairach reference coordinate space (within sphere, behind eye-orbit regions). The automated results were manually reviewed using the EEGLAB routines for component scroll, spectrum, topological power distribution (2-D map), and dipole location in the Talairach representation for component removal and back projection of the component activations to the scalp sites.

Study Process:

The logarithmic power spectral density of the back projected signals isolated at the electrode sites are computed using the MATLAB 'psd.m' function (via EEGLAB 'spectopo.m'); the originating 'true' source spectrum is assumed a ground truth reference. The spectral density peaks were determined using the MATLAB 'findpeaks.m' function and the alpha band peak amplitude is reported for results.

Study Results:

The alpha band peak amplitudes of the scalp site signals for the isolated signals and the 'true' source signals are compared for the reference electrode configurations and the back projection method.

Figure 22A:
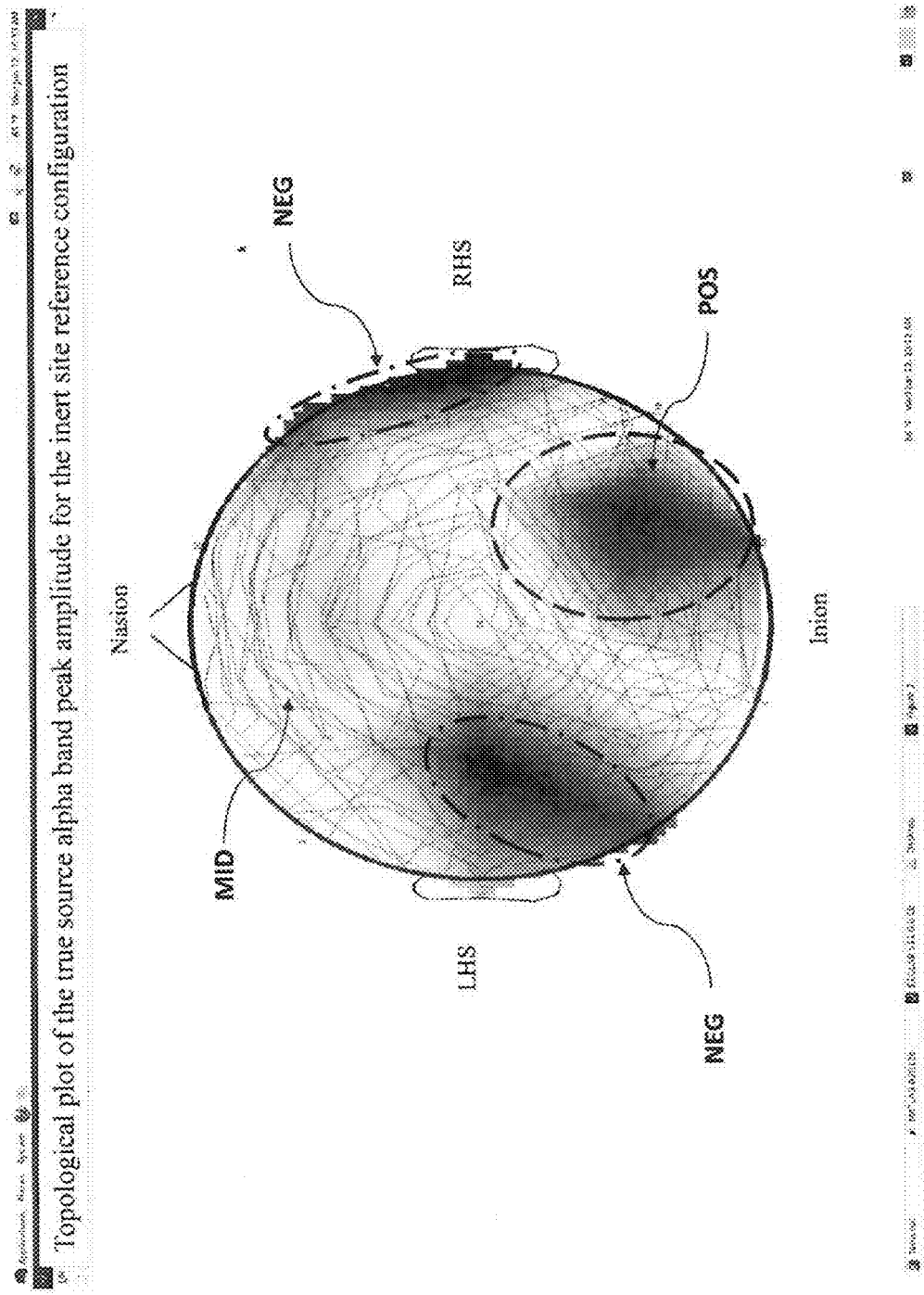
FIG. 22a is a topological plot of the true source alpha band peak amplitude for the inert site reference configuration.
Figure 22B:
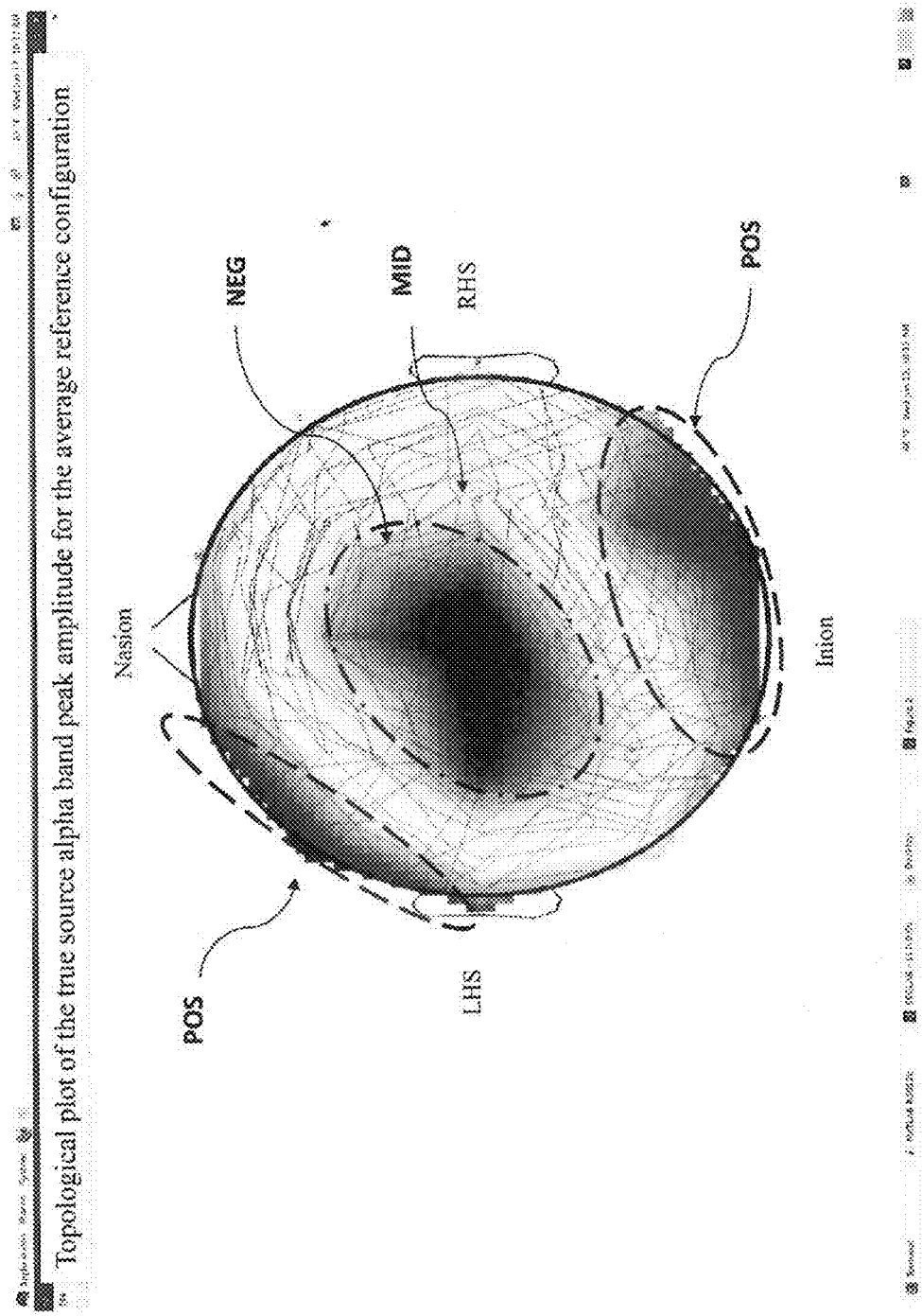
FIG. 22b is a topological plot of the true source alpha band peak amplitude for the average reference configuration.
Figure 22C:
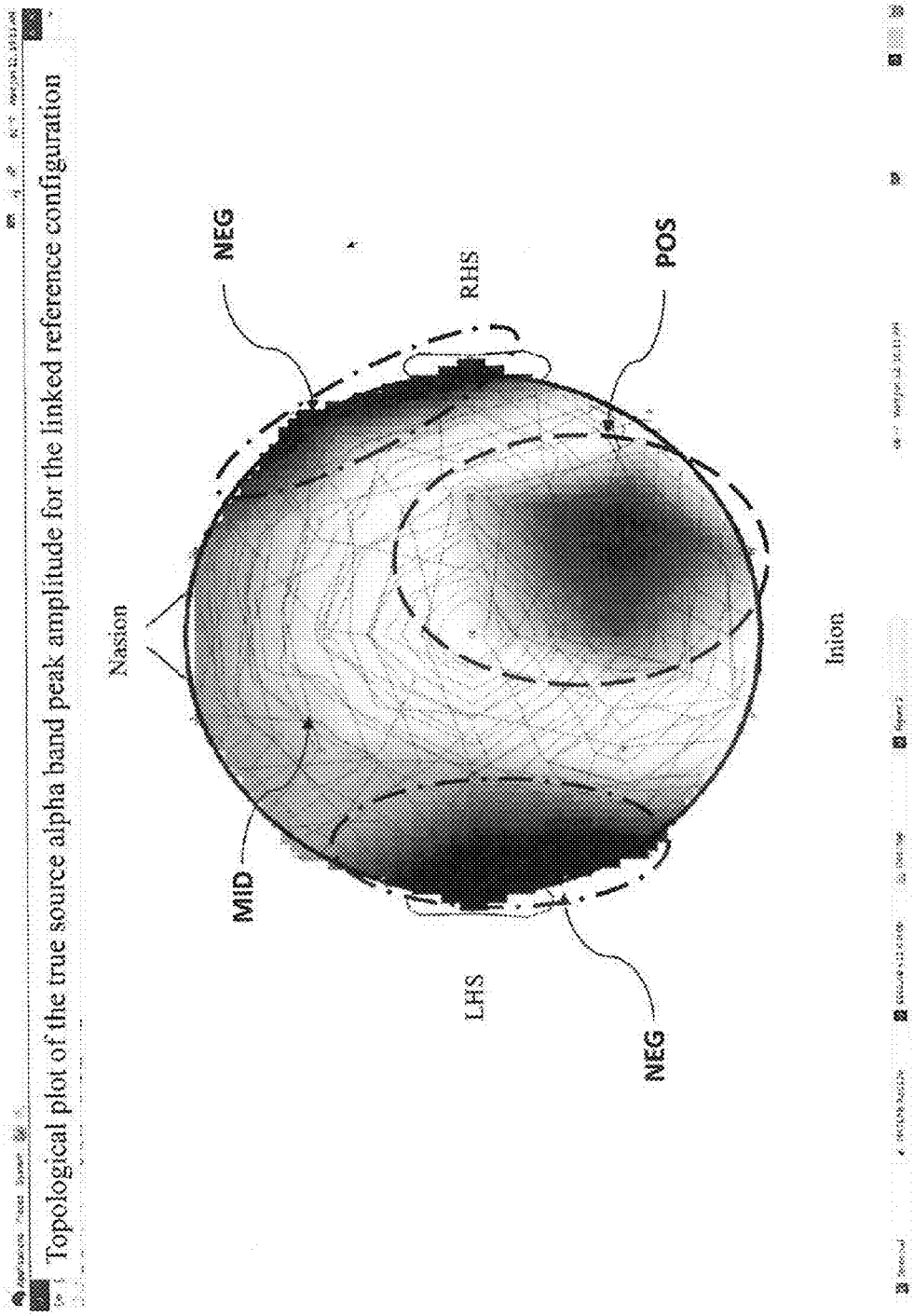
FIG. 22c is a topological plot of the true source alpha band peak amplitude for the linked reference configuration.

True Sources:

For reference, FIGS. 22a, 22b, and 22c are topological scalp plots of the true source scalp peak alpha band amplitude distribution (EEGLAB 'topoplot.m; with 'maplimits', 'maxmin'), for the inert, average, and linked reference electrode configurations, respectively. The plots of FIG. 22a and FIG. 22c for the inert and linked distributions are similar showing a bias toward the right parietal and occipital scalp regions, while that of FIG. 22b for the average reference shows a negative bias toward the center. In particular, FIG. 22a shows a positive bias (POS) in the right occipital. lobe, and a negative bias (NEG) in the right temporal and left ide frontal; the remaining at an intermediate values (MID). Similarly, FIG. 22c shows positive bias (POS) in the right occipital and parietal regions, a negative bias (NEG) in the left temporal and right side frontal, and intermediate values (MID) in between. In contrast, FIG. 22b shows a strong negative bias (NEG) in the left central region and a positive bias (POS) in the right occipital and left side frontal, with intermediate (MID) between these poles. The peak amplitude average and standard deviation power spectra density statistics [in $dB=10*\log_{10}(uV^2/Hz)$], for the reference configurations are inert: [5.76; 0.62], average: [5.46; 5.99], and linked: [6.06; 0.89], showing narrow distributions for the inert and linked, and a wide distribution for the average reference in agreement with the plots. A paired sample t-test (MATLAB ttest.m) shows that the inert and linked peak distributions are significantly different in amplitude (p=0.0196), while the average is not from either. Considering the effects of the reference configurations on the distribution of the 'true' source alpha band peak amplitude by electrode site, a Pearson pairwise correlation analysis (MATLAB 'corrcoef.m') shows a significant 83.47% correlation coefficient (Pc=0.0000), between the distributions of the inert and linked configurations, a 48.47% correlation coefficient (Pc=0.0355) between the inert and site average references, but an insignificant −3.31% correlation coefficient (Pc=0.8931) between the average and linked references, implying that the inert and linked configurations are similar, separate from the site average.

Figure 22D:
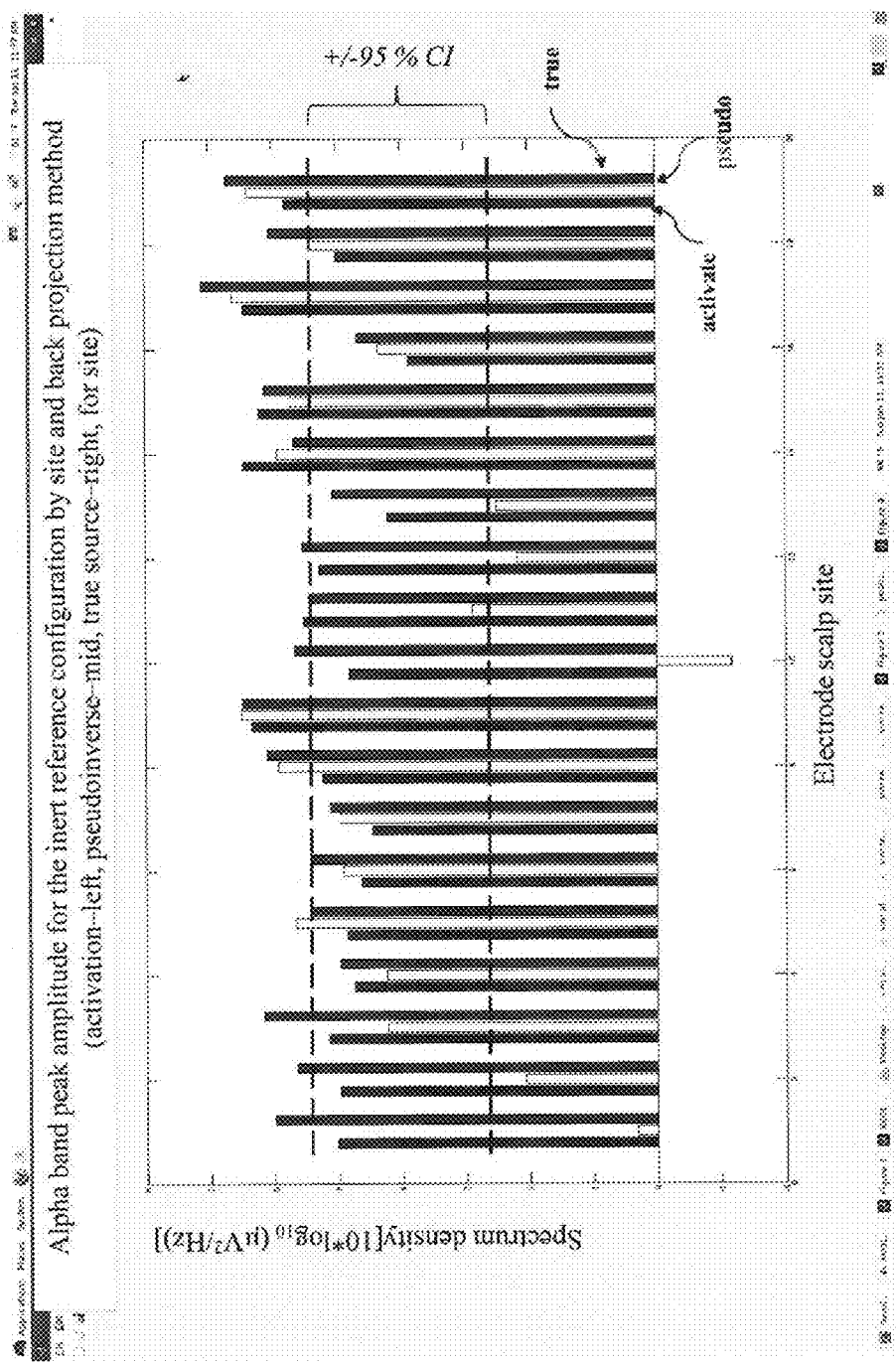
FIG. 22d shows alpha band peak amplitude for the inert reference configuration by site and back projection method.

Inert Site Configuration:

FIG. 22d is a plot of the alpha band peak amplitude for the inert reference configuration by scalp electrode site and back projection method; a 95% CI for the average true value is shown for reference. The figure shows that while the peak amplitude for the activation method (activate) is well within the CI for the true values (true), those for the pseudoinverse method (pseudo) are well outside the CI for many of the electrode sites. A pairwise correlation analysis shows that the activation method results are significantly correlated with those of the 'true' source (Rc=77.47%, Pc=0.0001), but the pseudo inversion method results are not (Rc=36.70%, Pc=0.1222), and the two methods have insignificant correlation with each other (Rc=44.87%, Pc=0.0540). The average and standard deviation statistics are for the activation method [5.21; 0.75], and the pseudo inversion method [4.20; 2.19], showing a narrow distribution for the activation method but a wide distribution for the inversion. A paired sample t-test shows that the activation and inversion peak distributions are significantly different in amplitude from that of the 'true' source (activation: p=0.0000; inversion: p=0.0037), as well as from each other (p=0.0376). Topological plots (not shown) of the scalp peak alpha band amplitude distribution for the back projection methods show a positive bias in the right parietal and occipital scalp regions for the activation method, a pattern much like that for the 'true' source with a corresponding difference plot bias in the central region; the pseudo-inversion method shows a strong positive bias in the posterior region and corresponding negative bias in the frontal regions with the difference plot reflecting this forward tilt in the distribution.

Figure 22E:
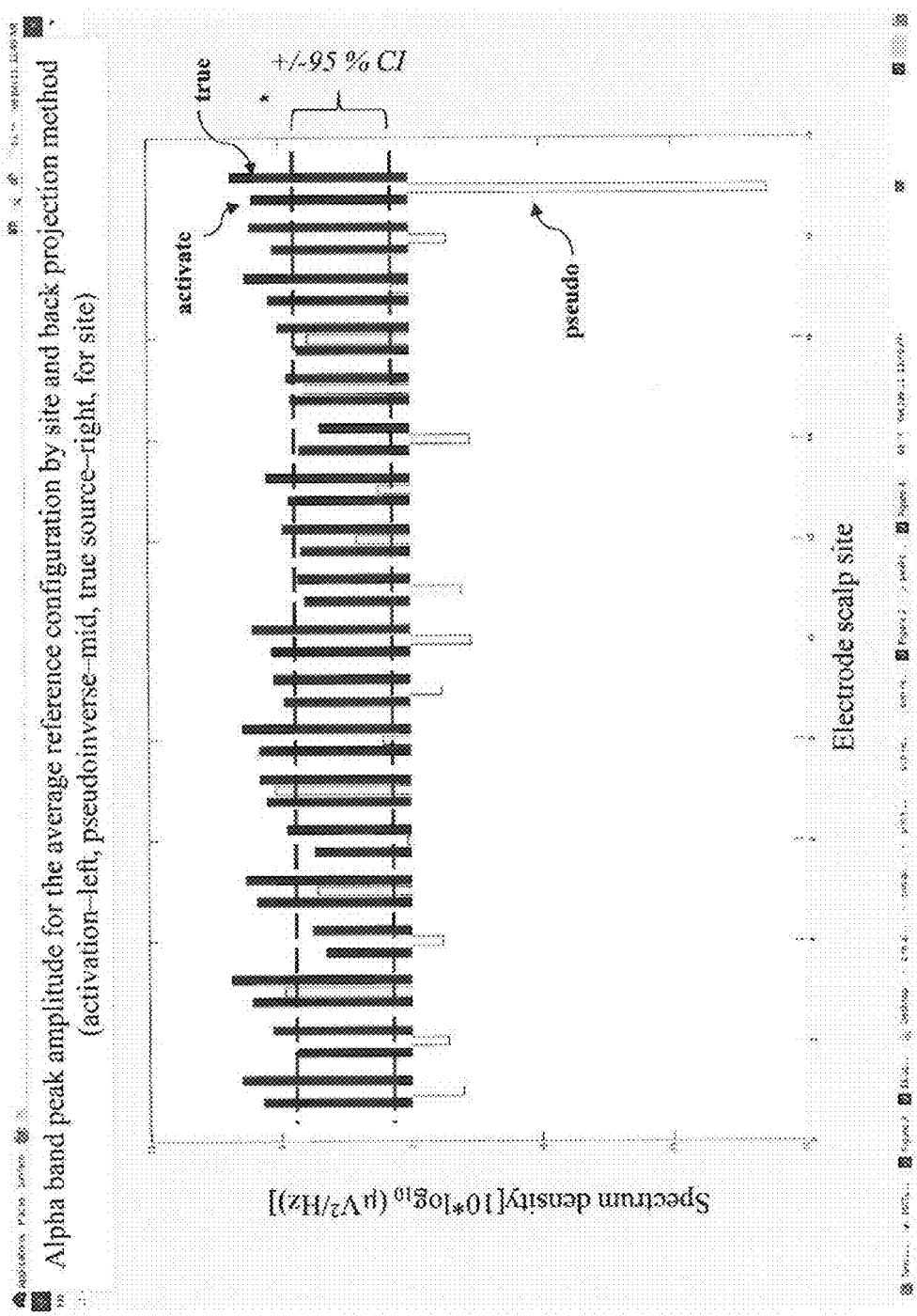
FIG. 22e shows alpha band peak amplitude for the average reference configuration by site and back projection method.

Site Average Configuration:

FIG. 22e is a plot of the alpha band peak amplitude for the site-average reference configuration by site and back projection method; a 95% CI for the average true value is shown for reference. The figure shows that while the peak amplitude for the activation method (activate) is well within the CI for the true values (true), those for the pseudoinverse method (pseudo) are well outside the CI for most of the electrode sites. A pairwise correlation analysis shows that the activation method results are significantly correlated with those of the 'true' source (Rc=91.21%, Pc=0.0000), but the pseudo inversion method results are not (Rc=−8.15, Pc=0.7401), and neither are the two methods with each other (Rc=−7.09%, Pc=0.7731). The average and standard deviation statistics are for the activation method [4.88; 0.83], and the pseudo inversion method [−0.04; 4.17], showing a narrow distribution for the activation method but a wide distribution for the inversion. A paired sample t-test shows that the activation and inversion peak distributions are significantly different in amplitude from that of the 'true' source (activation: p=0.0000; inversion: p=0.0000), as well as from each other (p=0.0000). Topological plots (not shown) of the scalp peak alpha band amplitude distribution show a negative bias in the left central and parietal scalp regions for the activation method, a pattern much like that for the 'true' source with a corresponding difference plot bias in the central region; the pseudo-inversion method shows a strong negative bias in the right occipital scalp region and a corresponding positive bias in the frontal regions with the difference reflecting this backward tilt in the distribution.

Figure 22F:
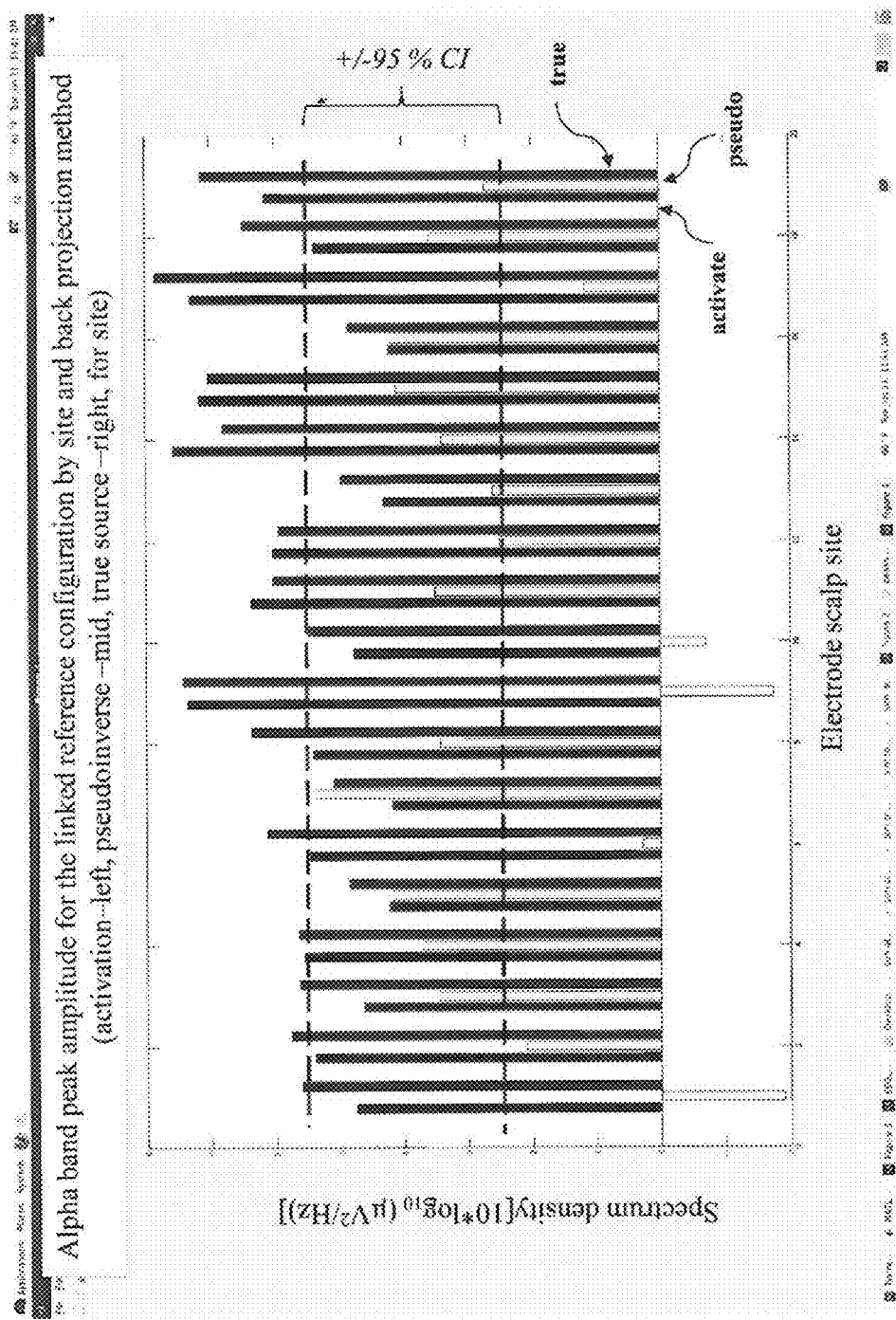
FIG. 22f shows alpha band peak amplitude for the linked reference configuration by site and back projection method.

Linked Ear Configuration:

FIG. 22f is a bar plot of the alpha band peak amplitude for the linked ear reference configuration by site and back projection method; a 95% CI for the average true value is shown for reference. The figure shows that while the peak amplitude for the activation method (activate) is well within the CI for the true values (true), those for the pseudoinverse method (pseudo) are well outside the CI for many of the electrode sites. A pairwise correlation analysis shows that the activation method results are significantly correlated with those of the 'true' source (Rc=89.90%, Pc=0.0000), but the pseudo inversion method results are not (Rc=−27.19%, Pc=0.2601), and neither do the two methods with each other (Rc=−18.77%, Pc=0.4415). The average and standard deviation statistics are for the activation method [5.59; 1.14], and the pseudo inversion method [2.42; 2.07], showing a narrower distribution for the activation method but a slightly wider distribution for the inversion. A paired sample t-test shows that the activation and inversion peak distributions are significantly different in amplitude from that of the 'true' source (activation: p=0.0011; inversion: p=0.0000), as well as from each other (p=0.0000). Topological plots (not shown) of the scalp peak alpha band amplitude distribution show a positive bias in the right parietal and occipital scalp regions for the activation method, a pattern much like that for the 'true' source with a corresponding difference bias in the central region; the pseudo-inversion method shows a strong positive bias in the temporal scalp regions and a corresponding bias in the difference plot.

Summary:

Considering the effects of the reference configurations on the 'true' source alpha band peak amplitude distributions, those for the inert and linked references have the same topological shape positively biased toward the scalp posterior with the linked distribution stronger than that for the inert, while the distribution for the average reference is flatter of intermediate strength and with a wider variance overlapping those of the other configurations. Considering now the isolated signals generated by the back projection methods, the activation method distributions are significantly correlated with those for the 'true' source for all reference configurations, while those for pseudo inversion method are not. The activation method distributions are stronger and with less variance for all reference configurations than are those for the inversion method. The distributions for both methods have about the same strength and variance for the inert and linked configurations, while those for the average reference have less strength; in particular, the distribution for the inversion method with the average reference has less strength and a much wider variance than with other references.

Summary of Case Studies:

Of the artifact rejection techniques studied, the abnormal spectrum rejection technique was the most effective resulting in an accurate reproduction of the source signal following parameterization, over a wide range of settings. This was true also for the abnormal amplitude technique, although the reproduction was not as accurate. The abnormal kurtosis and joint probability techniques resulted in stable representations, however with a bias offset over a moderate range of settings. The abnormal trend technique following band-pass filtering was largely ineffective. All techniques lead to distortions in the signal spectra, resulting in additional minor peaks at higher frequencies for the higher settings. Apparently, the distortions are influenced by the artifacts rejection, which implies that the signal results from data preprocessed at different settings may not be properly comparable for statistical analysis.

The effectiveness of the artifact rejection techniques is apparently influenced by the epoch size. These results follow a study in which the rejection techniques were applied in combination together sequentially over a range of settings for epoch, with the settings varied together for the rejection techniques. A plot of the peak amplitude of the isolated source PSD spectral shows a consistent increase in peak amplitude but different values by epoch size with setting increment over the middle range.

The effectiveness of Independent Component Analysis is determined by the number and spectrum of the independent components retained, as well as by the method of projecting the retained activations back to the electrode sites, at least as shown by this simulation study using power spectrum density (PSD) analysis. While some components are obvious ocular or muscle artifact sources and therefore should be removed, other components are graded combinations of source and artifact spectrums and may be ranked accordingly for removal. The strength of the back-projected scalp potentials is increased by including more components, but the lower frequency muscle spectrum content may distort the topological distribution. For small electrode sets such as the 10-20 electrode system, a direct method of conditioning the retained activations for projection back to the electrode sites may be more effective than using an inverted reduced weight matrix commonly derived by the Moore-Penrose pseudoinverse method because of the resulting ill-conditioning. In this study as an example, back projection by the pseudoinversive matrix following removal of obvious artifact components for ocular and muscle resulted in a significant bias toward the parietal scalp sites and away from the frontal sites as compared to the true source signals; with the same projection method following removal of both obvious artifacts and severely graded sources, the bias was toward the mid-line central scalp with significantly reduced signal. In contrast, a direct method of back projection resulted in insignificant bias toward the central sites; however, the projection fit was less for the case of removing just the obvious artifact components, although the strength was reduced when both obvious and graded sources were removed.

When using independent component analysis for isolating cortical sources, the effect of the reference electrode configuration upon the validity of the analysis depends in part on the method used for back projection with more validity with the activation matrix conditioning than with the pseudo inversion matrix. While the results are about the same for 'point' site reference electrode configurations, the results for an average site reference configuration are not as strong and more diffused, particularly with the pseudo inversion matrix method.

Application of Invention for Estimating Cerebral Cortical Source Activations

Figure 23A:
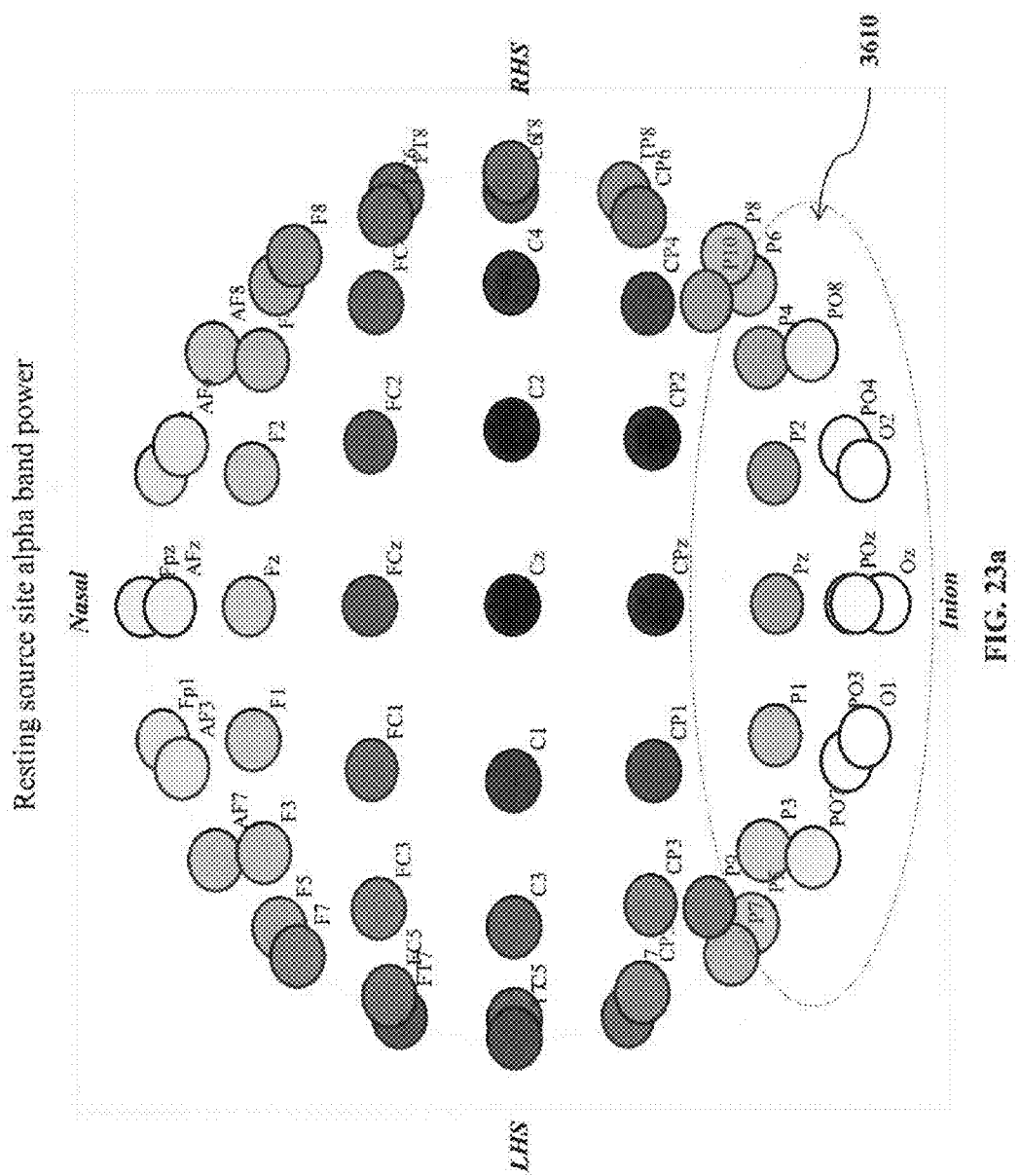
FIG. 23a shows resting site alpha band power.

As demonstration of the application of the invention for estimating cerebral cortical source activations from encephalograms (EEG), the case of a vehicle driven by a human operator is considered where the operator has been driving a well-known straight-path course for some time without environmental changes; in this case the operator is experiencing drowsiness and with little need for focused attention to his well-learned task, and correspondingly, the EEG is largely composed of delta and alpha waves distributed topologically over the scalp with more alpha waves in the posterior sites for this 'resting' state. FIG. 23a shows a feasible scalp site topological distribution of the alpha band spectrum power as recorded by a 64-electrode site system, with the electrode sites labeled accordingly, and the scalp orientation designated by the Nasal at the front and Inion position at the back of the skull, and by the left (LHS) and right (RHS) sides as seen looking down on the scalp. The alpha power is strongest in the posterior regions 3610 as can be seen from the grayscaling for intensity with the lighter gray being high intensity and darkest being the weak intensity.

Figure 23B:
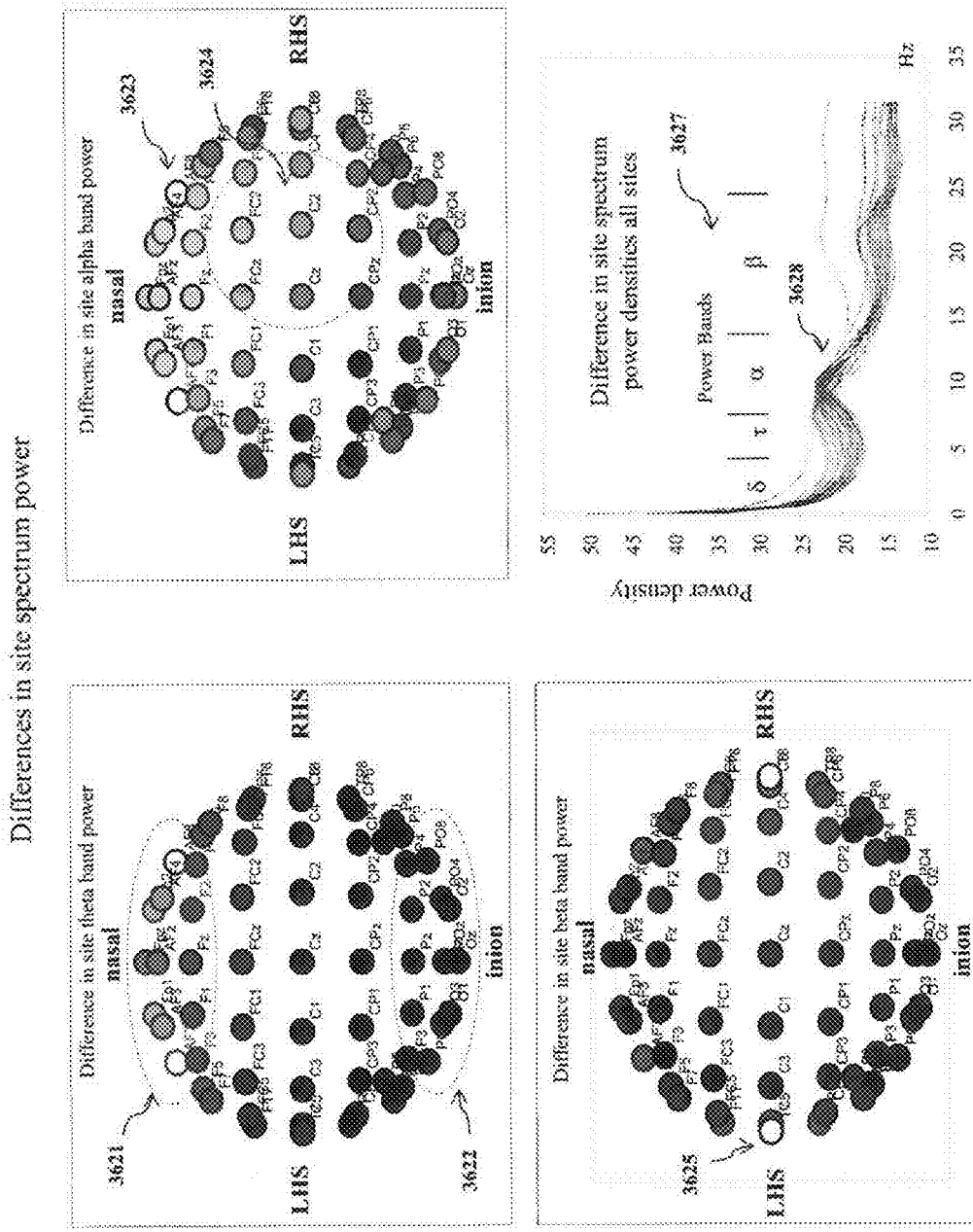
FIG. 23b shows differences in site spectrum power.

Now consider the case of a lateral wind gust as an environmental change disturbing the vehicle control. At this occurrence, the operator is presumed to physical adjust the driving control to correct for the lateral displacement while using vision to control the adjustment in response to the disturbance. FIG. 23b shows the expected difference between the prior resting state EEG scalp site topology of FIG. 23a and that resulting from scalp EEG measurements that are made during the control adjustment (not shown). Here, the figure shows the differences in the scalp site topology distribution for the theta, alpha, and beta frequency band spectrum power densities. The theta topology shows strong positive differences in the frontal sites 3621 and particularly in the sites near the eye-orbits, and negative differences in the posterior regions 3622. The alpha topology shows little differences in the frontal and posterior except for strong positive differences about the eye-orbit 3623, and strong negative differences on the right central region 3624. Continuing, the beta topology shows negative differences throughout except for strong positive differences near the ears 3625. Also shown are plots of the differences in the electrode site spectrum power densities as a function of frequency superimposed for all sites. For reference, the plot shows the frequency ranges for the delta (δ), theta (τ), alpha (α), and beta (β) frequency bands 3627. The frequency plot for these differences shows a large delta component and slight peaks in the theta, alpha 3628, and beta bands.

In this demonstration, the cerebral cortical source activations made during the control action response to the disturbance are estimated by simulation of both cortical sources and artifacts made with parameters that are adjusted for matching the predicted scalp potentials to the measured encephalograms. Considering the artifacts, the ocular and head movements may be independently measured by a video camera return, and similarly the muscular activations from the movements of the controls (with inputs to the artifact status indicator 127 [FIG. 1]). On this basis, the artifact potentials may be simulated separately for the ocular and head muscle sources (by the artifact signal generator 150 [FIG. 1]). FIG. 23c shows scalp site topology of artifact generated potentials that are simulated for these sources. The plot shows scalp site topology for the theta band spectrum power density from the ocular sources, and that for the beta band power density from the muscular sources. Also, shown are plots of the electrode site spectrum power densities as a function of frequency superimposed for all sites, along with the frequency ranges for the delta (δ), theta (τ), alpha (α), and beta (β) frequency bands. Considering the ocular artifact sources, the corresponding theta band scalp site topology shows strong power in the eye-orbit regions 3631, and minimal over the rest of the scalp; the alpha band topology is similar (not shown); the frequency plot shows strong delta and theta 3632 components as would be expected for eye-movements and blinks. Considering the muscular artifact sources, the corresponding beta band scalp site topology plot shows strong power in the region of the neck muscles 3633 to the sides of the skull and minimal over the rest of the scalp; the frequency plot shows higher power in the beta range 3634. The result of the subtraction of these topology plots for the artifact sources, from the error plot of FIG. 23b would be the site potentials (not shown) to be simulated by the cortical sources.

As noted, the operator is presumed to physical adjust the driving control to correct for the lateral displacement while using vision to control the adjustment in response to the disturbance (with inputs to the task status indicator 123 [FIG. 1]). Considering the cerebral sources for this activity, it would be expected that the counter-lateral motor cortex region would exhibit a decrease in alpha band waves (as Mu-band waves) and an increase in beta waves with the fine motor adjustments, while the frontal cortex would exhibit a decrease in alpha waves and an increase in theta waves corresponding to the evaluation of the scene, particularly the lane offset (via the expert system 130 [FIG. 1]). FIG. 23d shows a cerebral source topology as a top view of the brain cortex with cortical sources located by Brodmann area numbers indexed by hemisphere (right [R] or left [L]); the sources are grouped in clusters as these of the frontal lobe 3641 (including left and right anterior cingulate cortex [ACC]), those of the occipital and temporal lobes together 3642, and separately the right motor region (right BA4) 3643 as counter-lateral to the control action. For the simulation (via neural source signal generator 140 [FIG. 1]), the sources are located by hemisphere, lobe, Brodmann area, and Talairach head space coordinates; and the moment orientation by directional cosines in the sagittal plane, the coronal plane, and the transverse plane with the moments normal to the cortical surface for simplicity. Also shown in the figure are spectrum power densities plots as a function of frequency for the sources in the clutters. The plot for the frontal sources ('frontal') has a strong theta component 3644, some delta, and some alpha; that for the occipital and temporal lobes ('occipital') has slight delta and strong alpha 3645; while that for the motor source region ('motor') has slight delta, slight alpha (as Mu band waves), and strong beta 3646 corresponding to fine motor movements.

Figure 23E:
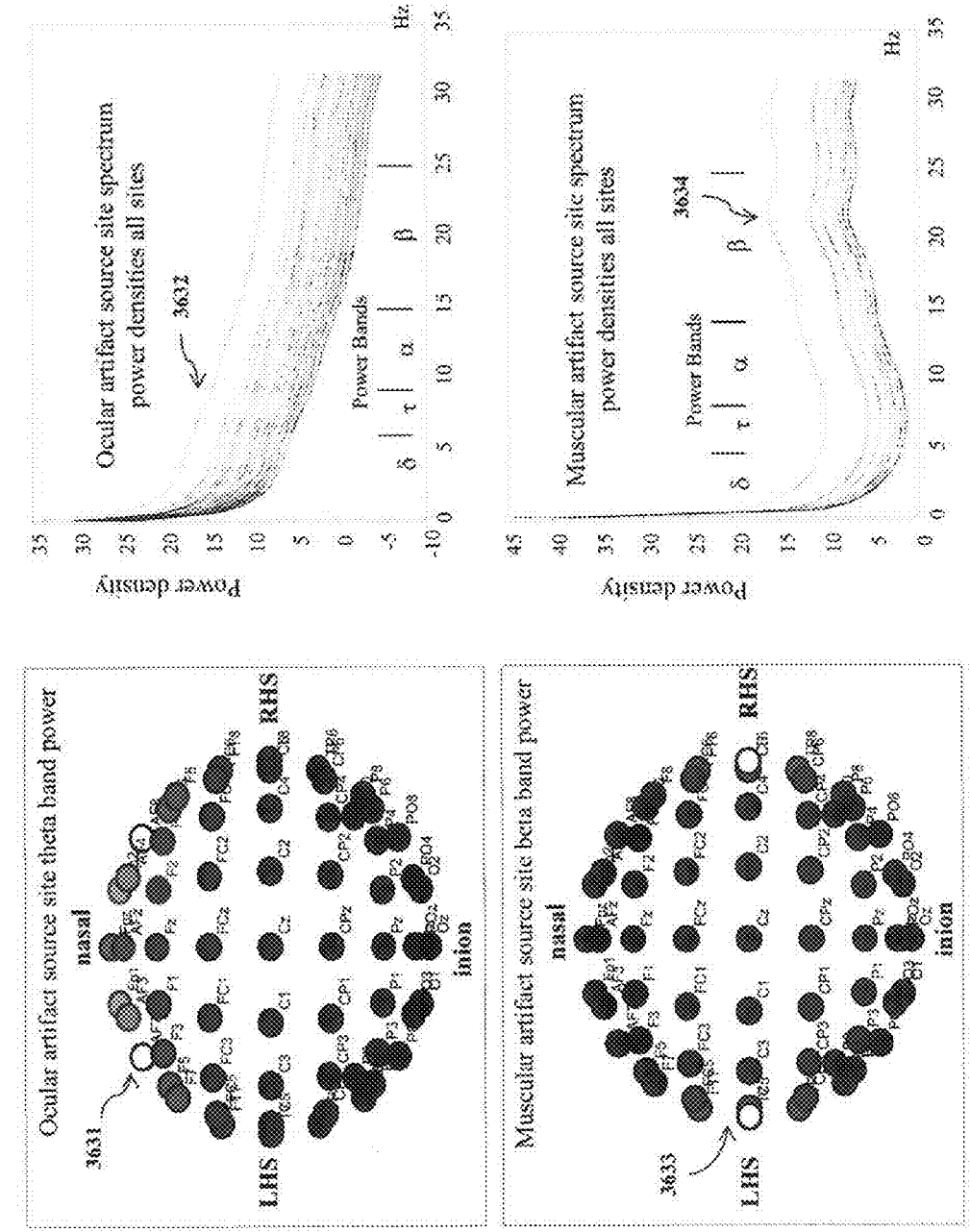
FIG. 23e shows cerebral source site spectrum power.
Figure 23D:
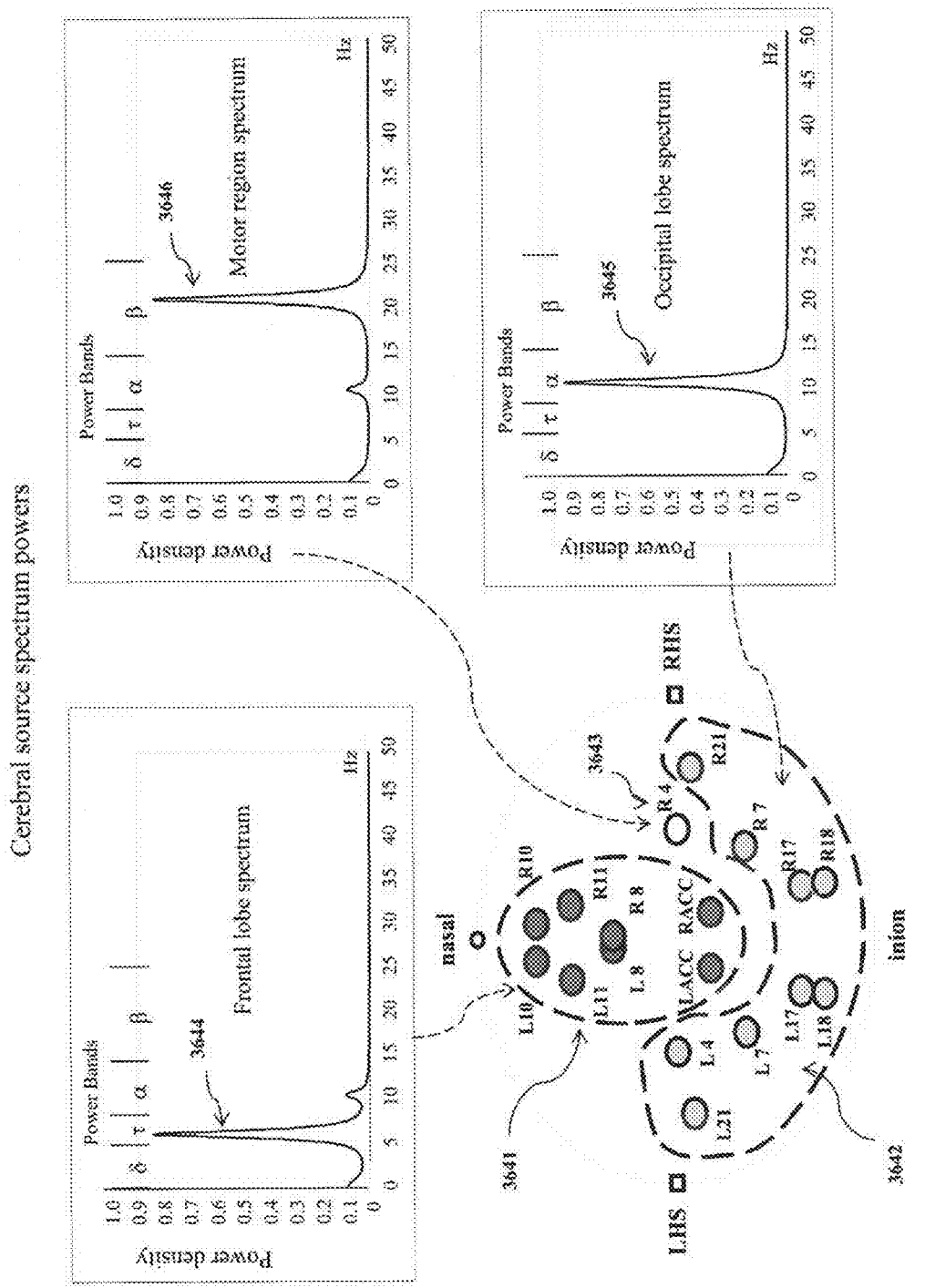
FIG. 23d shows cerebral source spectrum powers.
Figure 23E:
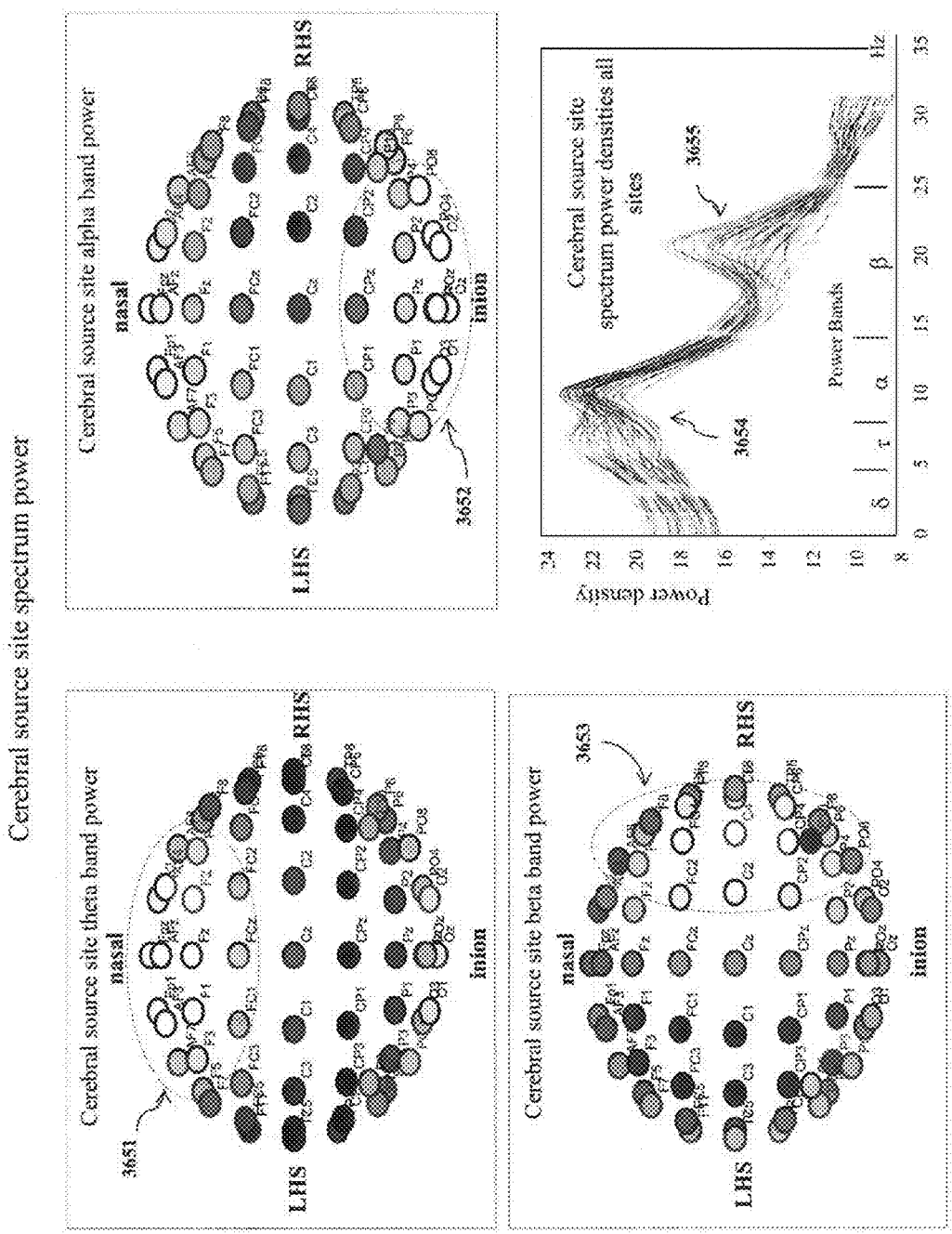

FIG. 23e shows the scalp site topology of the theta, alpha, and beta band spectrum power densities for the potentials simulated by the cortical sources. Also, shown in the figure are plots of the electrode site spectrum power densities as a function of frequency superimposed for all sites, along with the frequency ranges for the delta (δ), theta (τ), alpha (α), and beta (β) frequency bands. The topology plots show strong theta power in the frontal anterior mid-line region 3651 that decreases toward the posterior; strong alpha power in the occipital lobe 3652 that while extending throughout is minimal in the right motor region; and strong beta power in the right motor region 3653 with however minimal in the left motor region. The frequency plot shows strong frequency peaks in the theta, alpha 3654, and beta 3655 bands.

Figure 23F:
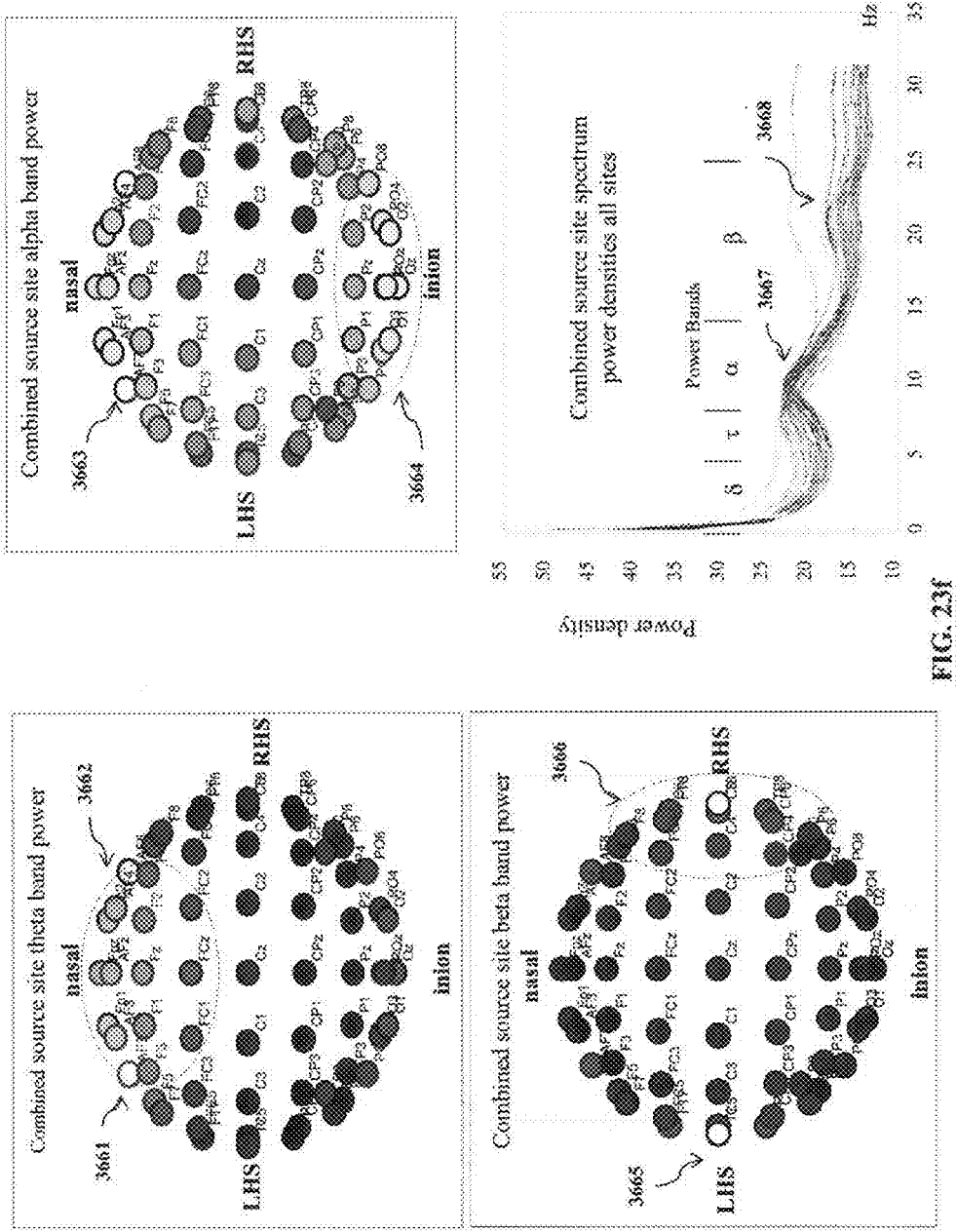
FIG. 23f show combined source site spectrum power.

FIG. 23f shows the scalp site topology of the theta, alpha, and beta band spectrum power densities for the scalp site potentials simulated by adding together those potentials for the cerebral sources with those for the ocular and muscular artifact sources (via the scalp site signal generator 160 [FIG. 1]). Also, shown are plots of the electrode site spectrum power densities as a function of frequency superimposed for all sites, along with the frequency ranges for the delta ($\delta$), theta ($\tau$), alpha ($\alpha$), and beta ($\beta$) frequency bands. The topology plots show strong theta in the frontal about the eye-orbits 3661, some anterior mid-line 3662, but minimal for the rest; strong alpha in the frontal region about the eye-orbits 3663, some in the occipital 3664, and minimal in the right motor region; and strong beta in the right and left side 3665, slight in the right motor region 3666, and minimal throughout the rest of the topology. The frequency plots show weak spectrum peaks in the theta, alpha 3667, and beta 3668 ranges. In this demonstration, the scalp site potentials simulated for FIG. 23f would be compared (by signal comparator 170 [FIG. 1]), to those of the EEG scalp site measurements (via EEG signal sampler 180 [FIG. 1]) used for FIG. 23b, and the differences used to adjust the parameters of the simulation (via controller 110 [FIG. 1]), for a best fit of the simulation to the measurements.

Application of Invention for Automated Aiding

The invention has applications as a component of an automated aiding system in the electronic aiding of tasks performed by human operators for crew-served systems including aiding for operators of combat vehicles and robotic control stations, by providing an estimate of localized brain functions from electroencephalogram measurements. The invention has particular application to such electronic task aiding systems for enhancement of task attention to cognitive functions by automated task cueing and in further embodiment, by direct brain stimulation; as well as for quickened manual control. The advantage of the invention to this process is the precise localization of brain functions that results from the simulation of the cerebral cortical source activations; and for this reason, the brain function enhancements may be targeted to these localized regions for specific functions.

FIG. 24 is a schematic showing the invention as part of an electronic task aider 5300 for a human operator. Here, the operator 5302 may be viewing a display 5305 with an overlaid aiding cue 5307. As with FIG. 2a, behavior related signals such as ocular functions 5318, activities 5322, electromyograms 5332, and encephalograms 5342, among others, are collected for processing by the invention 5360 configured as the pre-processor 201 (of FIG. 2a) of the input signals for the cortical source activity estimator 100 (of FIG. 1), with output of the brain functions 5362. The brain functions are input to a task attention manager 5370, which with input of the needed task attention status 5374 from the electronic task aider, sets aider cue parameters 5376 for the display driver 5380. In a further embodiment, the task attention sets parameters 5372 for brain function enhancement by transcranial direct current stimulators 5342 mounted about the scalp of the operator. In a still further enhancement, the task attention manager sets parameters 5378 for direct brain control by the operator through a process controller 5390 with process control signal 5394, depending upon the activation of the brain motor cortex modeled to at least the level of the primary motor cortex for the regions representing the limbs and hands as located in the central sulcus.

The invention may enable refined task cueing by an automated system that electronically aware of the task priorities, schedules the information needs for the task and arranges such in a display format that is in a manner supportive of the performance by the operator; in particular, such corresponding to a cognitive flow rate in the operator that is compatible with control dynamics that may be needed for a task. Here, the invention provides a precise specification of the brain functions from the source activations as the schedule is executed allowing adjustments to be made as the task is performed.

A common design feature of such an electronic aider is an embedded model of operator cognitive attention that with knowledge of task demands may be used for scheduling the information display. In some designs, the model may comprise an information processing model with cognitive processors controlled by a model executor, and rules for the activation of the corresponding processors along with associated task times and cost elements based on mapping attributes of cognitive attention. Still further, in some designs the model may be incorporated within a skills-based, rules-based, and knowledge-based model of cognitive processing; where the executor recalls task rules from the knowledge base and in evaluation sets up the rules for activation, the rules base processor activates the rules directing control, and the skills based processor controls the task execution. With this model, a control strategy for scheduling displays is determined by a process that with access to the processor task times and cost-elements, computes associated cost variables for sub-task combinations; and selects the optimal cost schedule to best facilitate task cognitive attention. In this process, cognitive attention is used as a metric for the event sub-tasks, where the attention is an element of an attention state set ranked by the degree of cognitive involvement of such ordered from task initiation to task completion. In further elaboration, the ranking is by the states of orientation, task recall, task focus, option review and decision, activation, and continual control. Here, reference is made to U.S. patent application Ser. No. 13/721,161, filed Dec. 20, 2012, and further to U.S. patent application Ser. No. 13/792,585, filed Mar. 11, 2013, both by the inventor, for further teachings of modeling task attention.

An important step in the scheduling process is knowledge of the attention state of the human operator determined here by the invention as processor 5360 configured as the pre-processor 201 (of FIG. 2a) of the input signals for the cortical source activity estimator 100 (of FIG. 1), with output of the brain functions (and attention state) 5362 to the task attention manager 5370, since a fully ordered schedule sequence starting from initiation could interrupt the cognitive flow being executed by the operator, who may already be involved in the task. The interruption may disorient the operator resulting in an evaluation of the displays, and consequently poor performance until the operator recovers. For this reason, the scheduling is initialized from the task attention state of the operator as determined by an electronic task attention processor from measurements from the operator, such as eye movements and eye-gaze fixations, measurements of the state of brain cognitive functions, and manual activity in performance of the tasks, as well as the state of the task performance. In this design, the invention as embodied below estimates the states of the cognitive processors of the scheduling model for the task attention processor from the brain cognitive functions as determined from electroencephalogram measurements. Since the skill controlling brain processes are sub-cortical, they cannot be readily determined from electroencephalogram measurements using standard technology, and the state of the model skill processor is estimated by the task attention processor from the skill-based ocular and manual activities. Further, the relation of the operator's attention to the task is determined by the task attention processor from the status of the task. Here, reference is made to U.S. Pat. No. 8,708,884 by the inventor, titled: "Systems and methods for adaptive mitigation of motion sickness," herein incorporated by reference, for further teachings of reducing operator activities to estimates of the cognitive attention state.

In this design, the cerebral cortical source nodes may be mapped to Brodmann Areas and the corresponding brain functions. As mentioned above, the occipital, somatosensory, and temporal cortical lobes are organized as processors for primary sensory areas (vision: BA17; somatosensory: BA1, 2, 3; temporal: BA41 for auditory, BA43 for gustatory), and secondary sensory areas (vision: BA18; somatosensory: BA5; temporal: BA42 for auditory), association areas (vision: BA19; somatosensory: BA7; temporal: BA22), along with multiple association areas in the parietal and temporal (BA20, 21, 15), which in turn lead to the frontal lobe for evaluation (BA9, 10, 11, 12), with pre-motor frontal eye-fields for directed vision (BA8), and secondary motor (BA6) and primary motor (BA4) for action. Specialized temporal and frontal areas process language understanding (BA39, 40) and generation (BA44, 45). These functions may be specialized further by cortical hemisphere. In addition, the anterior cingulate is believed involved in error detection (BA24, 32) and the posterior cingulate in emotion (BA23, 31). Further involved are the limbic system regions of entorhinal cortex (BA34), perirhinal cortex (BA35), and the ectorhinal area (BA36) of the perirhinal cortex, among others for spatial memory and orientation.

Further, the cortical brain functions of the source node network may be mapped to the cognitive processing network for classification of attention to a task. In this process, the modulator sources are a measure of the strength of attention, while the network topology corresponds to the attention involvement. As has been mentioned above, a default network corresponding to self-referral has less clustering and efficiency and is more spread out in a form of 'scale free' network; a task focused network would be spread out but with high degree and high diameter, as well as high clustering and high efficiency; and a task response network would perhaps be a 'small-world' network that has less degree and diameter, and greater clustering and efficiency.

In some embodiments, the classifier outputs of the brain cognitive state may be mapped through the knowledge base of the expert system to the state of information processing as expressed by a cognitive processing model for the human operator, and in particular, to the states of the separate processors making up the model from the corresponding cortical networks. In this process, the cortical structure as located by the Brodmann Areas of the network may be mapped to a model of information processing, where in some designs, these models comprise cognitive processors controlled by a model executor, and rules for the activation of the corresponding processors as components of an information processing network. As has been mentioned, the model may be incorporated within a skills-based, rules-based, and knowledge-based model of cognitive processing; where the executor recalls task rules from the knowledge base and in evaluation sets up the rules for activation, the rules base processor activates the rules directing control, and the skills based processor controls the task execution. In this model, the levels of involvement of the processors depend upon the attention state of the network as determined by the executor.

There is a neurological basis for the validity of such a model within the human cerebral cortex with presumably the executor mapped to the orbitofrontal cortex believed involved in planning, the knowledge base to the temporal lobes, the rules processor to the anterior parietal and the pre-motor cortex with control setting to the motor cortex. The skills processor may be mapped to the cerebellum with a reference setting from the motor cortex and visual offset from the pontine nuclei via the posterior parietal for foveal vision or even directly from the visual cortex for peripheral vision. Further, the reference may be set by the parietal cortex in visual-egocentric coordinates for comparison to delayed visual returns. The cerebellum is believed essential to coordinating motor limb and digit movements. Each of these centers taken together may comprise cortical attention networks for eye-movements, working memory, spatial distribution, and temporal expectation, within the frontal, temporal and parietal brain regions. Again, reference is made to the aforementioned '161 and '585 patent applications for further teachings of modeling task attention.

In a further embodiment, the invention may enable direct stimulation of brain functions for enhancement of task attention by devices placed in an array about the scalp, where a device would be applicable to a localized brain area, and where the device controller sets the stimulation according to the state of the brain area as determined by the invention from the area source activations. In this process, the invention would be part of the controller with feedback on the source activations both before stimulation and after application.

In one embodiment, the use of the invention enabling precise application of direct brain stimulation to localized areas of brain functions may be by transcranial direct-current stimulation (tDCS). In this technique an extremely low amperage electrical current is applied to the brain by electrodes attached to the scalp; in this process, the electricity crosses through the cranium skull from a cathode electrode to the anode electrode, thereby causing brain cells near the anode to become excited. Commonly, a nine-volt battery is used generating less than a milliamp current with only minimal side effects such as a mild tingling at the electrode site which quickly becoming imperceptible. The stimulating current activates network of neurons making it easier to fire and resulting behaviors to be carried out. The brain region affected may be either mildly activated or inhibited depending upon the polarity of the stimulating current. The technique has been shown to mildly enhance a variety of intellectual, emotional, and movement related brain functions, including increased speed and accuracy performing attention switching task, enhancements in working and long-term memory, and increased vigilance and target detection. It should be noted that the effect of these enhancements is to allow the users to operate at a fuller capacity in their own information processing and decision making.

Figure 25:
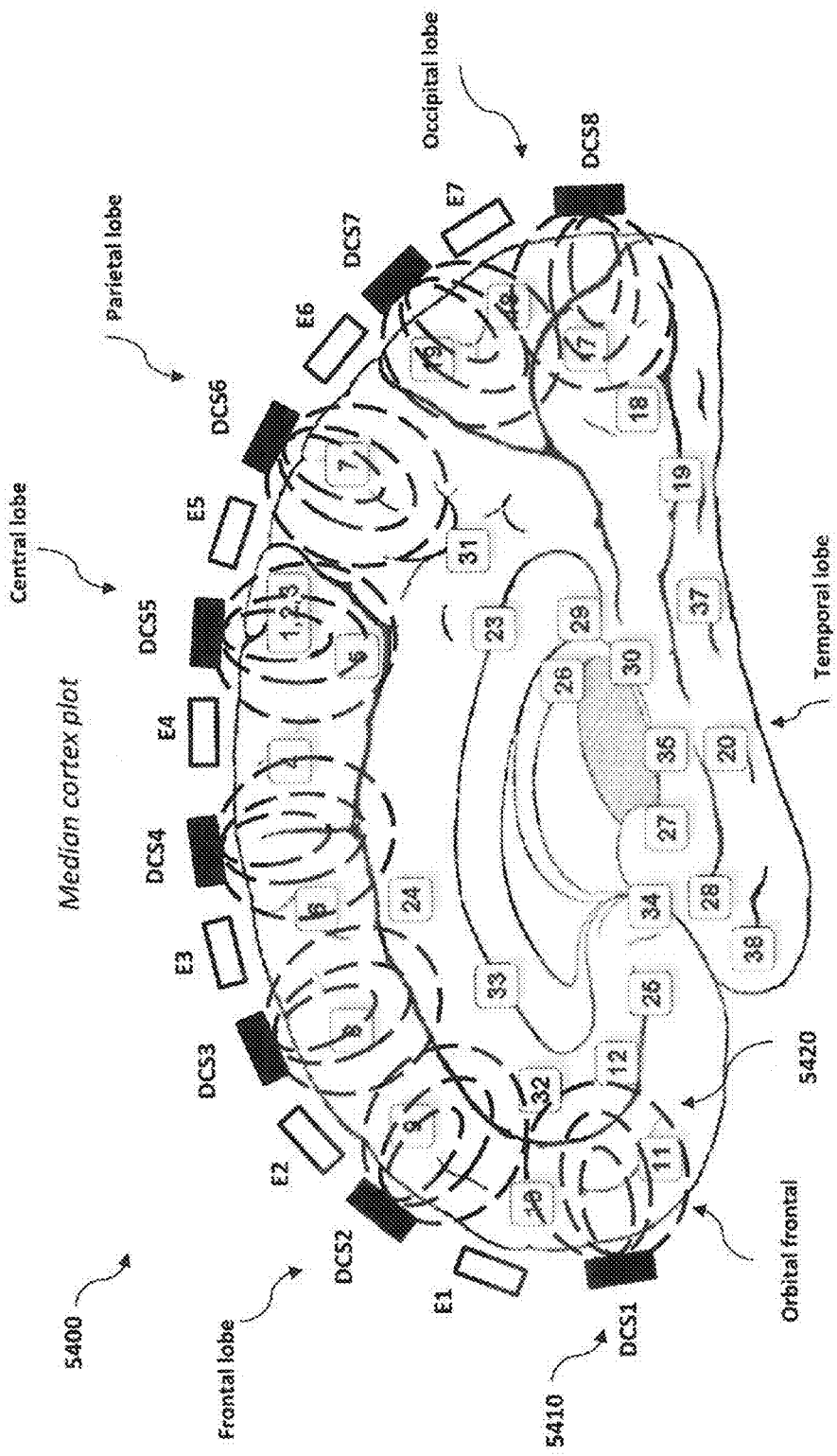
FIG. 25 shows median view of the human cortex with combined scalp sites electrodes and transcranial direct current stimulator.

FIG. 25 is a schematic showing a median cortical plot with a combined cortical enhancement and encephalograms measuring system 5400, composed of an array of scalp electrode sites E1 thru E7, interspaced among an array of transcranial direct current stimulators DCS1 thru DCS8, distributed over the scalp (here shown over the lateral line). Here, DCS1 as 5410 has an electrical excitation field 5420 of both the orbital frontal lobe and the surrounding scalp. The DCS is activated as needed to enhance brain functions within the immediate area by turning the device off and on, generating potential transitions in the process. In this embodiment, the invention has been further elaborated to model the DCS electrical output transitions as an additional scalp artifact from the stimulator off-on control signals. Still further, the DCS intensity may be used as a measure for simulating the corresponding cortical source dipole moment strength.

Figure 26:
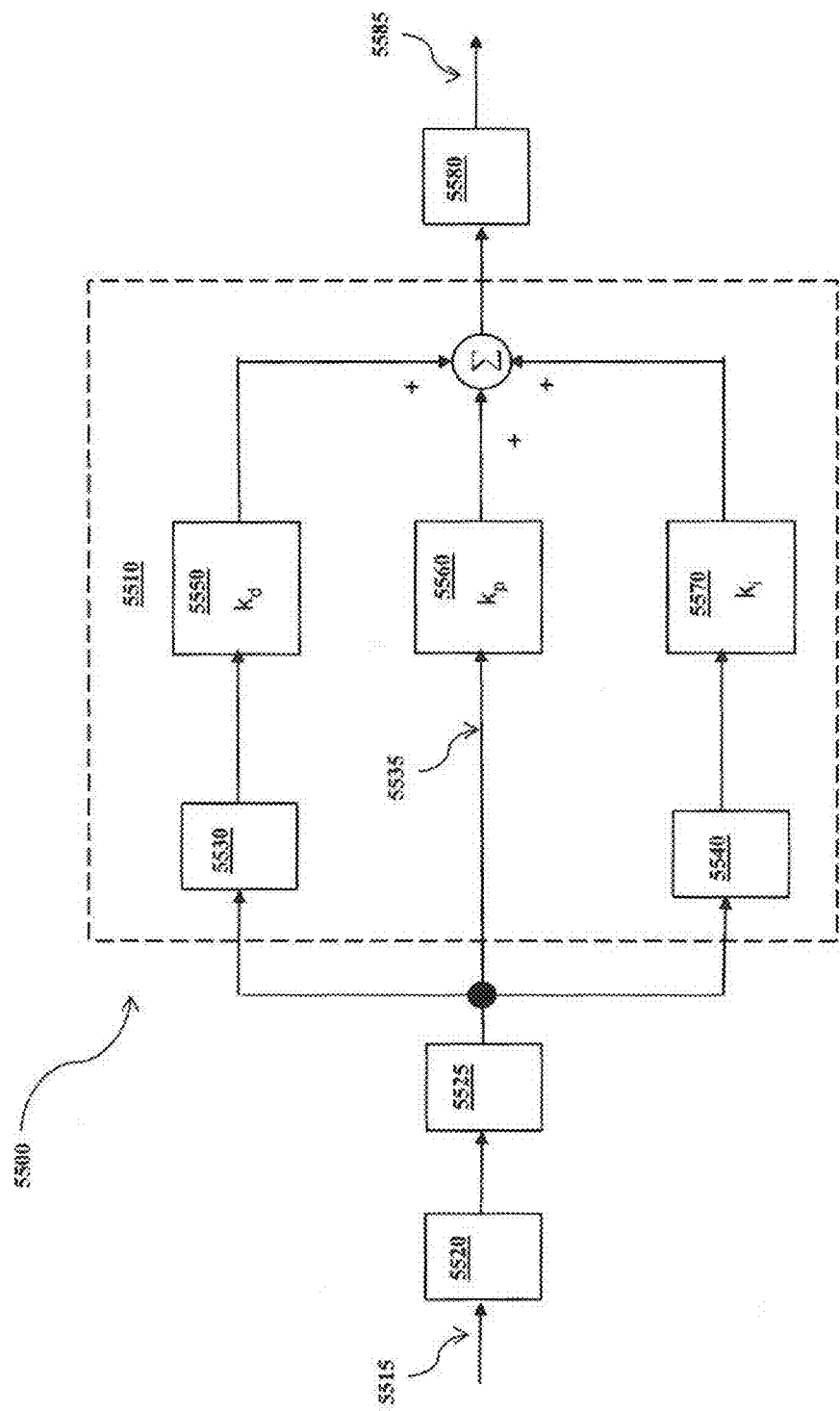
FIG. 26 shows schematic of PID controller for manual control enhancement with cerebral source activation input.

In a still further embodiment, the invention may enable quickened manual control from the state of source activations in the motor cortex regions of the supplementary, premotor and the primary motor areas. The activations correspond to the state of the control as determined by sources in the premotor and supplementary areas, and the source of the manual control as determined from the primary motor cortex for the regions representing the limbs and hands as located in the central sulcus. The state of the cortical source activations may be used by an electronic process controller for higher order aiding of the manual control and of display to the operator; and in a further embodiment, for direct brain control of the process from the motor cortex. FIG. 26 is a schematic of a possible controller in a Proportional-Integral-Differential (PID) configuration 5510, with input 5515 from an appropriate cortical source with input to a Beta band notch filter 5520 and intensity threshold 5525, and output for an integral signal 5540, proportional signal 5535, and differential signal 5530. The signals are weighted by error gains 5550, 5560, and 5570, and the sum of these weighted signals may be considered as the control signal 5585 following the gain 5580 for setting the manual control offset. Other controller configurations are possible such as a wavelet controller based on short term frequency and intensity of the cortical source, an artificial network controller with inputs from several cortical sources, and a fuzzy-logic controller, among others.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, to thereby enable others skilled in the art to best utilize the invention and various embodiments with various modifications as may be suited to the particular use contemplated.

Various elements, devices, modules and circuits are described above in associated with their respective functions. These elements, devices, modules and circuits are considered means for performing their respective functions as described herein. While the foregoing is directed to embodiments of the present invention, other and further embodiments of the invention may be devised without departing from the basic scope thereof, and the scope thereof is determined by the claims that follow.

TABLE 1

Oscillator function pairs

| Type | Spectrum | Autocorrelation. |
|---|---|---|
| I. | $sd(f) = \sigma * G/(\sigma^2 + f^2)$ | $rc(\tau) = G * \exp(-2 * pi * \sigma * \tau)$; |
| II. | $si(f) = \sigma i * Gi * (fi^2 + \sigma i^2 + f^2)/\ldots ((fi^2 + \sigma i^2 - f^2)^2 + (2 * \sigma i * f)^2)$ | $rc(\tau) = Gi * (\cos(2 * pi * fi * \tau)) * \exp(-2 * pi * \sigma i * \tau)$. |

TABLE 2

Muscle parametric relations

| Function | Equation. |
|---|---|
| Recruitment threshold | $th(i) = \exp(\ln(RR) * i/nm)/RR$ |
| Mean firing rate | $fr(i) = d * ft + (c - a * \exp(-ft/b)) * th(i) + e$ |
| Interspike interval | $ISI(i) = (1 + cv * Z)/(fr(i))$, where $Z \sim N(0)$. |

TABLE 3

10-20 electrode system: Site numbers and labels

| Number: | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| Label: | Fp1 | F3 | F7 | C3 | T7 | P3 | P7 | O1 | Pz | Fp2 | Fz | F4 | F8 | Cz | C4 | T8 | P4 | P8 | O2 |

TABLE 4

Pseudo-inverse Matrix Statistics by Component Category

| | Matrix | | Diagonal | | Off-diagonal | |
|---|---|---|---|---|---|---|
| Category | Mean | SD | Mean | SD | Mean | SD |
| I. | 0.011 | 0.221 | 0.895 | 0.150 | −.0380 | .064 |
| II. | 0.002 | 0.201 | 0.737 | 0.153 | −.0390 | .098 |

I claim:

1. A method for estimating cortical neural source activations of electrical voltage potentials from scalp site measurements of electroencephalograms (EEG) from a human subject that is executed by an electronic processor comprising electronic modules, the method comprising:
   specifying, by an electronic module, cortical neural sources within the brain of the subject;
   simulating, by one or more electronic modules, scalp site voltage potentials that correspond to scalp site voltage potentials which would be measured by electrodes of an EEG collection system worn by the subject, wherein the simulating comprises:
   (i) simulating activation potentials for the specified cortical neural sources;
   (ii) mathematically projecting the simulated cortical neural source voltage activations to actual scalp site measurement electrode locations of the EEG collection system worn by the subject;
   (iii) simulating scalp voltage potentials for one or more extra-cranial sources outside the brain; and
   (iv) calculating simulated scalp site voltage potentials from the projected simulated modeled cortical neural source voltage activations and the simulated extra-cranial scalp voltage potentials;
   receiving measurement signals for actual scalp site voltage potentials which originate from the EEG collection system worn by the subject;
   comparing, by an electronic module, the simulated scalp site voltage potentials and actual scalp site voltage potentials for the subject;
   adjusting, by an electronic module, parameters for simulating the cortical neural source voltage activations until the simulated scalp site voltage potentials generally correspond to the actual scalp site voltage potentials based on said comparison; and estimating, by an electronic module, cortical neural source activations for the subject from actual scalp site voltage potentials using the adjusted parameters.

2. The method of claim 1, wherein simulating the cortical neural source voltage activations comprises a noise driven autoregressive process.

3. The method of claim 2, wherein adjusting parameters comprises autoregressive spectra parameterization.

4. The method of claim 1, wherein simulating the extra-cranial scalp voltage potentials comprises simulating ocular electrooculogram and/or muscle electromyogram potentials.

5. The method of claim 4, wherein ocular orientations and eye-blinks are used as determinates for simulating electrooculogram potentials, and facial expressions and limb postures are used as determinates for simulating electromyogram potential sources.

6. The method of claim 1, wherein cortical source locations are mapped to cortical structures relatable to brain functions, which at the least spatial resolution are located within Brodmann Areas using a spatial coordinate system of the human brain.

7. The method of claim 6, wherein the cortical neural sources are determined from an attention state of the subject, wherein the attention state is processed from the activities of the subject and the cortical neural source determination is made from the corresponding brain functions for the attention state from the cortical structure mapping.

8. The method of claim 7, wherein the attention state for the cortical neural source activations is used as a basis for automated electronic task aiding of cognitive tasks.

9. The method of claim 8, wherein the automated task aiding of cognitive tasks employs transcranial direct current brain stimulation applied to enhance cortical neural source activations for the attention state.

10. The method of claim 8, wherein the cortical source neural activations are a basis for automated electronic task aiding of manual tasks.

11. An apparatus for estimating cortical neural source activations of electrical voltage potentials from scalp site measurements of electroencephalograms (EEG) from a human subject, the apparatus comprising an electronic processor comprising electronic modules which include:
an electronic module configured to specify cortical neural sources within the brain of the subject;
one or more electronic modules configured to simulate scalp site voltage potentials that correspond to scalp site voltage potentials which would be measured by electrodes of an EEG collection system worn by the subject, wherein said one or more electronic modules are configured to:
(i) simulate activation potentials for the specified cortical neural sources;
(ii) mathematically project the simulated cortical neural source voltage activations to actual scalp site measurement electrode locations of the EEG collection system worn by the subject;
(iii) simulate scalp voltage potentials for one or more extra-cranial sources outside the brain; and
(iv) calculate simulated scalp site voltage potentials from the projected simulated modeled cortical neural source voltage activations and the simulated extra-cranial scalp voltage potentials;
an electronic module configured to receive measurement signals for actual scalp site voltage potential which originate from the EEG collection system worn by the subject;
an electronic module configured to compare the simulated scalp site voltage potentials and actual voltage potentials for the subject;
an electronic module configured to adjust parameters for simulating the cortical neural source voltage activations until the simulated scalp site voltage potentials generally correspond to the actual scalp site voltage potentials based on said comparison; and
an electronic module configured to estimate cortical neural source activations for the subject from actual scalp site voltage potentials using the adjusted parameters.

12. The apparatus of claim 11, wherein simulating the cortical neural source voltage activations comprises a noise driven autoregressive process.

13. The apparatus of claim 12, wherein adjusting parameters comprises autoregressive spectra parameterization.

14. The apparatus of claim 11, wherein simulating the extra-cranial scalp voltage potentials comprises simulating ocular electrooculogram and/or muscle electromyogram potentials.

15. The apparatus of claim 14, wherein ocular orientations and eye-blinks are used as determinates for simulating electrooculogram potentials, and facial expressions and limb postures are used as determinates for simulating electromyogram potential sources.

16. The apparatus of claim 11, wherein cortical source locations are mapped to cortical structures relatable to brain functions, which at the least spatial resolution are located within Brodmann Areas using a spatial coordinate system of the human brain.

17. The apparatus of claim 16, wherein the cortical neural sources are determined from an attention state of the subject, wherein the attention state is processed from the activities of the subject and the cortical neural source determination is made from the corresponding brain functions for the attention state from the cortical structure mapping.

18. An improved method for estimating cortical neural source activations of electrical voltage potentials from scalp site measurements of electroencephalograms (EEG) from a human subject that is executed by an electronic processor comprising electronic modules, the method comprising:
specifying, by an electronic module, cortical neural sources within the brain of the subject;
simulating, by an electronic module, scalp site voltage potentials based on a model of cognitive processing that assumes measurements of scalp site voltage potentials by electrodes of an EEG collection system worn by the subject are the sum of cortical neural source activation potentials within the brain and artifact potentials arising from one or more extra-cranial sources outside the brain, wherein the simulating comprises:
(i) simulating activation potentials for the specified cortical neural sources;
(ii) mathematically projecting the simulated cortical neural source voltage activations to actual scalp site measurement electrode locations of the EEG collection system worn by the subject;
(iii) simulating scalp voltage potentials for one or more extra-cranial sources outside the brain; and
(iv) calculating simulated scalp site voltage potentials from the projected simulated modeled cortical neural source voltage activations and the simulated extra-cranial scalp voltage potentials;
receiving measurement signals for actual scalp site voltage potentials which originate from the EEG collection system worn by the subject;

comparing, by an electronic module, the simulated scalp site voltage potentials and actual scalp site voltage potentials for the subject;

adjusting, by an electronic module, parameters of the model of cognitive processing for simulating the cortical neural source voltage activations until the simulated scalp site voltage potentials generally correspond to the actual scalp site voltage potentials based on said comparison so as to derive a base line of the model for the simulated activation potentials for the specified cortical neural sources alone in the model; and estimating, by an electronic module, cortical neural source activations for the subject from actual scalp site voltage potentials using the model of cognitive processing with the adjusted parameters.

* * * * *